United States Patent [19]
Buck et al.

[11] Patent Number: 5,814,612
[45] Date of Patent: Sep. 29, 1998

[54] RETINOL DERIVATIVES AND USES THEREOF

[75] Inventors: Jochen Buck; Ulrich Hammerling; Fadila Derguini; Koji Nakanishi, all of New York, N.Y.

[73] Assignees: Sloan-Kettering Institute for Cancer Research; The Trustees of Columbia in the City of New York, both of New York, N.Y.

[21] Appl. No.: 880,041

[22] Filed: May 6, 1992

Related U.S. Application Data

[63] Continuation-in-part of Ser. No. 682,909, Apr. 9, 1991, Pat. No. 5,262,572.

[51] Int. Cl.[6] .......................... A61K 37/22; C07D 317/74
[52] U.S. Cl. ............................ 514/21; 514/725; 549/453; 549/512; 549/551; 549/554; 549/561; 549/563; 552/10; 552/11; 552/12; 558/430; 564/123; 564/152; 564/153; 562/867; 568/823; 568/824; 568/825
[58] Field of Search ...................................... 568/824, 825, 568/823; 514/21, 725; 549/551, 554, 561, 563, 512, 453; 560/125, 126, 127, 128; 562/867; 564/123, 152, 153, 191; 552/10, 11, 12; 558/430

[56] References Cited

U.S. PATENT DOCUMENTS 5,124,083  6/1992  Shealy ....................................... 514/529

Primary Examiner—Johann Richter
Assistant Examiner—John Peabody
Attorney, Agent, or Firm—John P. White

[57] ABSTRACT

The present invention provides a purified retinoid compound characterized by a molecular mass of about 320 daltons and an atomic composition of $C_{20}H_{32}O_3$. The present invention also provides a purified retinoid compound having the structure:

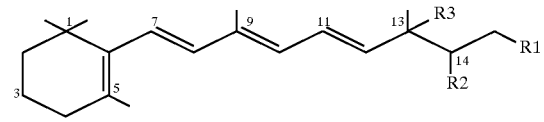

wherein the configuration of the C7, C9, and C11 double bond independently is Z or E and the absolute configuration at C13 and C14 is independently R or S; wherein R1 is alkyl, alkyl halide, alcohol, ester, ether, aldehyde, ketone, carboxylic acid, carboxylic ester, acyl halide, amide, nitrile, or amine; R2 and R3 are independently hydroxyl, halide, alkoxy, ester, alkyl, alcohol, ether, aldehyde, ketone, carboxylic acid, carboxylic ester, nitrile, amine, azide, alkyl halide, acid halide, acid azide, or amide; or wherein R2 and R3, or R1 and R2 are replaced by a 13,14-oxirane or a 14,15-oxirane group, respectively.

7 Claims, 75 Drawing Sheets

RETINOL

ALL TRANS RETINOIC ACID

RO10-1670 (ETRETINE)

RO 13-7410 (TTNPS)

RO 40-6055 (AM 80)

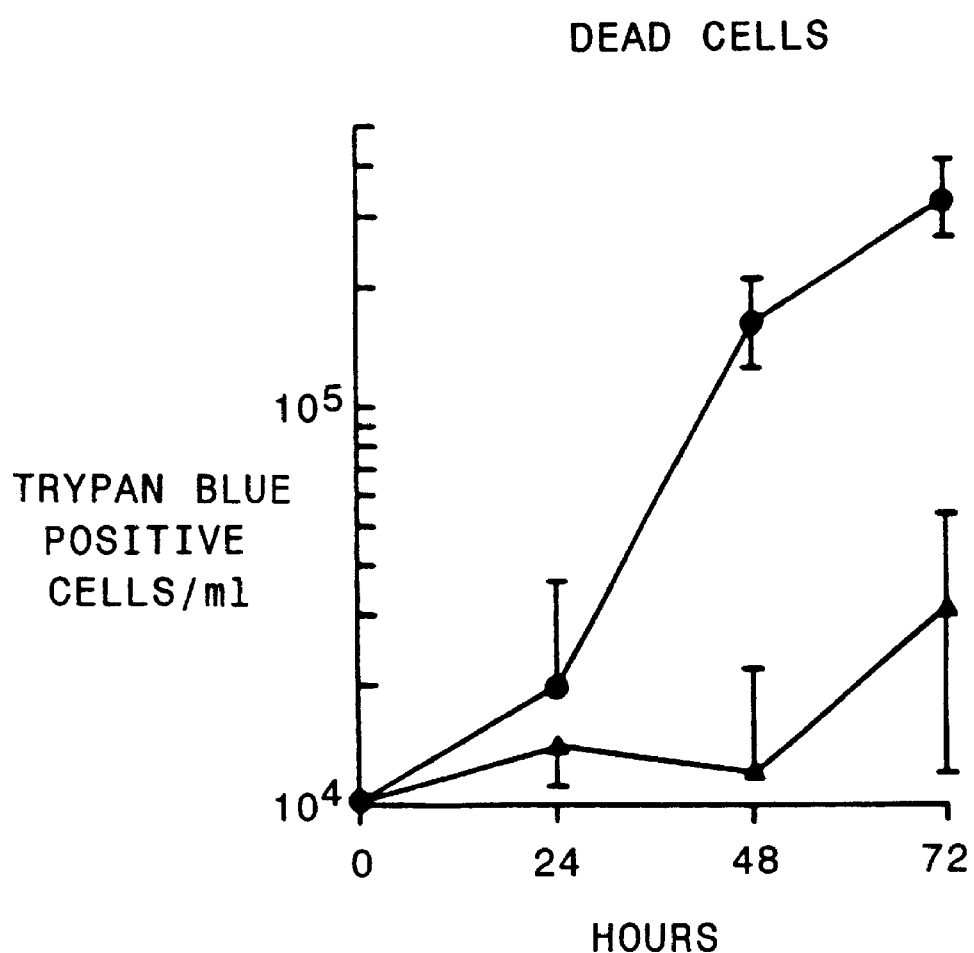

NORMAL (OR β-) RETINOID

RETRO-α-RETINOID

RETRO-γ-RETINOID

14-HYDROXY-4,14-RETRO-RETINOL (14-HRR)

14-HYDROXY-4,14-*RETRO*-RETINOL (14-HRR)

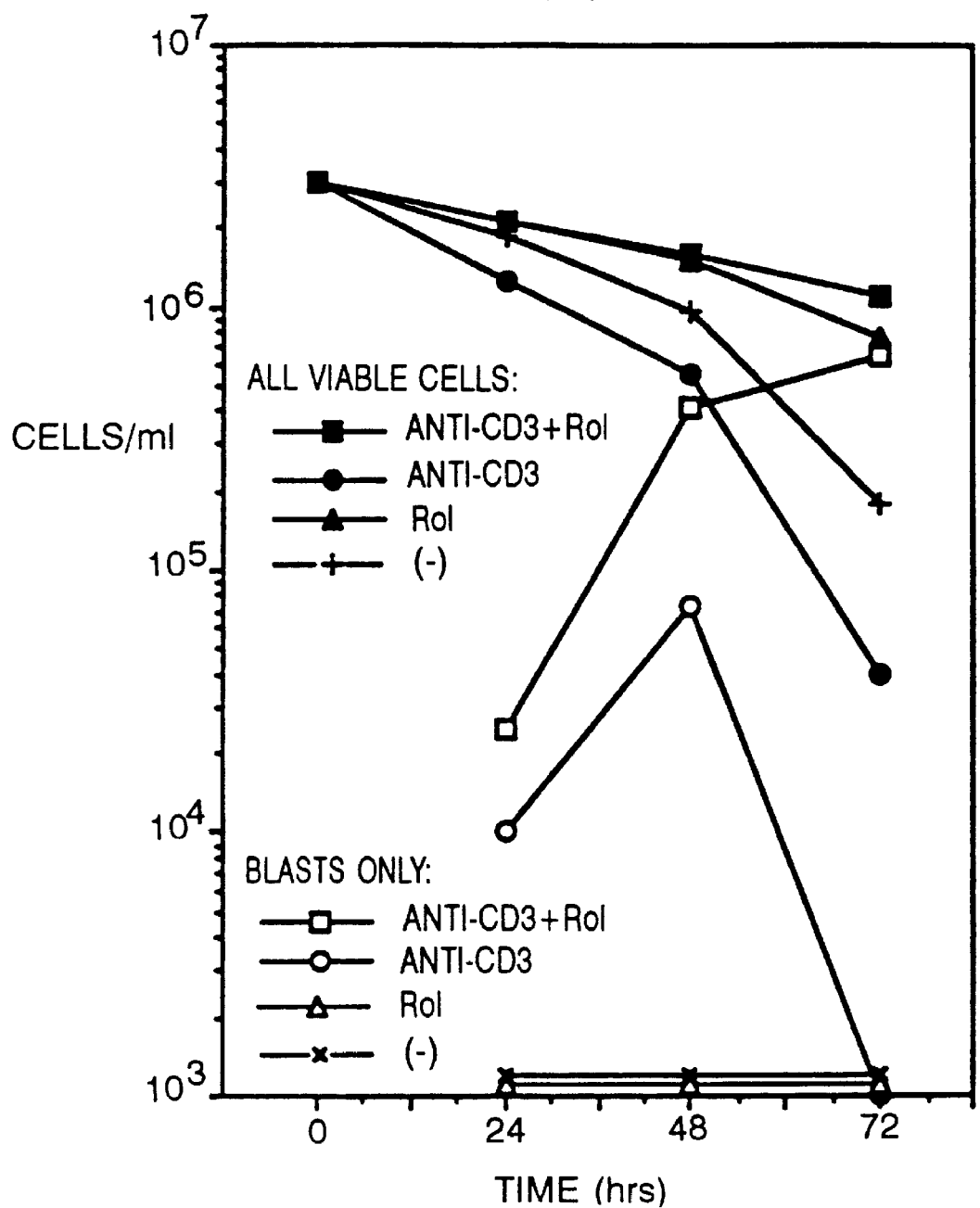

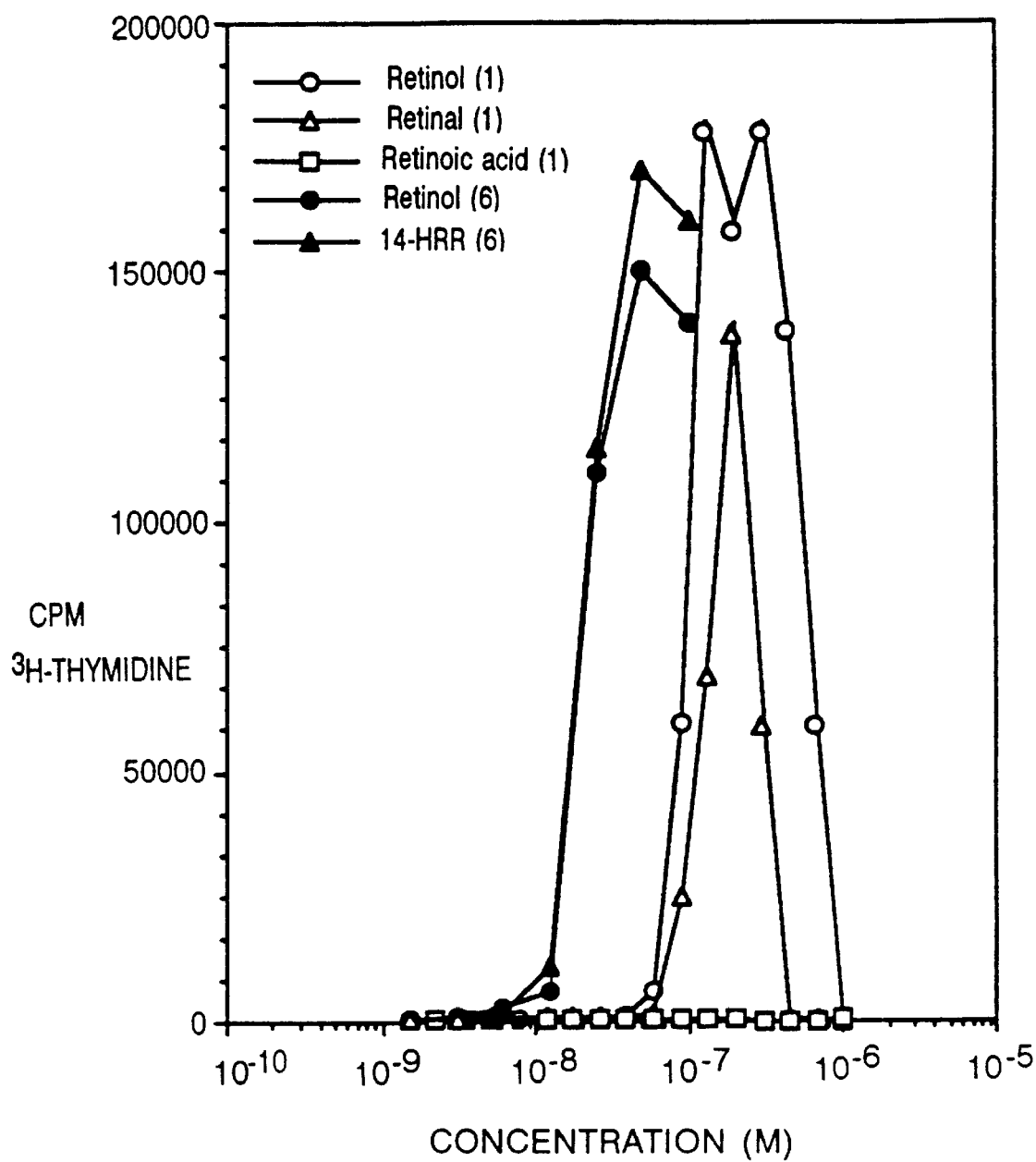

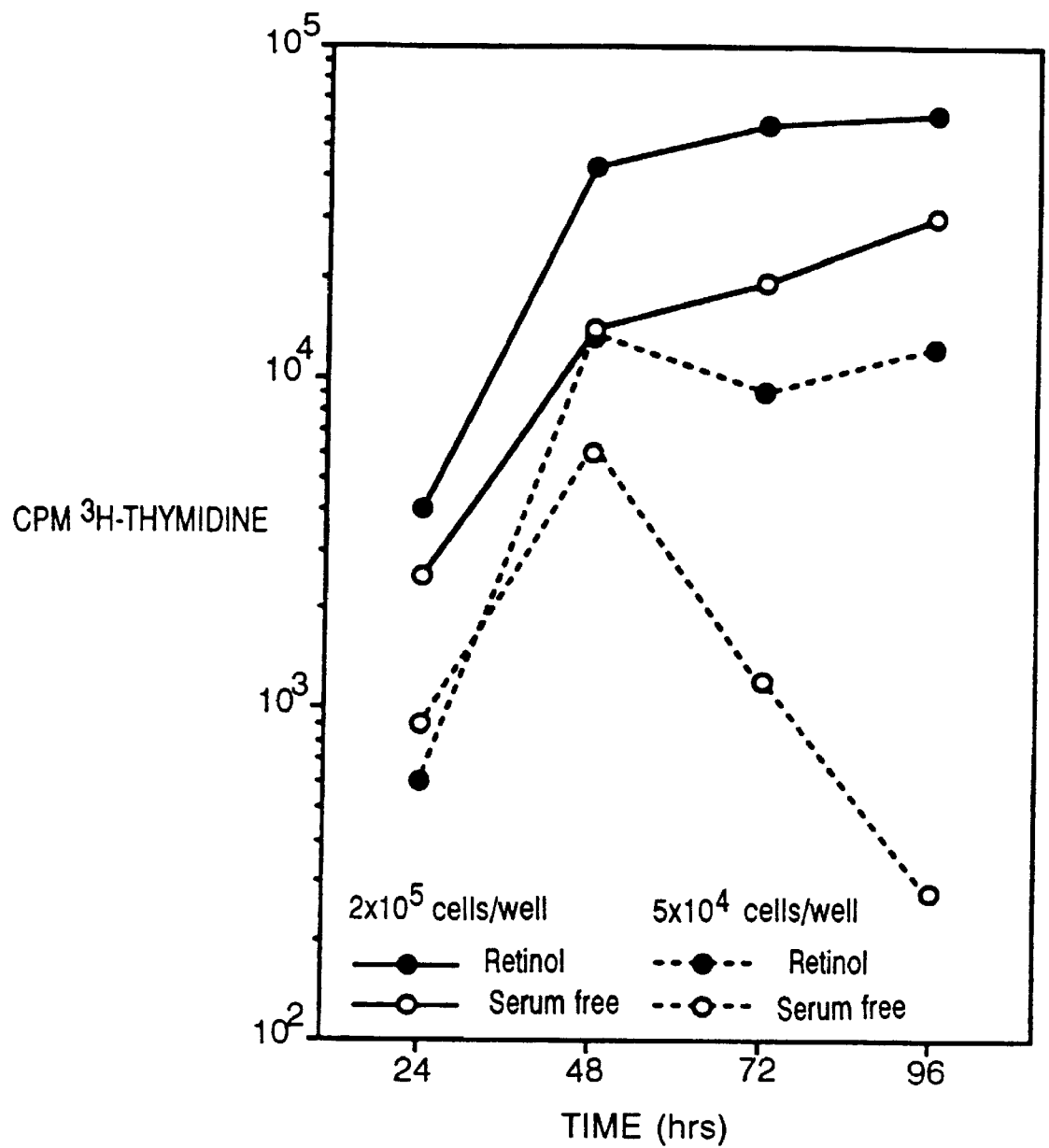

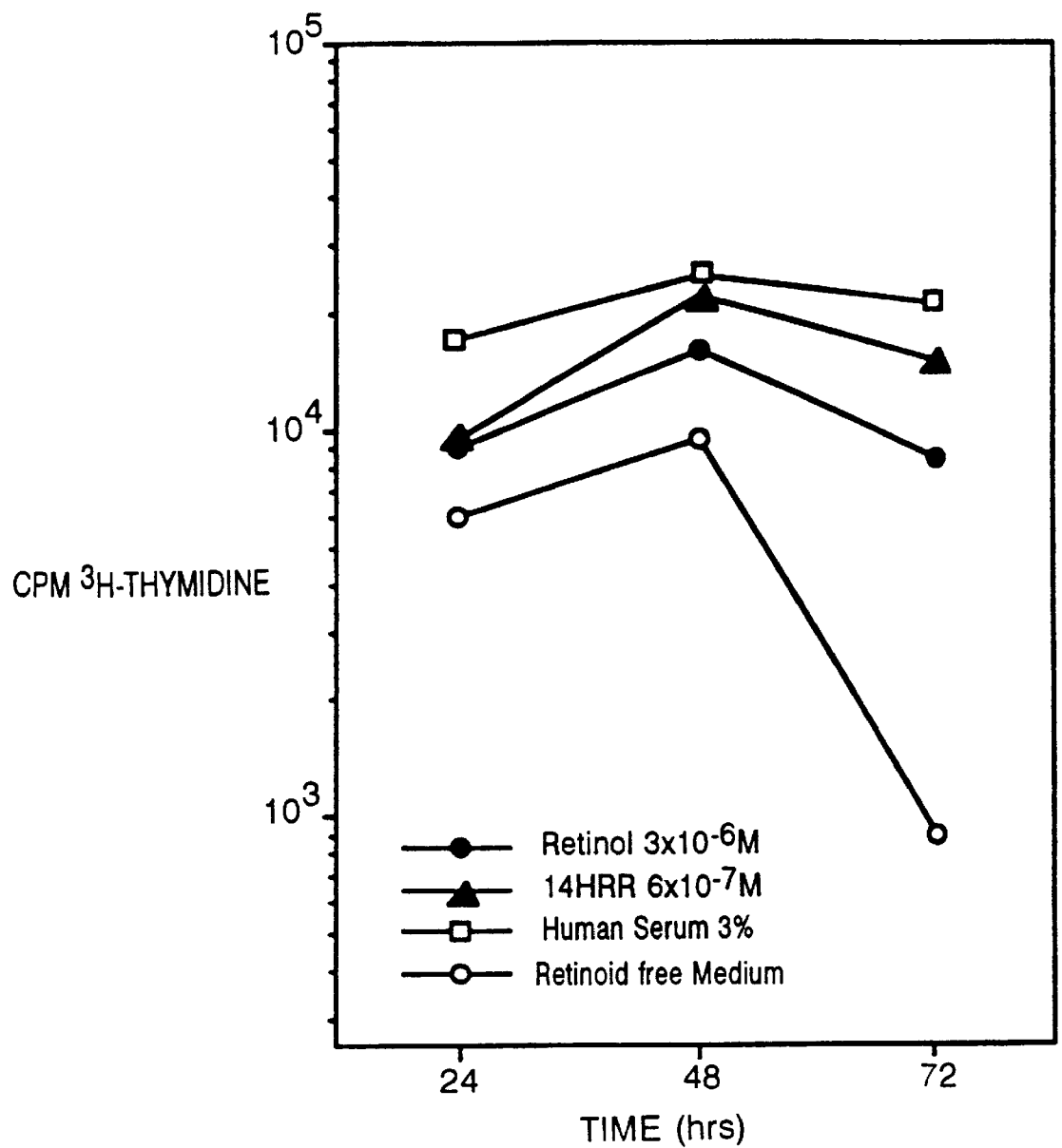

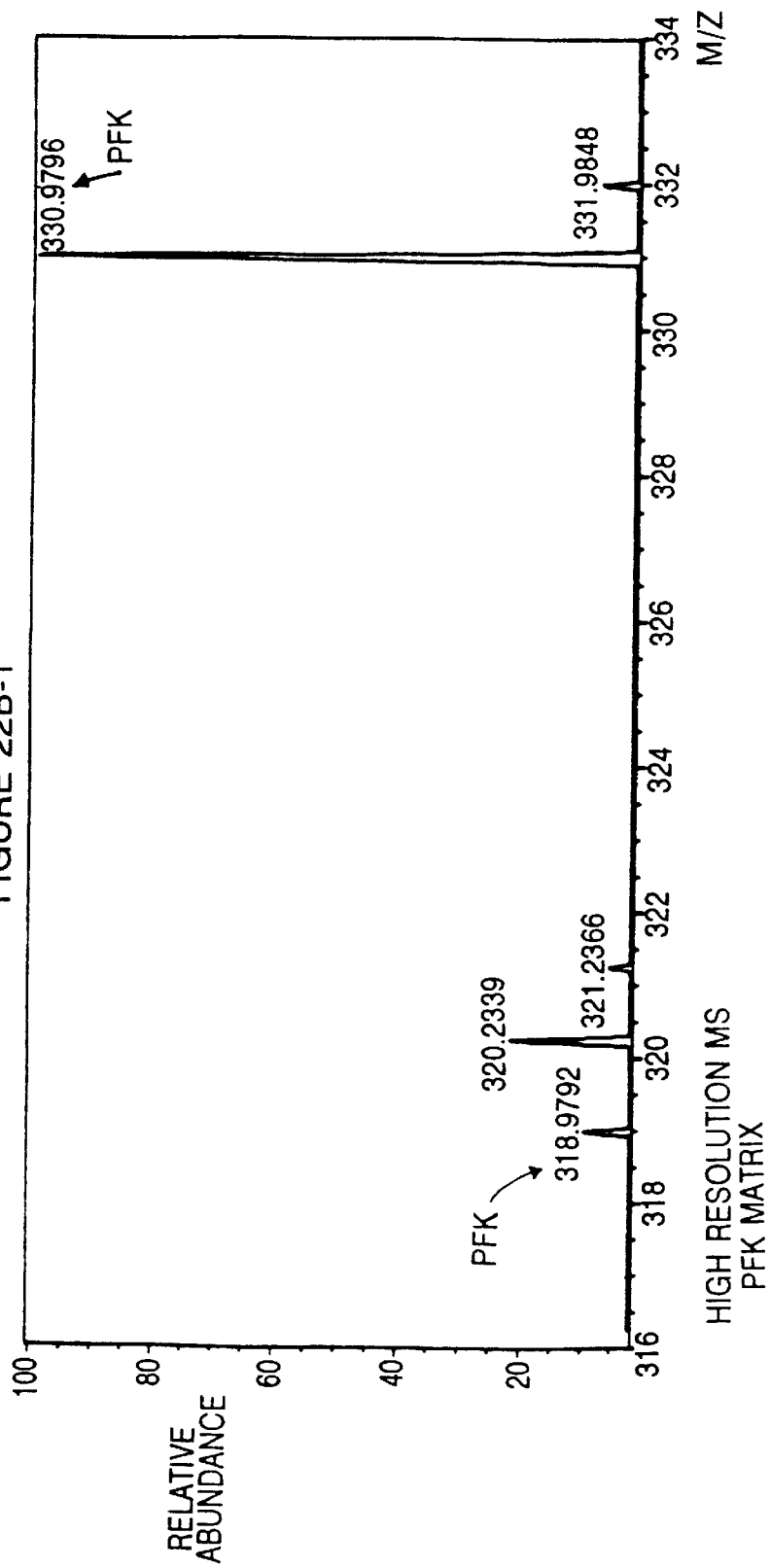
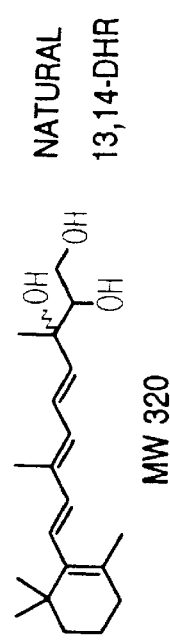
FIGURE 22B-1
FIGURE 22B-2
NATURAL 13,14-DHR
MW 320

9E

MIXTURE 9E/9Z: LESS POLAR
DIASTEREOMER
MAJOR 9E

MW 358

MIXTURE 9E/9Z; MAJOR 9E (LESS POLAR DIASTEREOMER)

9E MAJOR ISOMER (MORE POLAR DIASTEREOMERS)

9E (MAJOR ISOMER)

MW 358

E isomer

MW360

E isomer

UV (Solvent $CH_3CN$)

290.00 NM  1.1860

E isomer

MIXTURE 9E/9Z

MW 318

MIXTURE 9E/9Z

MW 320

348.00 NM 2.2286

MW 340

MW 300

RETINOL DERIVATIVES AND USES THEREOF

This application is a continuation-in-part of PCT International Application No. PCT/US92/02904, filed Apr. 9, 1992, which is a continuation-in-part of U.S. Ser. No. 682,909, filed Apr. 9, 1991, now U.S. Pat. No. 5,262,572 the contents of which are hereby incorporated by reference in this disclosure.

The invention described herein was made in the course of work under Grant Numbers CA-49933 and CA-38351 from the National Institutes of Health. The United States Government has certain rights in this invention.

BACKGROUND OF THE INVENTION

Throughout this application various publications are referenced to by arabic numerals within parenthesis. Full bibliographic citations for these references may be found at the end of the specification immediately preceding the claims. The disclosures for the publications in their entireties are hereby incorporated by reference into this application to more fully describe the state of the art to which this invention pertains.

It has long been known that dietary restriction of vitamin A causes widespread abnormalities in tissue and organ physiology, especially in neonates. The vitamin A deficiency syndrome is characterized by generally stunted growth, keratoses of skin and eyes (1) (leading in severe cases to blindness), defective testis development (1) etc., and atrophy of central (i.e., thymus and bursa of Fabrizius) and peripheral lymphoid organs. Consequently, immune functions are severely affected. Even in mild cases of vitamin A deficiency, the immune system appears to be hyporesponsive. In a recent study in southern India (2), the authors noted in children suffering from mild vitamin A deprivation significantly higher mortality rates in common childhood diseases compared with children receiving normal dietary levels of vitamin A. Since severity but not susceptibility to infection was correlated with vitamin A deprivation, it is likely that reduced immune functions are a factor.

In the absence of retinol, lymphoblastoid cells (LCL) die within 24 to 48 hours (3). Retinol and retinaldehyde, but not retinoic acid, support the growth of LCL in serum-free medium. The same is true for activated human thymocytes. These finding may represent direct correlates to the lagging development of lymphoid organs described by Wolbach and Howe (1) and the in-vivo immune system dysfunction referred to earlier (2).

Nearly all vertebrate tissues are bathed in a constant supply of vitamin A, and the ubiquitous distribution of cellular retinol-binding protein (CRBP) with its high affinity to retinol suggests that it is inside most cells as well. Yet the general purpose of retinol, its metabolism and final destination, remain for the most part unknown, the well-studied example of specialized usage such as vision notwithstanding. Since retinal is not known to be incorporated into structural parts of cells and does not bind to one of the yet analyzed transcription factors with high enough affinity, its role is more likely to be found in its function as precursor for derivatives. Use of retinaldehyde in vision is one example, and another that of retinoic acid as a morphogen (4), important for development of limb and brain. When coupled with parallel discoveries of retinoic acid receptors (RAR) (5–7) within the larger steroid receptor superfamily (8), a sound molecular foundation is given. In this hypothesis, RARs bind to specific response elements in the promoter regions of genes. Retinoic acid in turn binds to RAR, causing activation of gene transcription. The universal principle of this genetic control has increasingly been highlighted by observations that many developmentally important genes from drosophila to man are part of the retinoic acid/steroid receptor superfamily. Moreover, for more than two dozen "orphan receptors" (8) engaged in control of the general physiology of cells, the ligands are not known and are suspected to be small lipophilic molecules.

Many mammalian tissues are dependent on a source of retinol for ordered growth and development, and this requirement is also reflected in certain cell types propagated in tissue culture systems. The tissue culture medium needs to be fortified with retinol at a concentration approximating that of serum (i.a., $10^{-6}$M). It is widely believed that retinol serves as a precursor molecule for production of a number of cellular metabolites that are the true mediators of retinol effects. Examples are retinoic acids (RA, all-trans RA, and 9-cis-RA) that have been implicated in differentiation and gene regulation, respectively.

Lymphocytes also exhibit a dramatic need for retinol as a co-factor in their activation and partly for the maintenance of the proliferative state. These effects on lymphocytes are not mediated by RA. Instead the presumptive mediator has been identified as a new retinoid molecule hitherto unknown in nature that can activate certain physiological processes in lymphocytes. This compound is 14-hydroxy-4,14-retro-retinol (14-hydroxy-retro-α-retinol) (14HRR), which may work along a pathway parallel to the well established retinoic acid pathway, but leading to distinct physiological responses.

This compound is synthesized by B cells, T cells and a variety of other mammalian and insect cells. 14HRR is as active (in T cells) or 10-30 fold more active on a concentration basis in B cells as all-trans retinol. Evidently, 14HRR functions as a new type of second messenger molecules.

These findings prompted an inquiry into the biosynthetic pathway of the production of 14HRR. Based upon this inquiry, a new retinoid, previously neither observed in nature or obtained by organic synthesis, has been purified and synthesized. Its structural formula is 13,14-dihydroxy-retinol (13,14 DHR). This compound has been shown to be a metabolic intermediate in 14HRR biosynthesis and is capable of being used in lieu of retinol as a cofactor for activation and growth.

SUMMARY OF THE INVENTION

This invention provides a purified retro-retinoid compound characterized by a molecular mass of about 302 daltons. Also provided by this invention is a method of enhancing the growth of a cell in a vitamin A reduced environment which comprises contacting the cell with an effective growth enhancing amount of a compound having a structure:

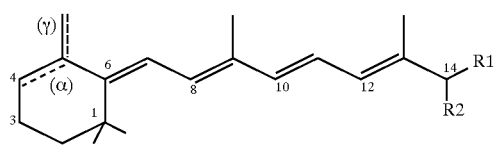

wherein the configuration of the C6, C8, C10 and C12 double bond independently is Z or E and the absolute configuration at C-14 is independently R or S; wherein R1 is alkyl, alkyl halide, alcohol, ester, ether, aldehyde, ketone, carboxylic acid, carboxylic ester, acid halide, amide, nitrile, or amine; and wherein R2 is hydroxyl, halide, alkoxy, ester, alkyl, alcohol, ether, aldehyde, ketone, carboxylic acid, carboxylic ester, nitrile, amine, azide, alkyl halide, acid halide, acid azide, or amide; or wherein R1 and R2 are replaced by a 14, 15-oxirane group; and wherein the retro structure is alpha or gamma.

This invention further provides a method for enhancing transcription of a gene regulated by retinol in a cell which comprises contacting the cell with an effective transcription-enhancing amount of a compound having the structure:

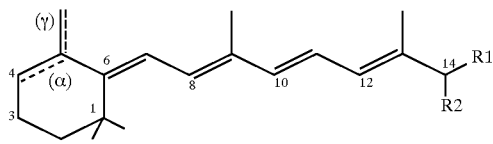

wherein the configuration of the C6, C8, C10 and C12 double bond independently is Z or E and the absolute configuration at C-14 is independently R or S; wherein R1 is alkyl, alkyl halide, alcohol, ester, ether, aldehyde, ketone, carboxylic acid, carboxylic ester, acid halide, amide, nitrile, or amine; and wherein R2 is hydroxyl, halide, alkoxy, ester, alkyl, alcohol, ether, aldehyde, ketone, carboxylic acid, carboxylic ester, nitrile, amine, azide, alkyl halide, acid halide, acid azide, or amide; or wherein R1 and R2 are replaced by a 14, 15-oxirane group; and wherein the retro structure is alpha or gamma.

A method for enhancing an immune response in a subject is also provided by this invention which comprises administering to the subject an effective immune-enhancing amount of a compound having the structure:

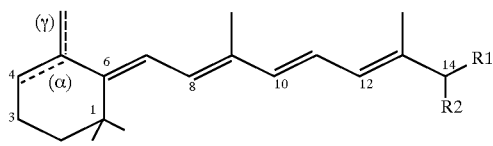

wherein the configuration of the C6, C8, C10 and C12 double bond independently is Z or E and the absolute configuration at C-14 is independently R or S; wherein R1 is alkyl, alkyl halide, alcohol, ester, ether, aldehyde, ketone, carboxylic acid, carboxylic ester, acid halide, amide, nitrile, or amine; and wherein R2 is hydroxyl, halide, alkoxy, ester, alkyl, alcohol, ether, aldehyde, ketone, carboxylic acid, carboxylic ester, nitrile, amine, azide, alkyl halide, acid halide, acid azide, or amide; or wherein R1 and R2 are replaced by a 14, 15-oxirane group; and wherein the retro structure is alpha or gamma.

The present invention also provides a purified retinoid compound characterized by a molecular mass of about 320 daltons and an atomic composition of $C_{20}H_{32}O_3$.

This invention also provides a purified retinoid compound having the structure:

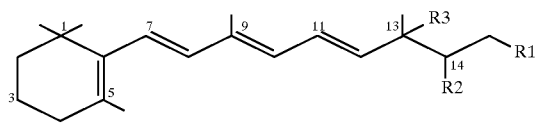

wherein the configuration of the C7, C9, and C11 double bond independently is Z or E and the absolute configuration at C13 and C14 is independently R or S; wherein R1 is alkyl, alkyl halide, alcohol, ester, ether, aldehyde, ketone, carboxylic acid, carboxylic ester, acyl halide, amide, nitrile, or amine; R2 and R3 are independently hydroxyl, halide, alkoxy, ester, alkyl, alcohol, ether, aldehyde, ketone, carboxylic acid, carboxylic ester, nitrile, amine, azide, alkyl halide, acid halide, acid azide, or amide; or wherein R2 and R3, or R1 and R2 are replaced by a 13,14-oxirane or a 14,15-oxirane group, respectively.

This invention also provides a pharmaceutical composition which comprises the purified retinoid compound described directly above or alternatively, a synthetic product of the compound, and a pharmaceutically acceptable carrier.

The present invention also provides a growth medium comprising the compound directly above at a concentration effective to enhance cell growth.

Also provided by the present invention is a method of enhancing the growth of cells in culture which comprises culturing the cells in the growth medium above.

This invention further provides a method of enhancing the growth of a cell which comprises contacting a cell with an effective growth enhancing amount of the compound directly above.

In addition, this invention provides a method for enhancing an immune response which comprises administering to the subject an effective immune-enhancing amount of the compound directly above.

This invention also provides a method for enhancing transcription of a gene regulated by retinoids in any cell which comprises contacting the cell with an effective transcription enhancing amount of the compound directly above.

The present invention also provides a process for synthesizing the compound having the structure:

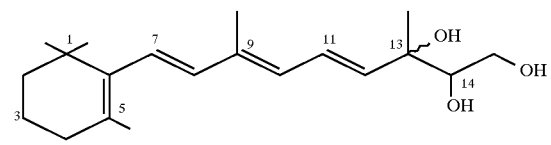

which comprises:

(a) contacting a compound having the structure:

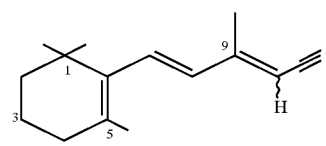

under suitable conditions with a compound having the structure:

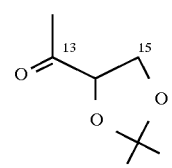

to form a compound having the structure:

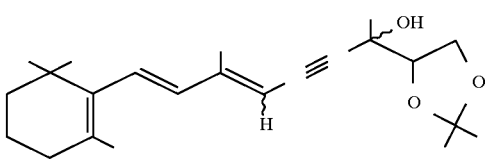

(b) reacting the compound found in step (a) under suitable conditions to form a compound having the structure:

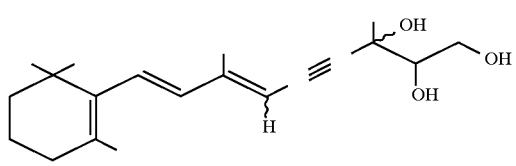

(c) reacting the compound formed in step (b) under suitable conditions to form the compound having the structure:

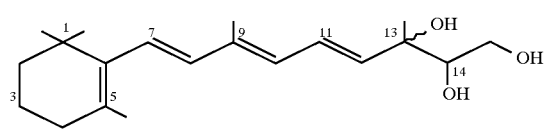

The present invention also provides a compound having the structure:

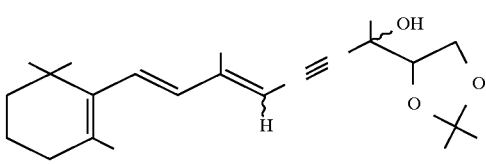

The present invention further provides a compound having the structure:

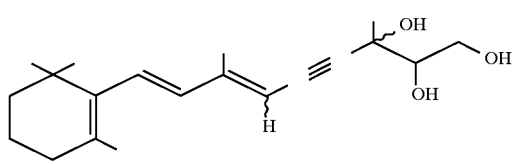

In addition, the present invention provides a method for obtaining the purified retinoid compound described hereinabove which comprises growing a suitable cell line under suitable conditions, contacting the grown cells with retinol to form a cell pellet, extracting the cell pellet or the culture fluid with a suitable organic solvent, and purifying the retinoid compound from the organic phase by HPLC column chromatography, wherein the retinoid compound elutes on a C-18 column (Vydac) at 81% methanol/19% water.

The present also invention provides a pharmaceutical composition which comprises 14-hydroxy-4,14-retro-retinol and a retinol binding protein.

Also provided by this invention is a compound having the structure:

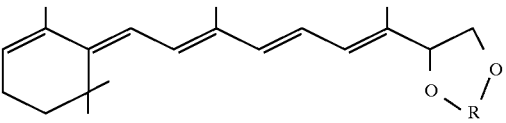

wherein R is $C(Me)_2$ or $Si(tButyl)_2$.

The present invention further provides a compound having the structure:

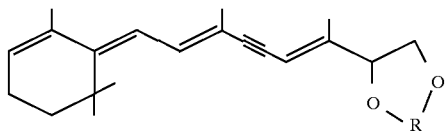

wherein R is $C(Me)_2$ or $Si(tButyl)_2$.

The present invention still further provides a compound having the structure:

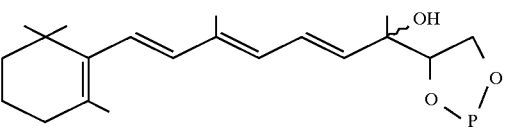

wherein R is $C(Me)_2$ or $Si(tButyl)_2$.

Lastly, the present invention provides a compound having the structure:

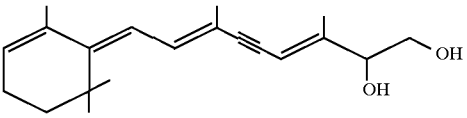

4 liters of HB101 medium were conditioned overnight with 400,000 LCL 5/2 cells/ml in HB101 medium. The medium proteins were precipitated with 80% ammonium sulfate. The proteins were freeze-dried and delipidated with ether/ethanol. 5/2 cells (1000/well) were incubated for 72 hours in HB101 medium with the indicated amounts of delipidated protein and extracted lipids. DNA synthesis was measured by [$^3$H]-thymidine uptake. The measurements were done in triplicate.

Figure 2A:
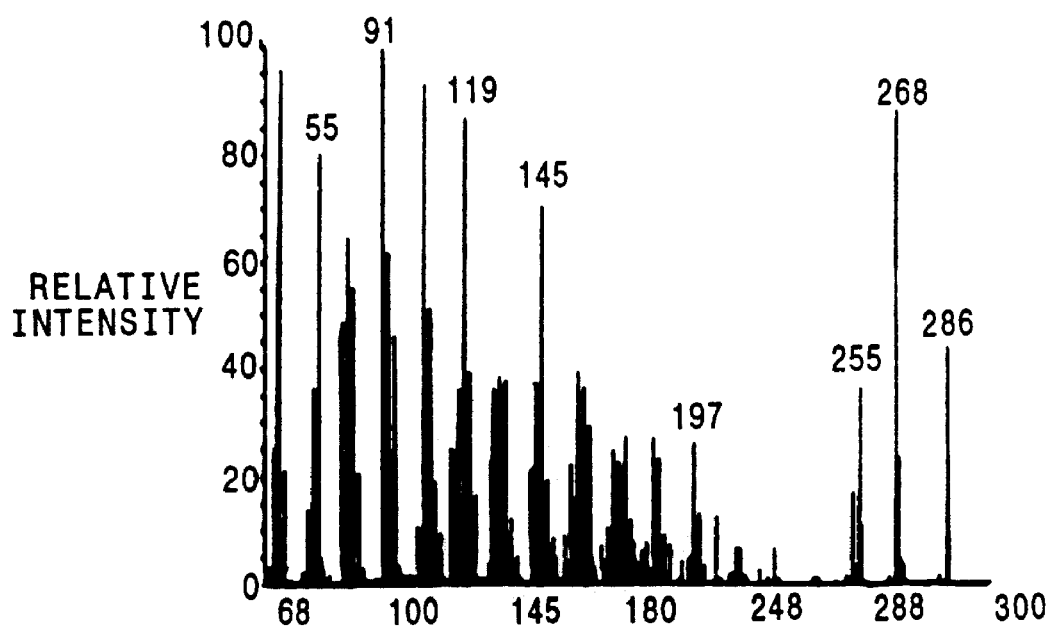

FIG. 2A. EI mass spectrum of bioactive lipid in human serum.

Figure 2B:
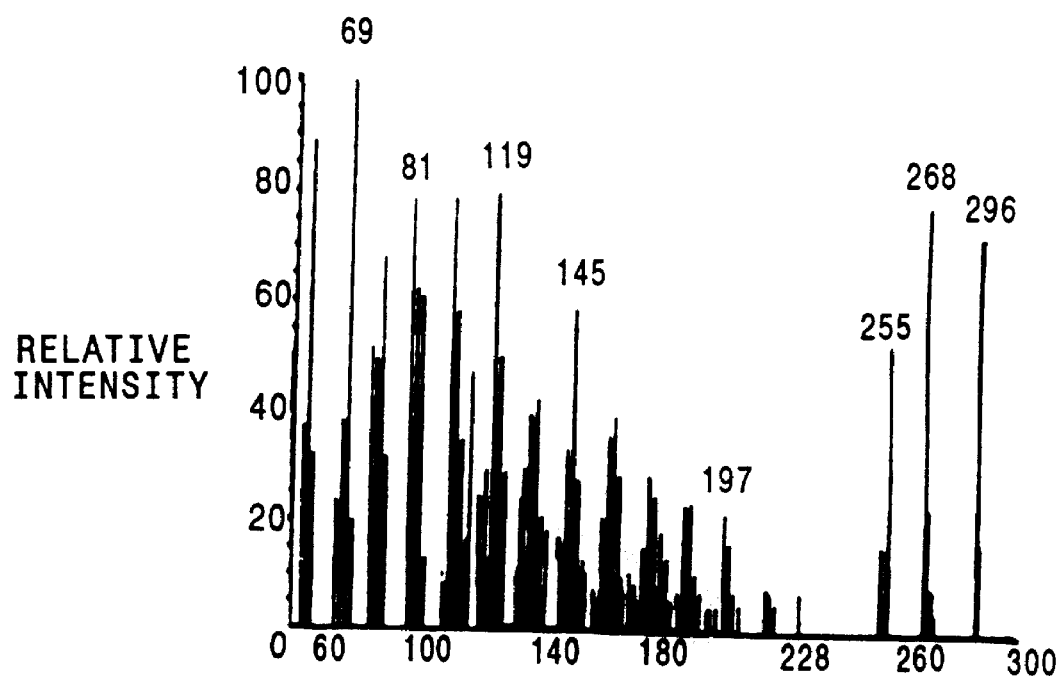

FIG. 2B. EI mass spectrum of all-trans retinol from the National Bureau of Standards Library.

Figure 3:
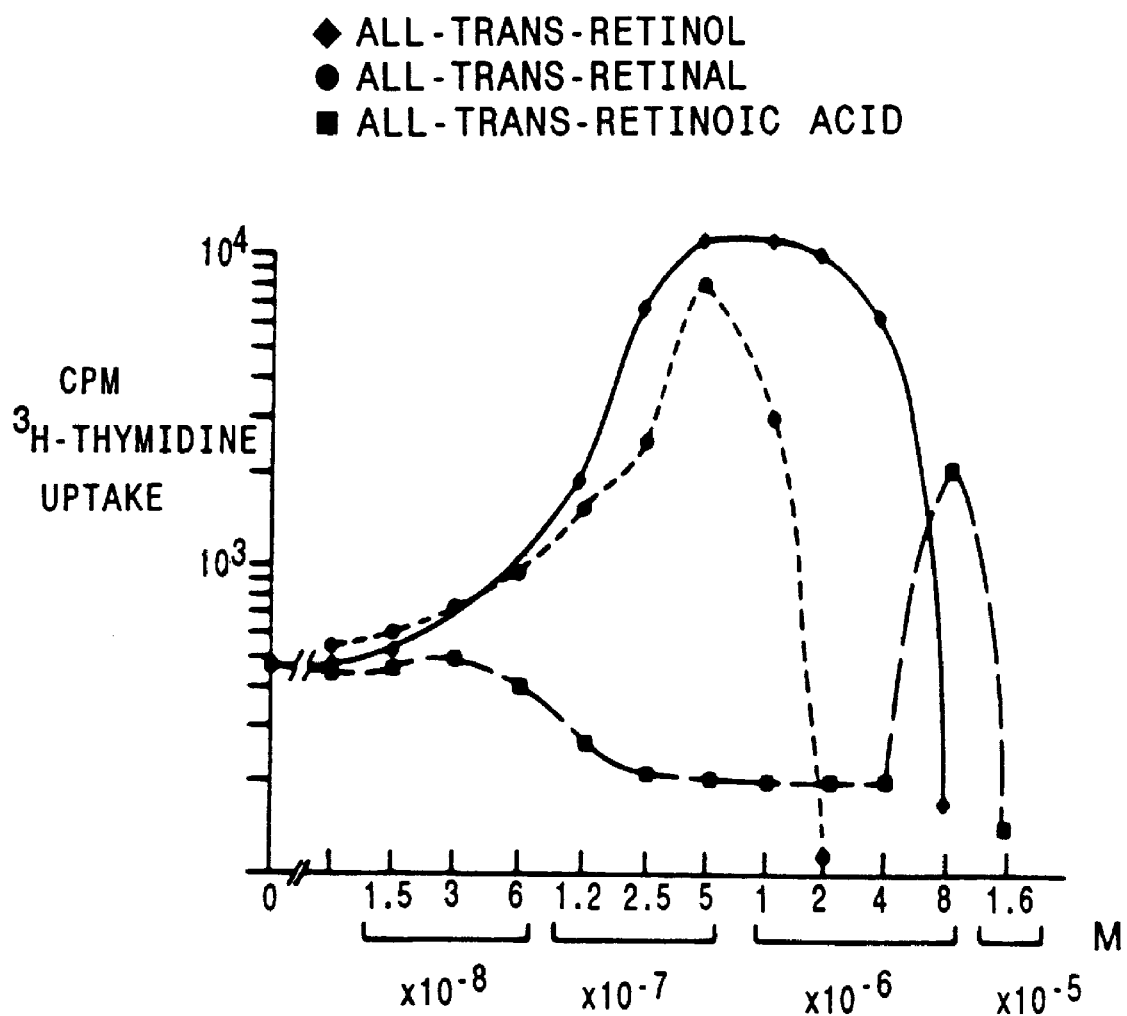

FIG. 3. The dose-response curves of different retinoids to stimulate the growth of 5/2 cells in culture.

Washed 5/2 cells (5,000/well) were incubated for 72 hours in HB101 medium with the indicated amounts of retinoids. DNA synthesis was measured by [$^3$H] thymidine uptake. The measurements were done in triplicate. The SDs were <15%.

FIG. 4A through 4D. Retinol but not synthetic retinoic acid analogs enable 5/2 cells to grow.

Figures 1, 4A:
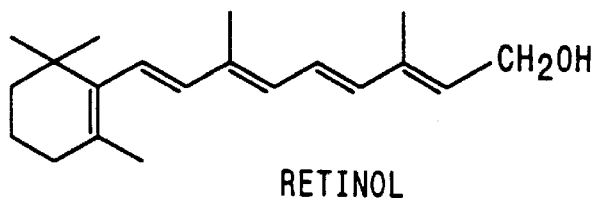

FIG. 4A. The chemical structures of retinoids used.

Figures 2, 4A:
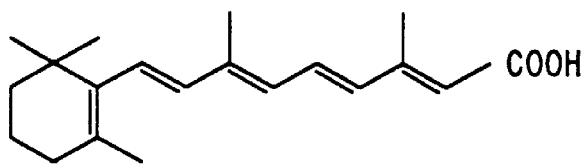
Figures 3, 4A:
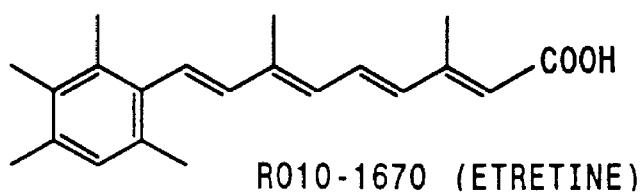
Figures 4, 4A:
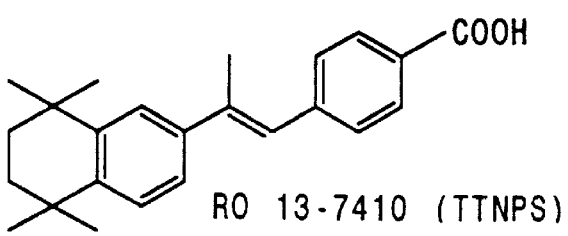
Figures 4, 4A, 5:
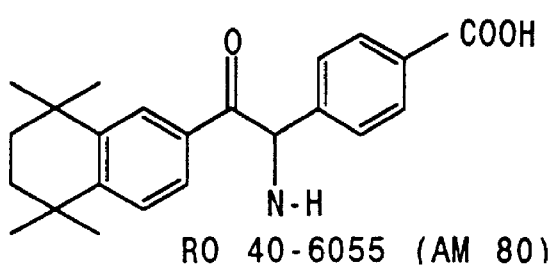
Figure 4B:
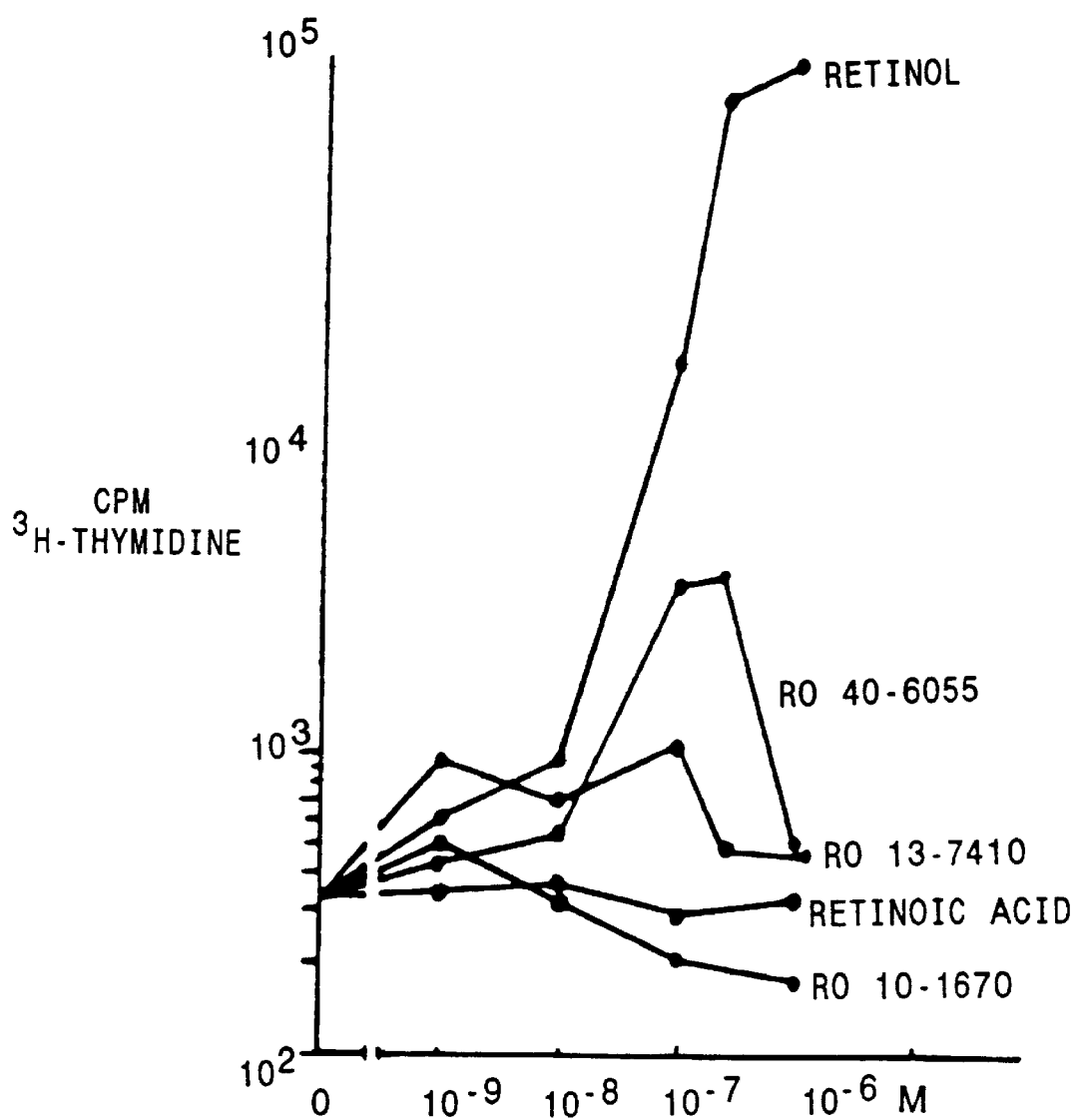

FIG. 4B. The dose-response curves measured on day 3.

Figure 4C:
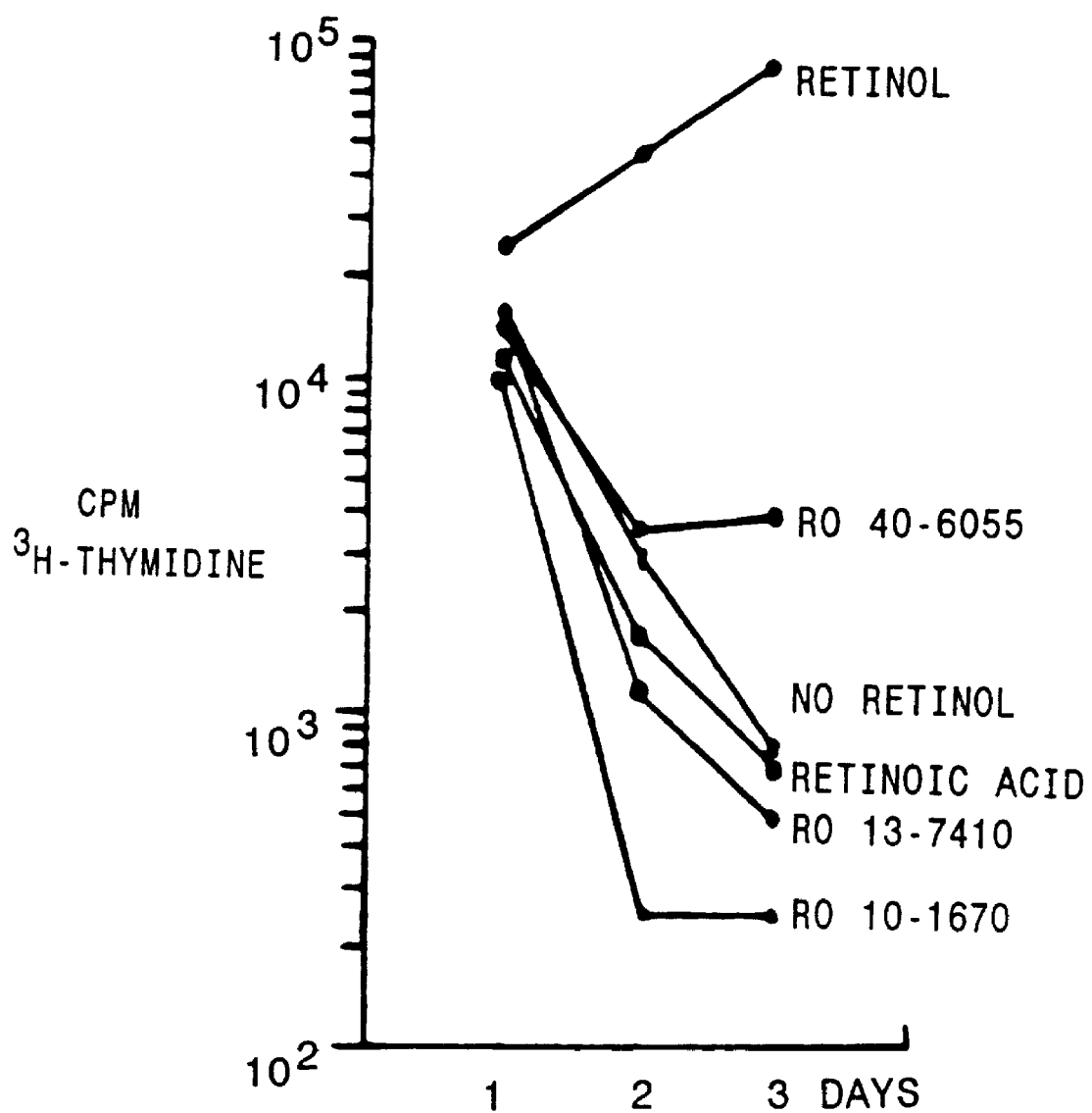

FIG. 4C. The effect of $3\times10^{-7}$M retinoids measured day 1, 2 and 3.

Figure 4D:
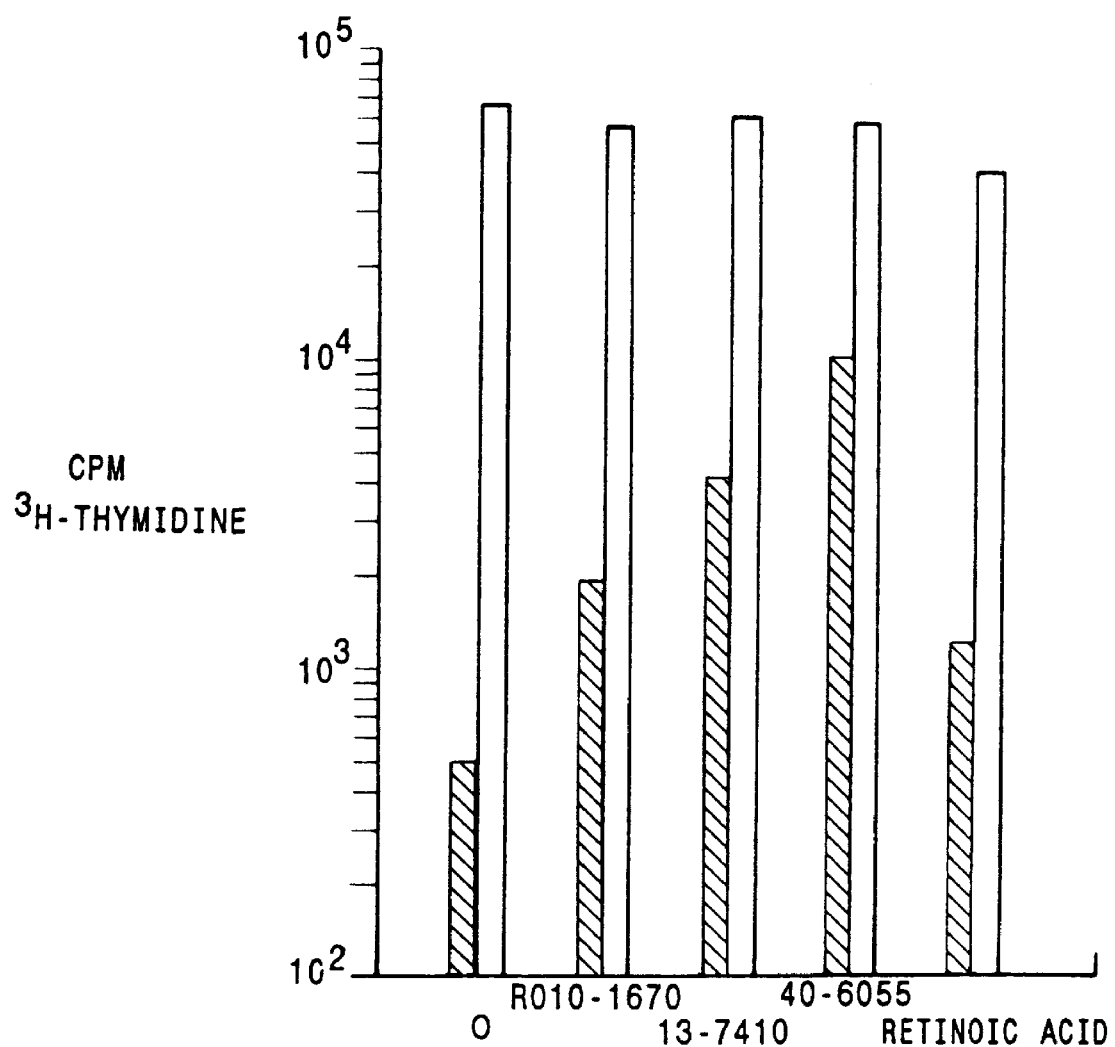

FIG. 4D. The combination of retinoic acid analogs ($3\times10^{-7}$M) with and without $10^{-6}$M retinol measured on day 3.

In FIGS. 4B to 4D, 5/2 cells were washed twice and seeded at a concentration of 150,000 cells/ml in HB 101 medium. Triplicate samples of 100 μl of cell suspension were removed daily and pulsed for 6 hours with [$^3$H] thymidine. Means are shown. The SDs were never >20%.

FIGS. 5A through 5D. Retinol deprivation leads to cell death.

5/2 cells were washed once and seeded at a density of 300,000/ml in HB 101 medium with and without $10^{-6}$M retinol. The trypanblue-negative (FIG. 5A) and trypanblue-positive (FIG. 5B) cell number of nine aliquots was determined every 24 hours. Means+SDs are shown. In a repeat experiment cells were stained with Wright-Giemsa stain after 40 hours of culture.

Figure 5A:
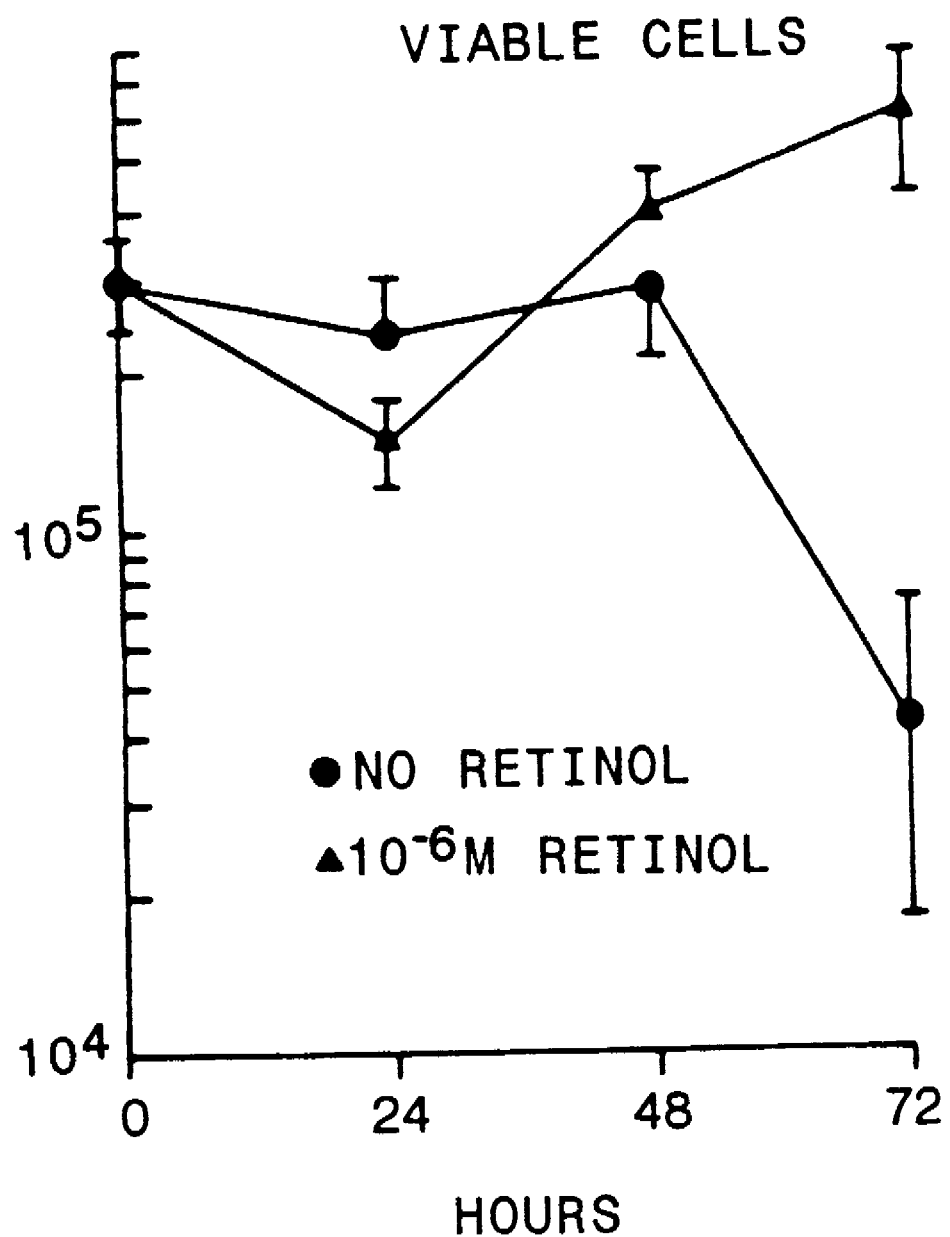
Figure 5C:
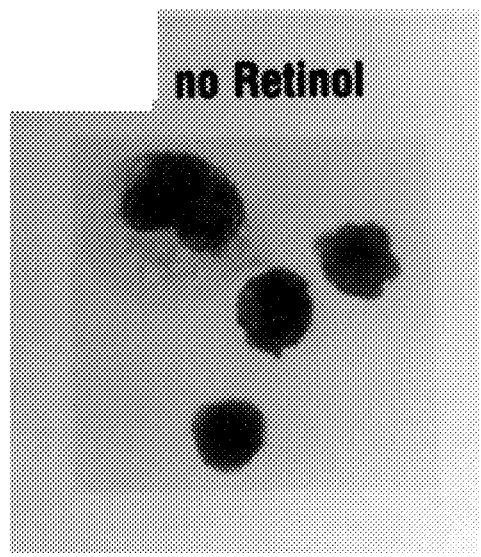

FIG. 5C. Shows cells without retinol.

Figure 5D:
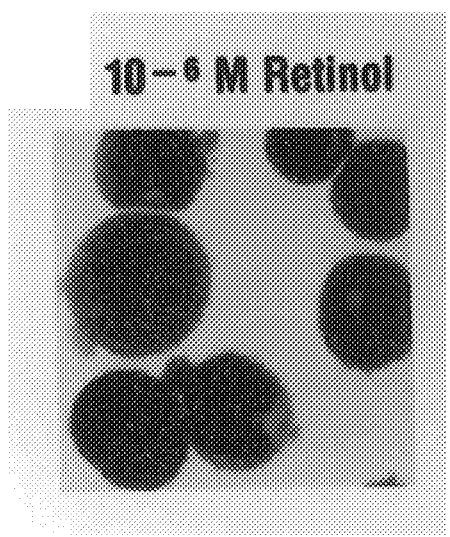

FIG. 5D. Shows that cells with $10^{-6}$M retinol.

Figure 6A:
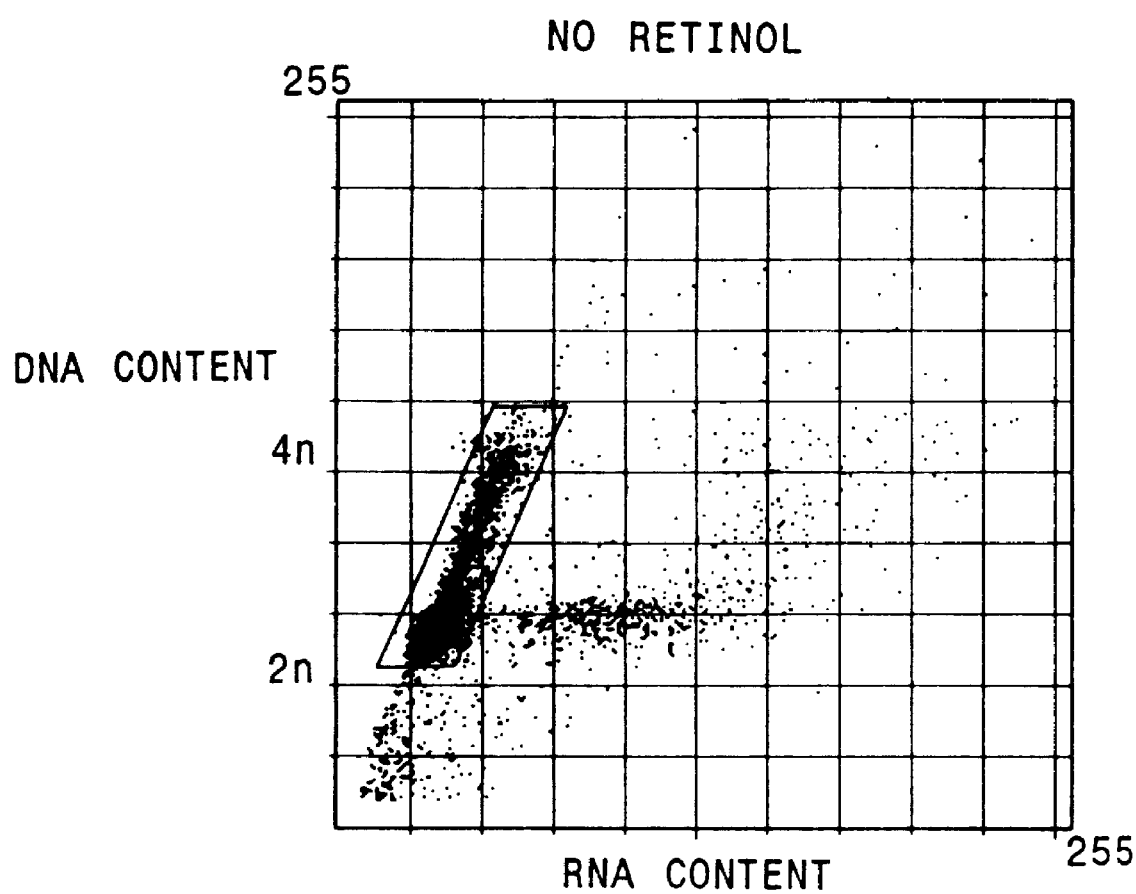
Figure 6B:
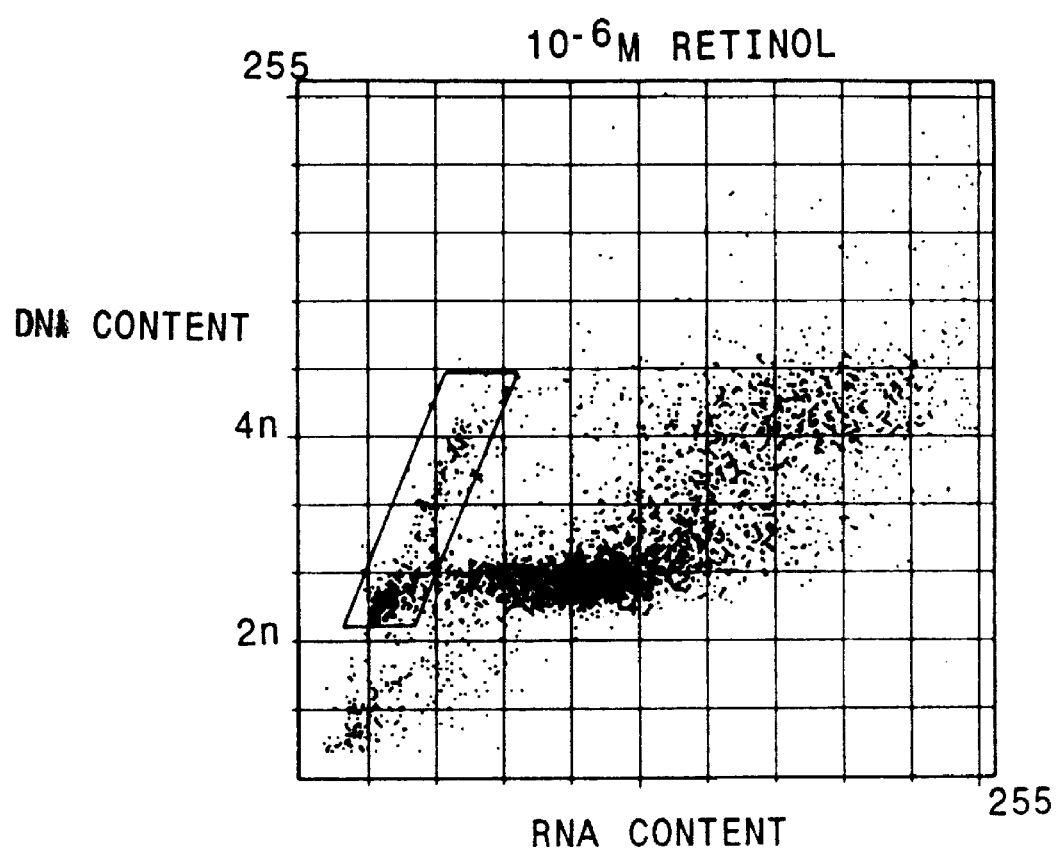

FIGS. 6A and 6B. Effect. Shows that effect of retinol-deprivation on RNA and DNA content of 5/2 cells.

5/2 cells were washed and seeded at a density of 50,000/ml in HB 101 without (FIG. 6A) and with (FIG. 6B) $10^{-6}$M retinol. After 48 hours, the cells were stained with acridine orange and 5,000 cells/sample were analyzed by flow cytometry. Scattergrams represent distribution of cells with respect to their DNA and RNA content. 2n corresponds to diploid, 4n to tetraploid DNA content. The boxed dots with very low RNA content correspond to nuclei.

Figure 7:
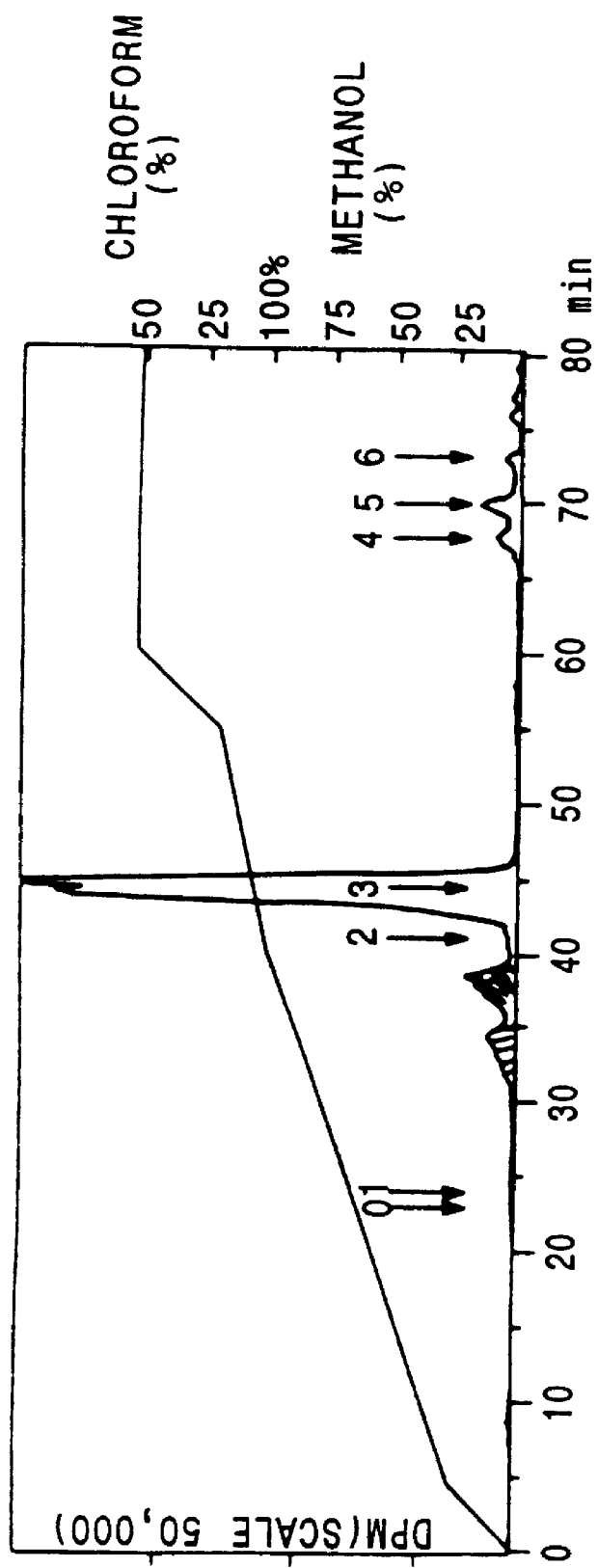

FIG. 7. Shows retinol metabolites in 5/2 cells.

5/2 cells ($10^6$ cells in 10 ml HB 101 medium) were incubated with all-trans-[$^3$H] retinol (10 uCe/ml). After 24 hours, retinoids were extracted from the washed cell pellet and unlabeled marker retinoids were added. The crude extract was loaded on an analytical reversed-phase C-18 column. Retinoids were eluted with the shown linear gradient of water/methanol/chloroform. The flow rate was 0.5 ml/min. DPM were determined with an on line scintillation counter. Reference retinoids were the all-trans forms of 0: 3,4-didehydroretinoic acid, 1: all-trans-retinoic acid, 2: 3,4-didehydroretinol, 3: retinol, 4: retinyl linoleate, 5: retinyl oleate, 6: retinyl palmitate. Shaded area corresponds to P3. Cross-hatched area corresponds to P1.

Figure 8:
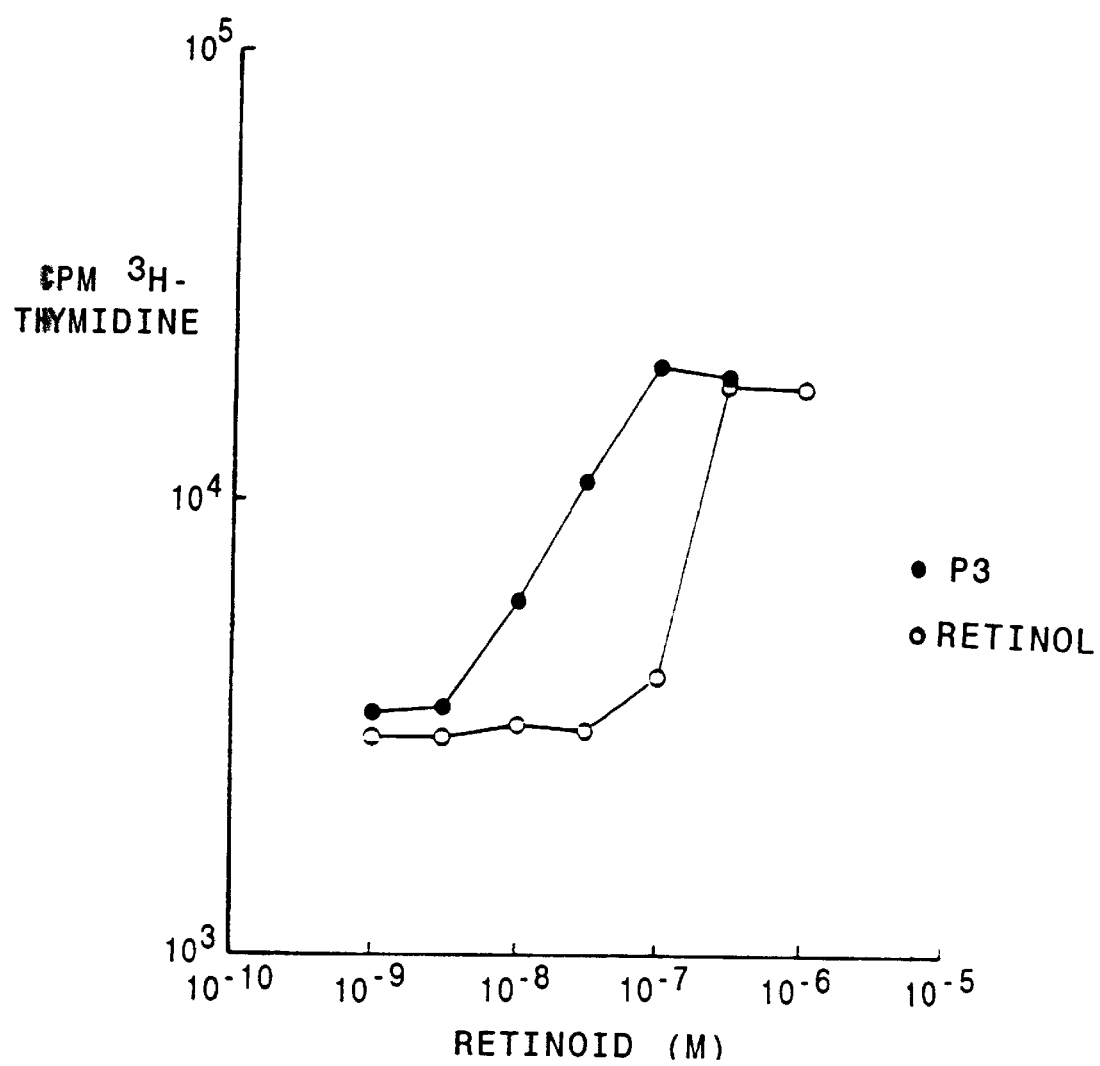

FIG. 8. Shows the dose-response curve of P3 and retinol.

P3 was purified as described in the Experimental Details section. 5/2 cells (5,000/well) were incubated for 72 hours in HB101 medium and refed with the indicated amount of retinoid daily. DNA synthesis was measured by [$^3$H]-thymidine uptake. P3 is bioactive down to a concentration of $10^{-8}$M (FIG. 8). It is 10 to 15 times more potent than retinol, but unlike with retinol, cultures have to be replenished daily with P3. This is due either to chemical instability or to a more rapid metabolic degradation of P3 by the cells.

The use of $^3$H retinol bound to fetal calf serum was used as an assay to test for P3 in other cell lines. All 26 mammalian cells tested results of 13 cells lines shown in Table 1, radioactivity peak at the position where P3 normally elutes. In the instances tested, the material in this peak also showed the characteristic UV spectrum of P3.

Figure 9A:
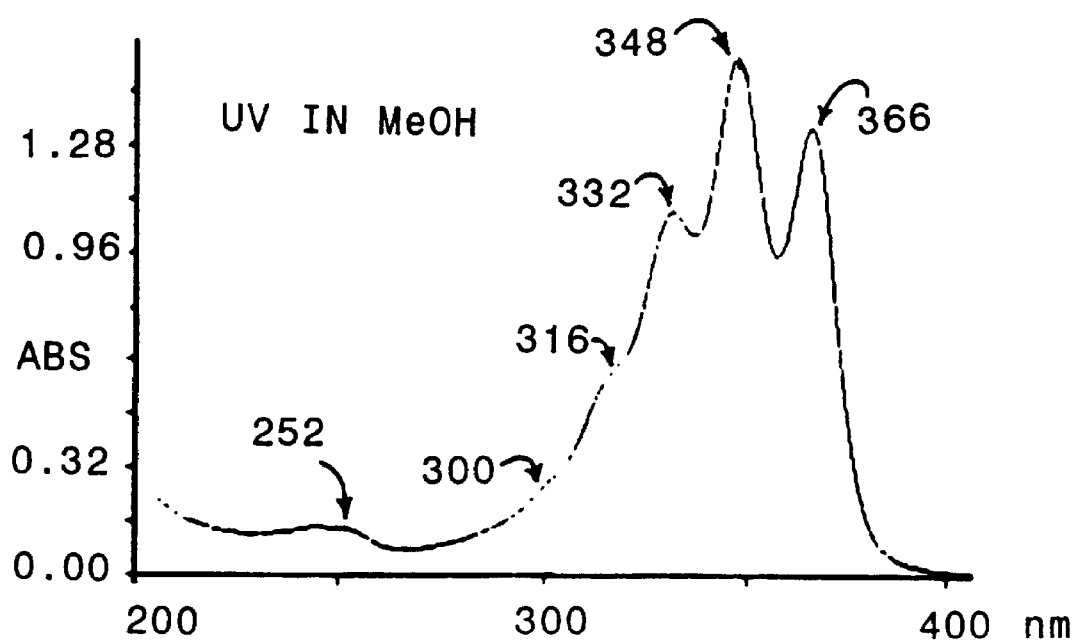
Figures 1, 9B:
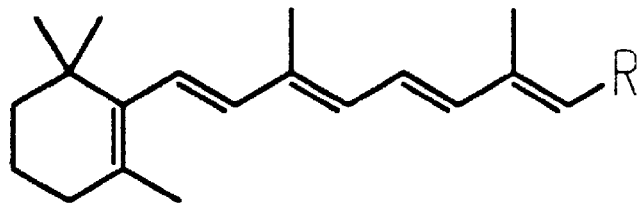
Figures 2, 9B:
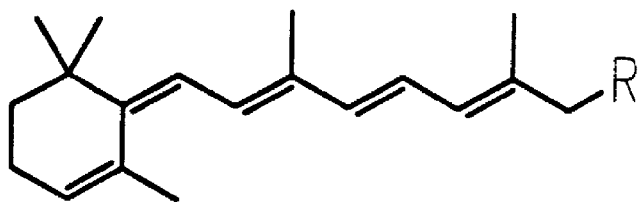
Figures 3, 9B:
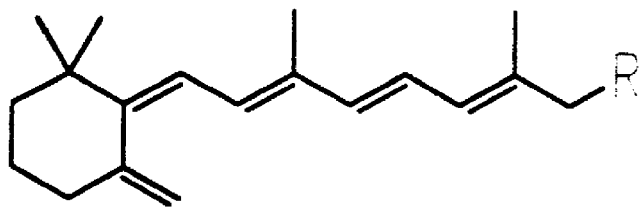

FIGS. 9A and 9B-1 through 9B-3 Effect. Shows the absorption spectrum of P3 in methanol, measured on the Perkin-Elmer Model Lambda 4B UV/VIS spectrophotometer. P3 has a λmax at 348 nm, a vibronic fine structure at 366, 332, 316 and 300 nm, and a weak absorption at 252 nm. Retinoids show a fine structure in their absorption spectra when the molecule adopts a ring/side-chain planar geometry, either imposed by protein/retinoid interaction as in the retinol/CRBP complex or (9) by a retro-configuration of the double bond system as shown in FIG. 9B (10,11). Since P3 maintains its fine structure after the lipid/protein separation, protein/retinoid interaction are excluded.

Figure 10A:
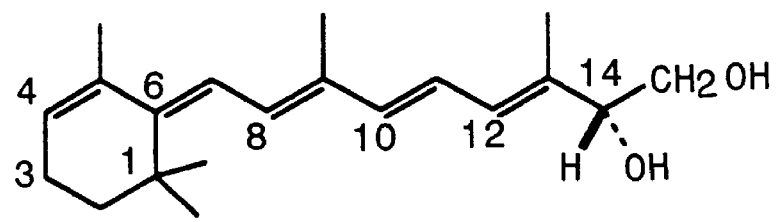
Figure 10B:
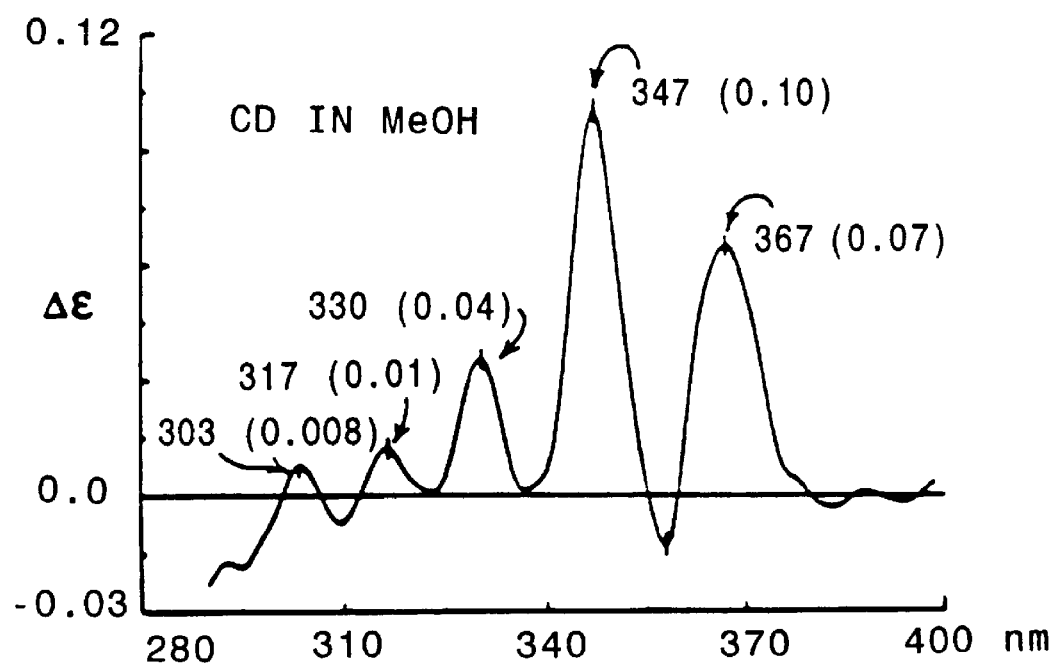

FIGS. 10A and 10B. Shows circular dichroism spectrum of P3 on the Jasco J-720 spectropolarimeter. The CD spectrum of P3 exhibits a positive Cotton effect and fine structure. This confirms the presence of an assymeric center. The absolute configuration at C-14 is assigned as R on the basis of the positive Cotton effects associated with respective fine structured UV absorption, i.e., "allylic Hydroxyl effect" (14, 15, 16). However, since this interpretation is dependent on the perturbation of the pentane absorption at 348 nm by the hydroxyl group, ca. 200 nm (remote from 348 nm), and furthermore, since an additional 15-OH group is present, the configuration at C-14 needs to be confirmed by ongoing synthesis.

Figure 11A:
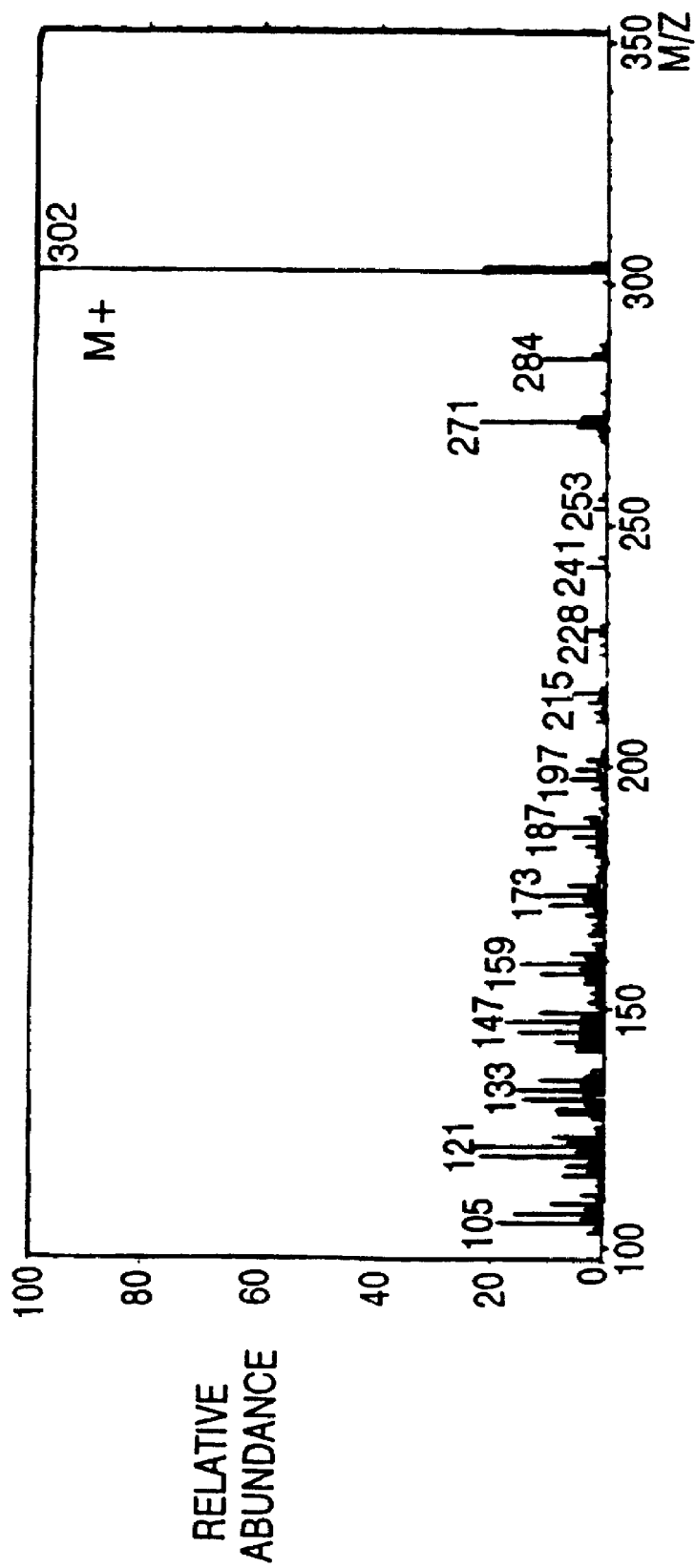

FIG. 11A. Shows the low resolution EI mass spectrum of P3, measured on JEOL DX-303 HF.

Low resolution EI/MS of P3 measured on JEOL DX-303 HF m/z 302 (M+ 100), 284 (11; M—H$_2$O), 271 (23; M—CH$_2$OH), 253 (2), 241 (4), 228 (4), 215 (6), 197 (6), 187 (9), 173 (10), 159 (15), 147 (17), 133 (15), 121 (23), 105 (20). The low resolution mass spectrum indicates the presence of a single compound with a molecular mass of 302 daltons.

Figure 11B:
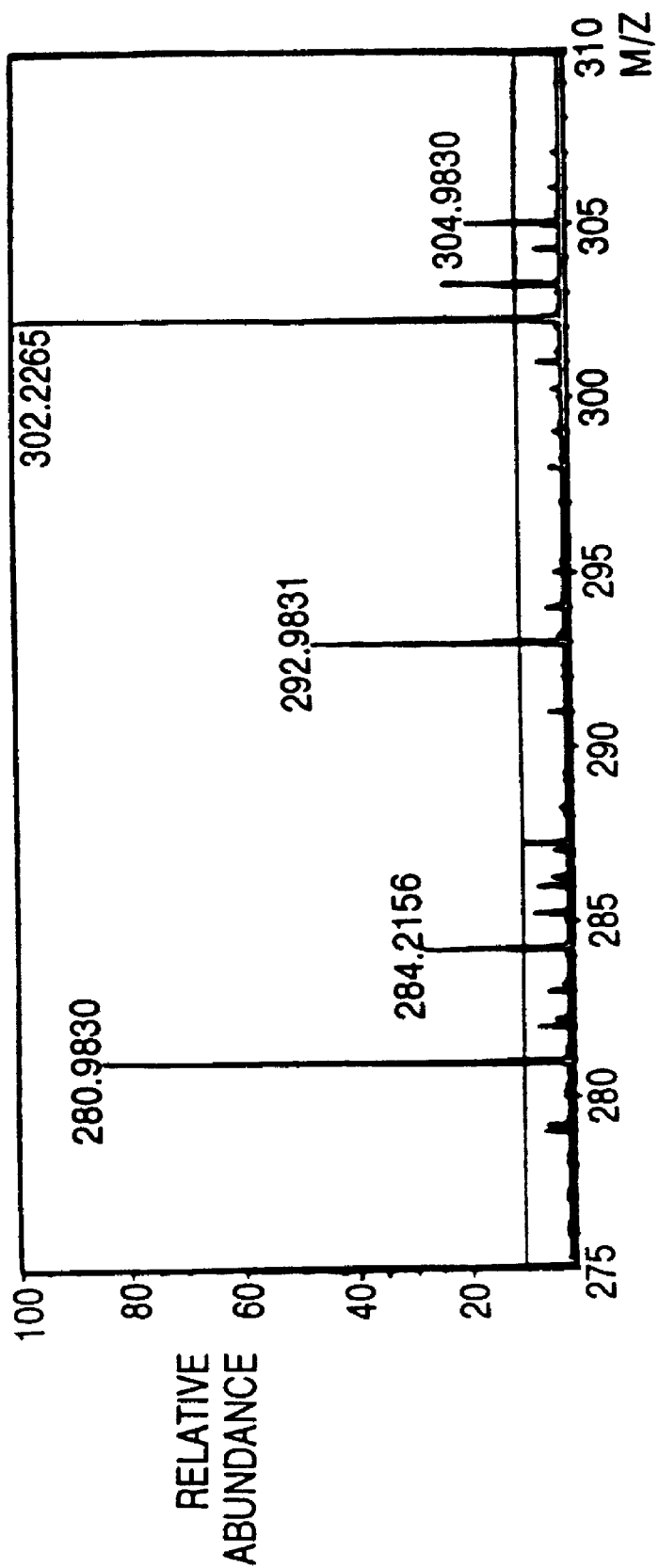
Figure 12A:
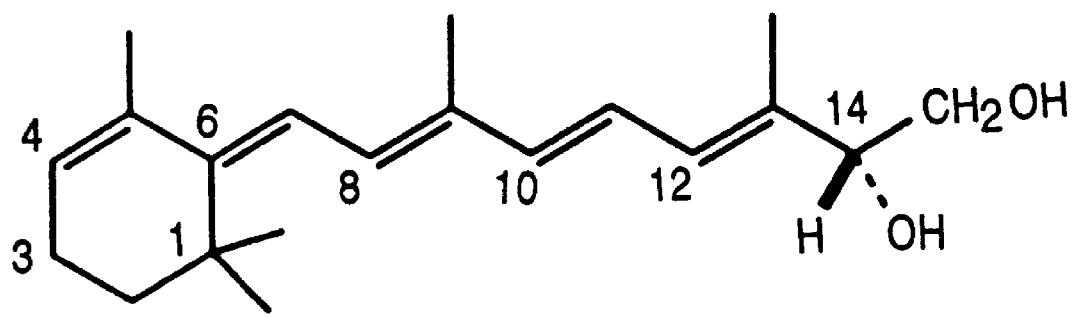
Figure 12B:
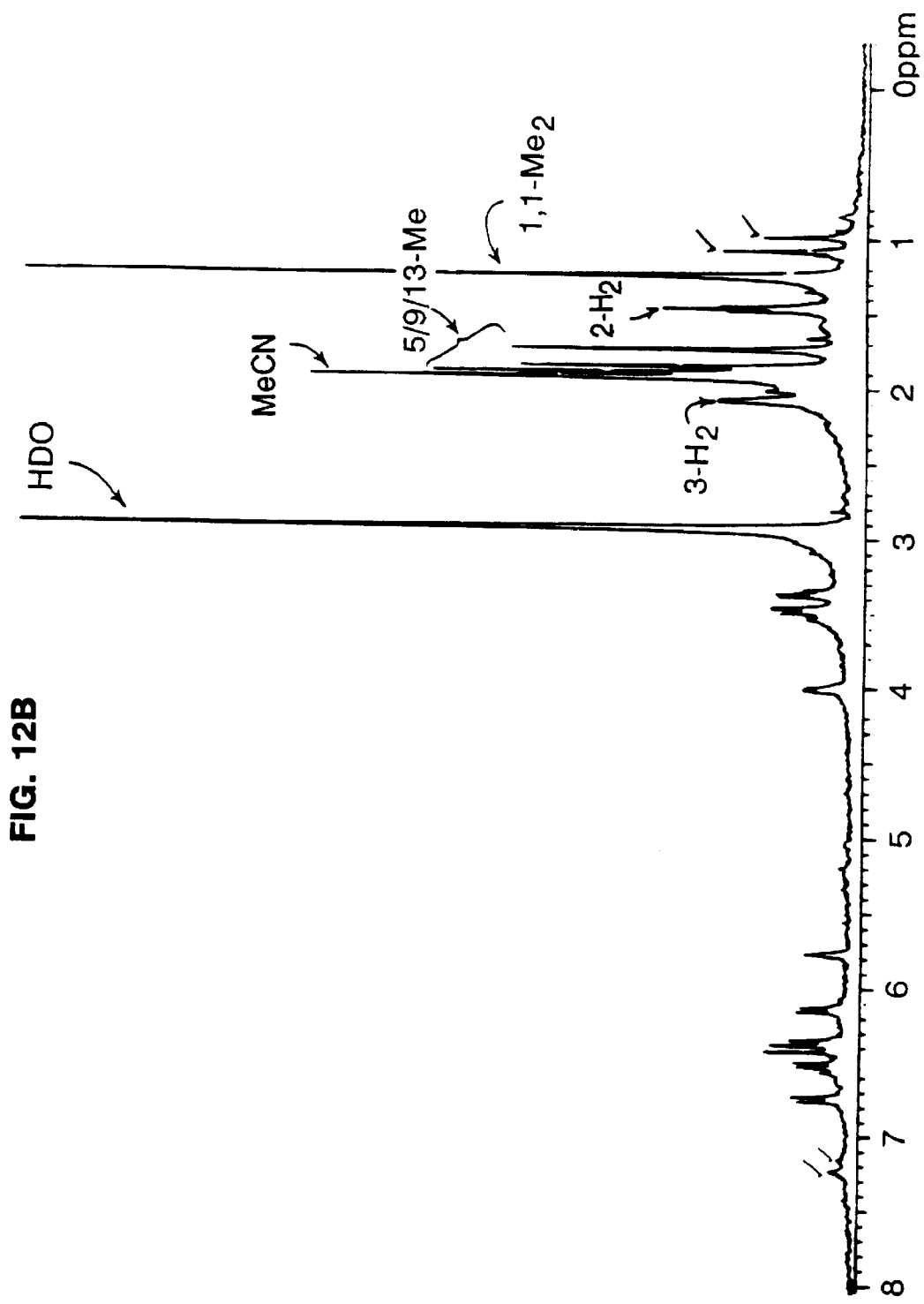
Figure 12C:
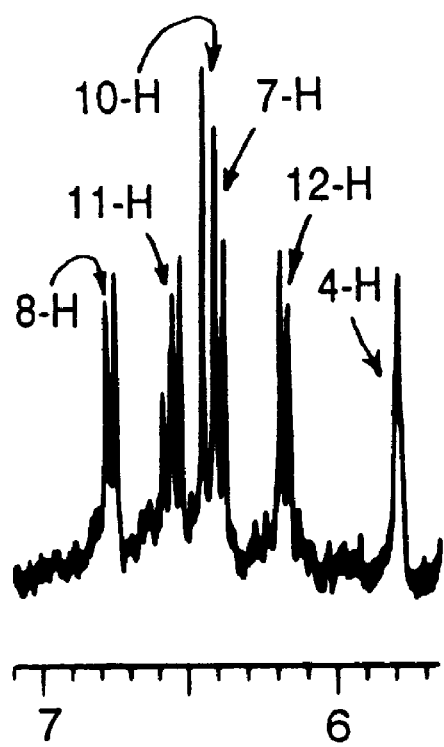
Figure 12D:

FIG. 11B. Shows the high resolution EI/MS (matrix PFK). The observed mass of 302.2265 (calc. 302.2246) is consistent with an atomic composition of $C_{20}H_{30}O_2$. This means that P3, which has a retro structure skeleton as suggested by absorption spectroscopy, possesses an additional oxygen atom as compared to its precursor retinol.

FIGS. 12A through 12D. Shows proton NMR studies that established that P3 is a 14-hydroxy-4,14-retro-retinol (or 14-hydroxy-retro-α-retinol, 14HHR).

$^1$H NMR (CD$_3$CN, one drop D$_2$O, VARIAN VXR-400) ∂1.30 (s, 6H, 1,1-Me$_2$), 1.50 (t,J 7.5 Hz, 2H, 2-H$_2$), 1.76/1.87/1.90 (s, all 3H, 5/9/13-Me), 2.08 (m, 2H, 3-H2), 3.4 (m, 1H, 15-H), 3.5 (m, 1H, 15-H), 4.02 (m, 1H, 14-H) (see insert B, in C$_6$D$_6$, for better resolution). Olefinic protons (Insert A): 5.79 (t, J 4 Hz, 1H, 4-H), 6.17 (d, J 12 Hz, 1H, 12-H), 6.38 (d, J 12.3 Hz, 1H, 7-H), 6.42 (d, J 17 Hz, 1H, 10-H), 5.56 (dd, J 17, 12 Hz, 1H, 11-H), 6.76 (d, J 12.3 Hz, 1H, 8-H). Checked peaks arise from 14-HRR degradation.

The 6–7 double bond configuration was established as E by comparing the chemical shifts of 1,1-Me$_2$ (1.30) and 4-H (5.79) with those reported for 6-E-4,14-retro-retinyl acetate (17) 1.28 and 5.76, respectively. The corresponding values for 6-Z-4,14-retro-retinyl acetate are 1.11 and 5.63 ppm. Furthermore the 6-E configuration was confirmed by observation of a ca. 4% NOE between 1,1-Me$_2$ and 8-H. The configuration of the 12–13 double bond, although tentatively depicted as E in the structure, is uncertain; this will be confirmed by synthesis.

Figure 13:
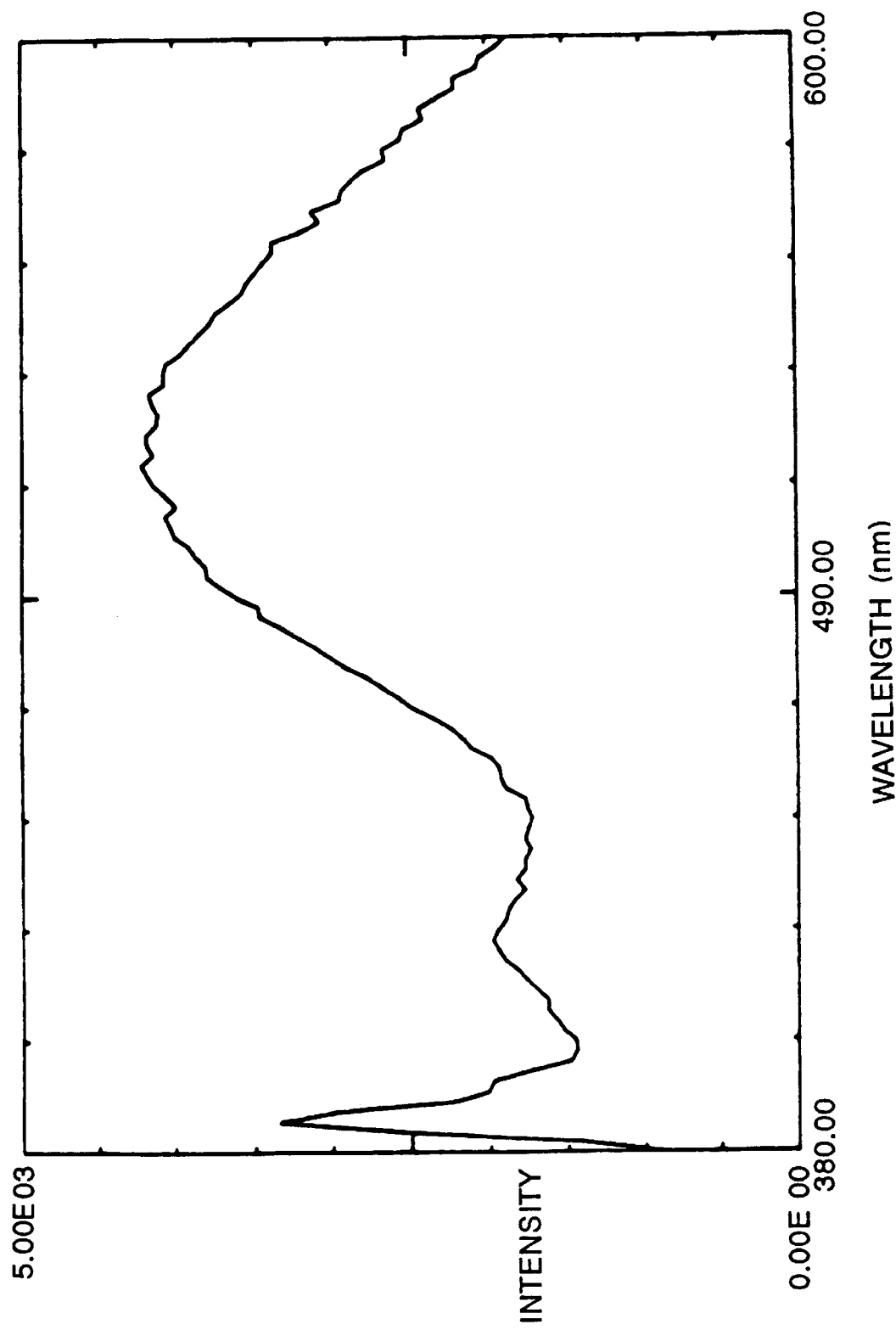

FIG. 13. Shows the fluorescent emission spectrum of P3.

Figure 14A:
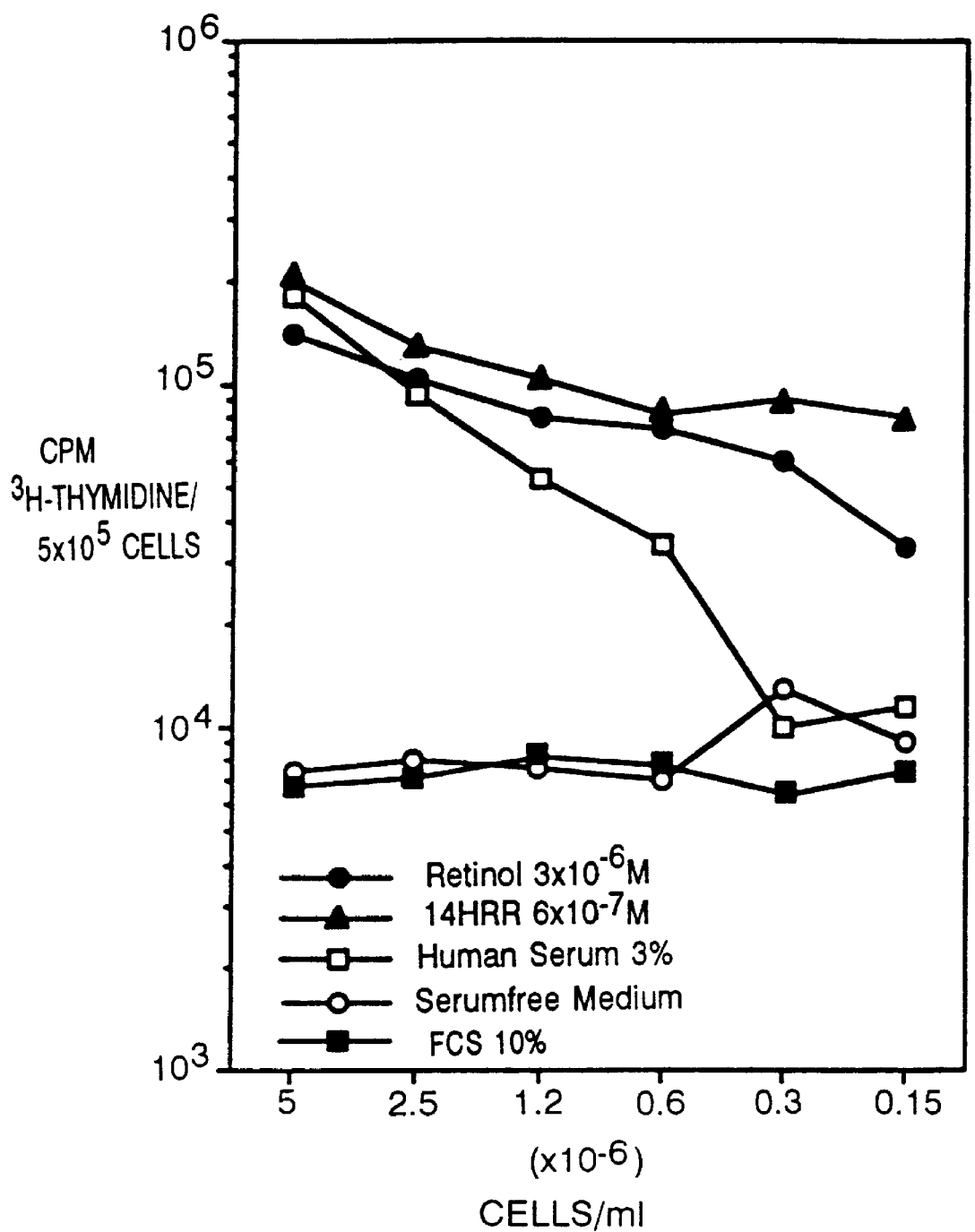
Figure 14B:
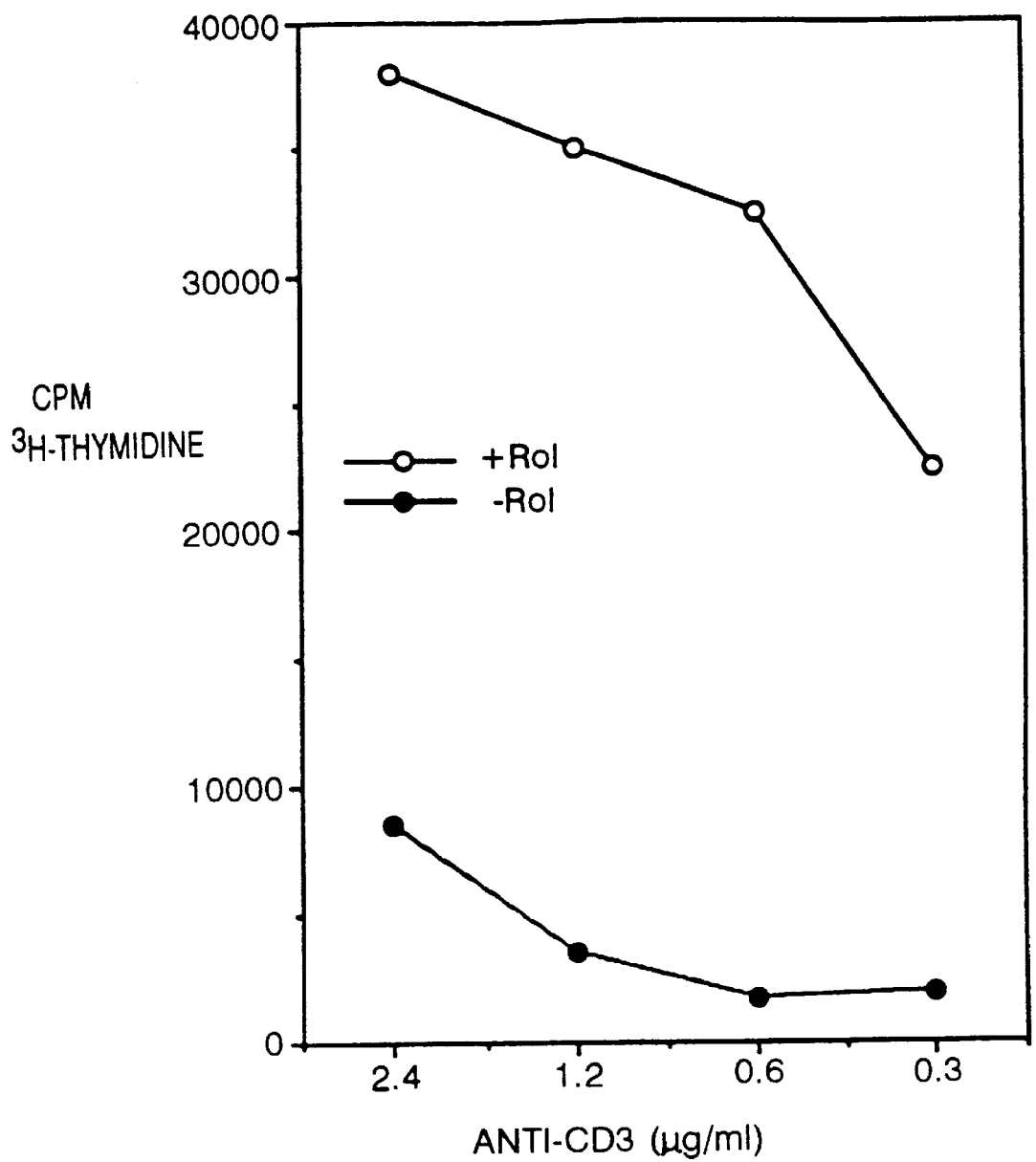

FIGS. 14A through 14C. Retinoids are required cofactors for proliferation of anti-CD3e activated thymocytes at low cellular density.

FIG. 14A: Purified BALB/c thymocytes were activated with immobilized anti-CD3e antibody and cultivated for four days in ITLB medium with or without retinol (3×10$^{-6}$M), 14HRR (6×10$^{-7}$M) (fresh 14HRR was added every 12 hours), human serum (3%) or FCS (10%) at the cellular densities shown. Proliferation was assayed by tritiated thymidine incorporation into cellular DNA. The SDs were below 20%.

FIG. 14B: BALB/c thymocytes (10$^6$/ml) were added to microtiter plates coated with titrated amounts of anti-CD3e antibody with 3×10$^6$M retinol or without, as indicated. Proliferation was measured in hexaduplicate wells on day 3 by $^3$H thymidine incorporation assay.

FIG. 14C: BALB/c thymocytes (3×10$^6$/ml) were activated with anti-CD3e mAb as FIG. 1A. The total number of viable cells was determined by counting trypan blue-excluding cells, and those of blast cells by counting viable large cells in six replicate wells. Because of the relatively low cell density required in the culture (see FIG. 14A), the numbers reported for blast cells are best estimates.

Figure 15B:
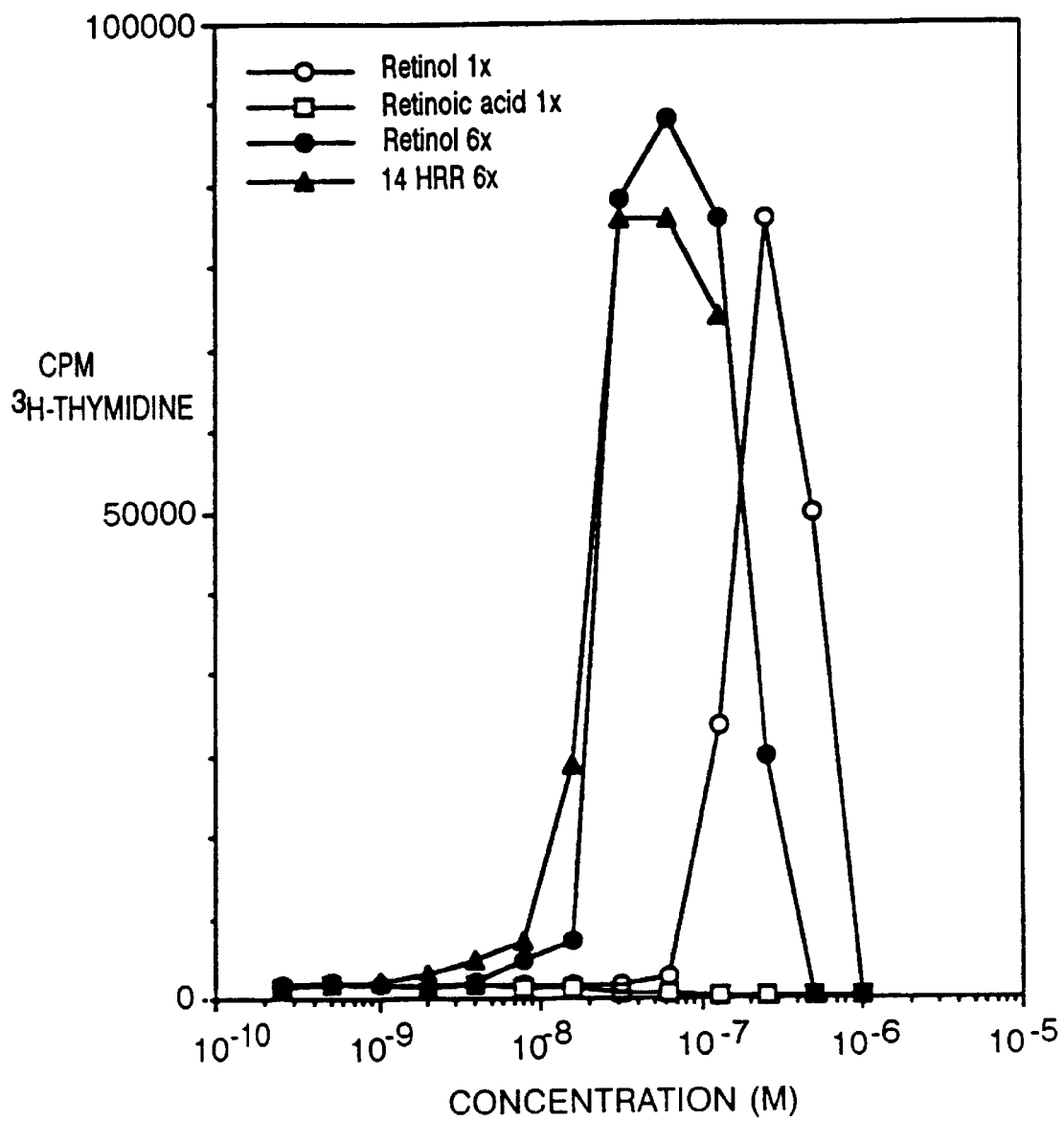

FIGS. 15A and 15B. Dose responses elicited by different retinoids.

Purified thymocytes (5×10$^5$ cells/well) were stimulated by TCR crosslinking with immobilized anti-CD3e antibody (FIG. 15A) or 0.4 μg/ml Con A (FIG. 15B) in serum-free ITLB medium. The indicated amounts of retinoids were added either once at the beginning of the experiment (marked as "1×") or every 12 hours thereafter (marked as "6×"). DNA synthesis was measured after 72 hours by tritiated thymidine uptake as described.

Figure 16:
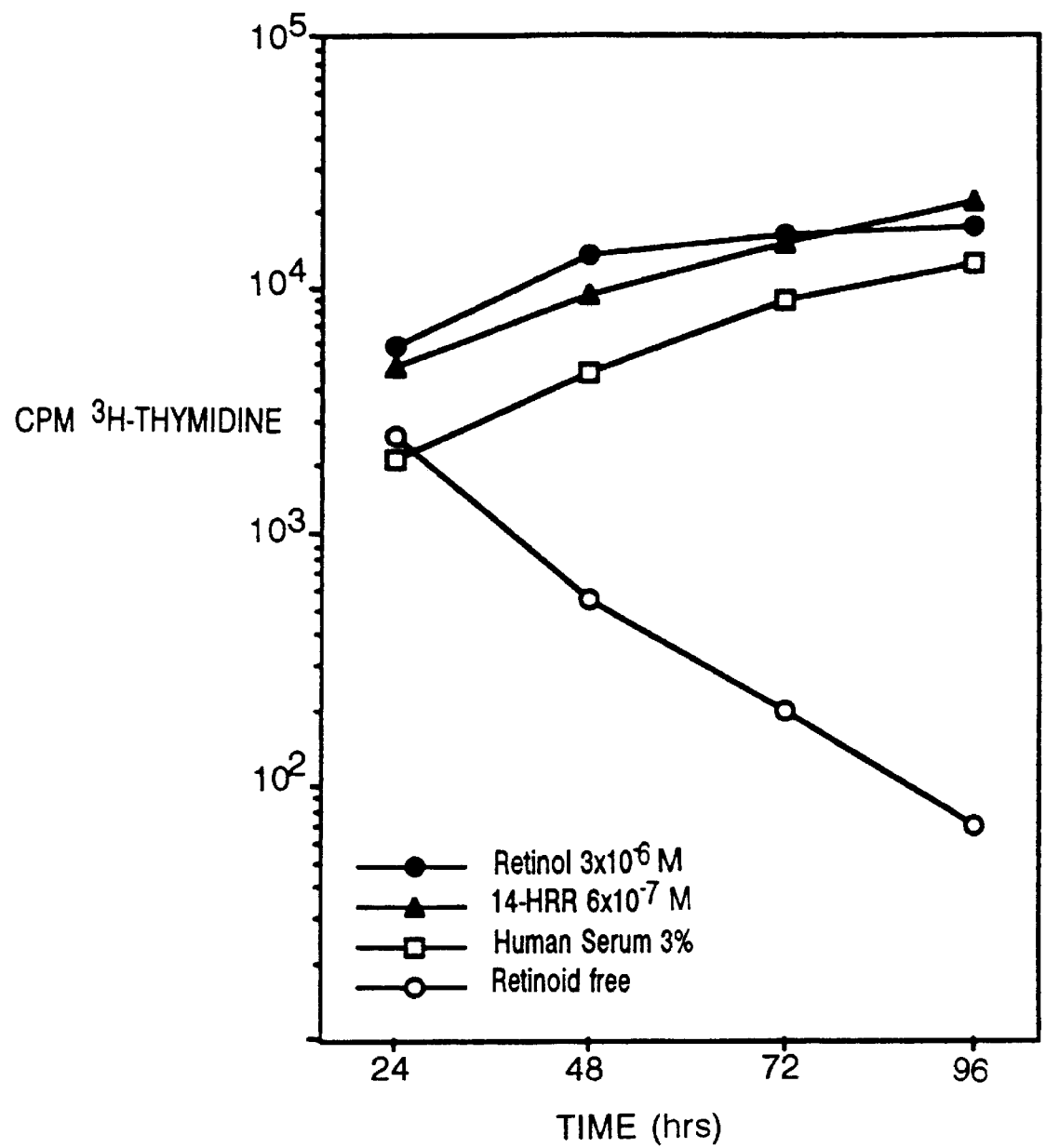

FIG. 16. Growth curves of activated thymocytes with serum-containing or serum-free medium, and in the presence or absence of retinoids.

Purified thymocytes (10$^5$ cells/well) were activated with anti-CD3 antibody in ITLB medium with or without retinol (3×10$^{-6}$M), 14HRR (6×10$^{-7}$, added every 12 hours or human serum (3%)). DNA synthesis was measured daily by a 4 hour pulse of tritiated thymidine. SDs were ≦12%.

FIGS. 17A through 17D. Retinoids are required cofactors for anti-CD3 activated peripheral T lymphocytes.

Growth curves of lymph node T cells depleted of antigen-presenting cells (FIG. 17A) with and without 10$^{-6}$M retinol at 2×10$^5$ and 5×10$^4$ cells/well. (FIG. 17B) Dose-responses elicited by different retinoids in cultures of lymph node T cells depleted of antigen-presenting cells. Also shown are the growth curves of CD4$^+$ (FIG. 17C) and CD8$^+$ T lymphocytes (FIG. 17D) in the presence of either retinol, 14HRR, human serum or in their absence.

T lymphocytes, purified as described, 5×10$^4$/well, were activated with immobilized anti-CD3 antibody in ITLB medium. The indicated amounts of retinoids or human serum were added at initiation of cultures. Culture medium of CD8$^+$ T cells was supplemented with IL-2 (2U/ml). 14HRR was added every 12 hours. DNA synthesis was measured by a 4 hour pulse with tritiated thymidine. SDs were ≦17%.

Figure 18:
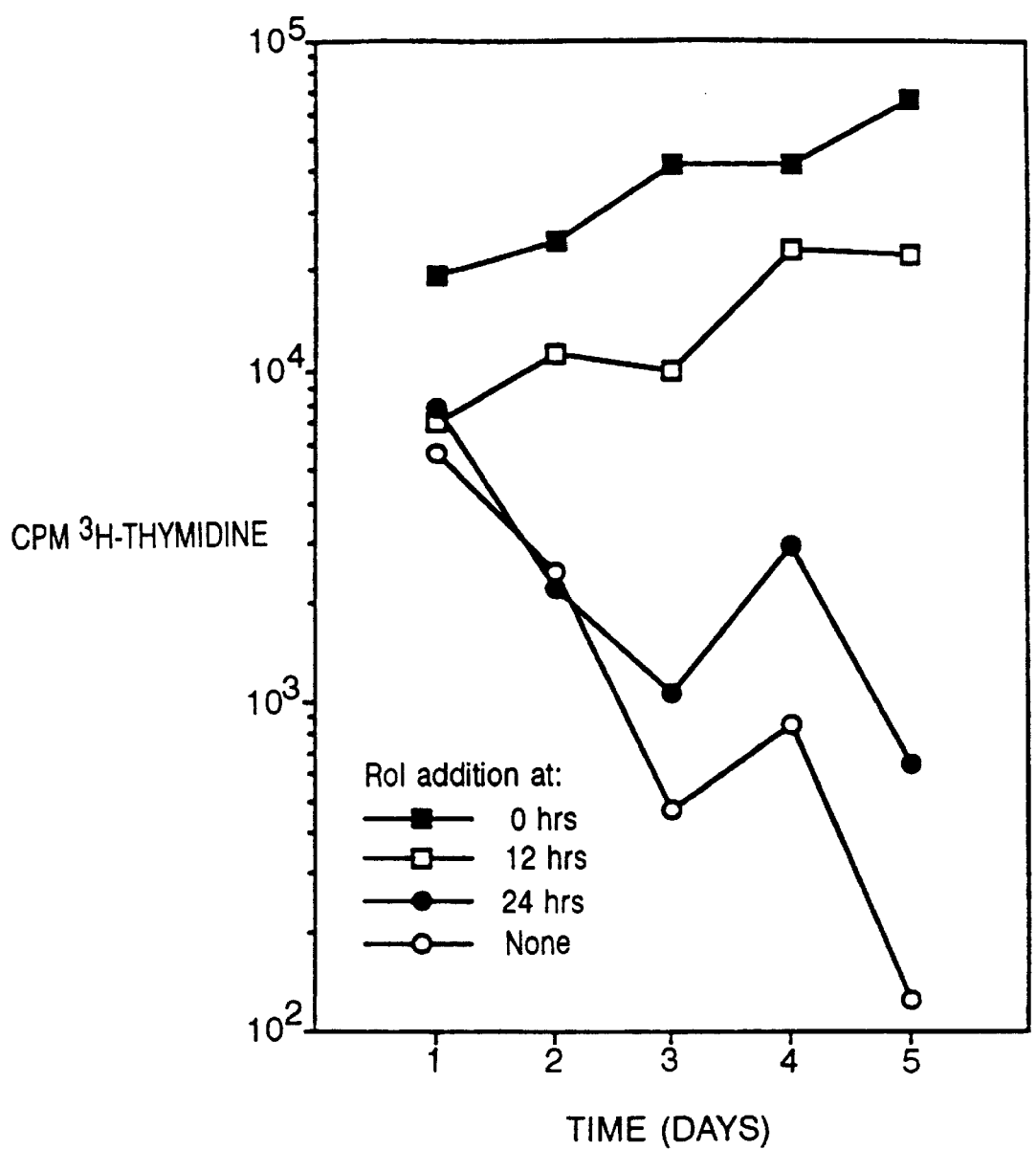

FIG. 18. Retinol is required at the time of activation.

Thymocytes (5×10$^4$/well) were activated by immobilized anti-CD3 mAb in medium ITLB. Retinol (2×10$^{-6}$M) was added at initiation of culture, or delayed by 12 hours and 24 hours, respectively, or omitted altogether. $^3$H thymidine pulses of 4 hours were used to measure DNA synthesis of hexaduplicate wells. (SDs were 20% or less.)

Figure 19:
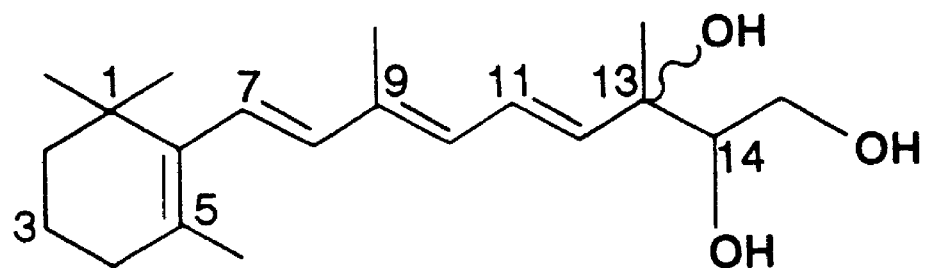

FIG. 19. Structure of 13,14 DHR Dihydroxy retinol.

Figure 20:
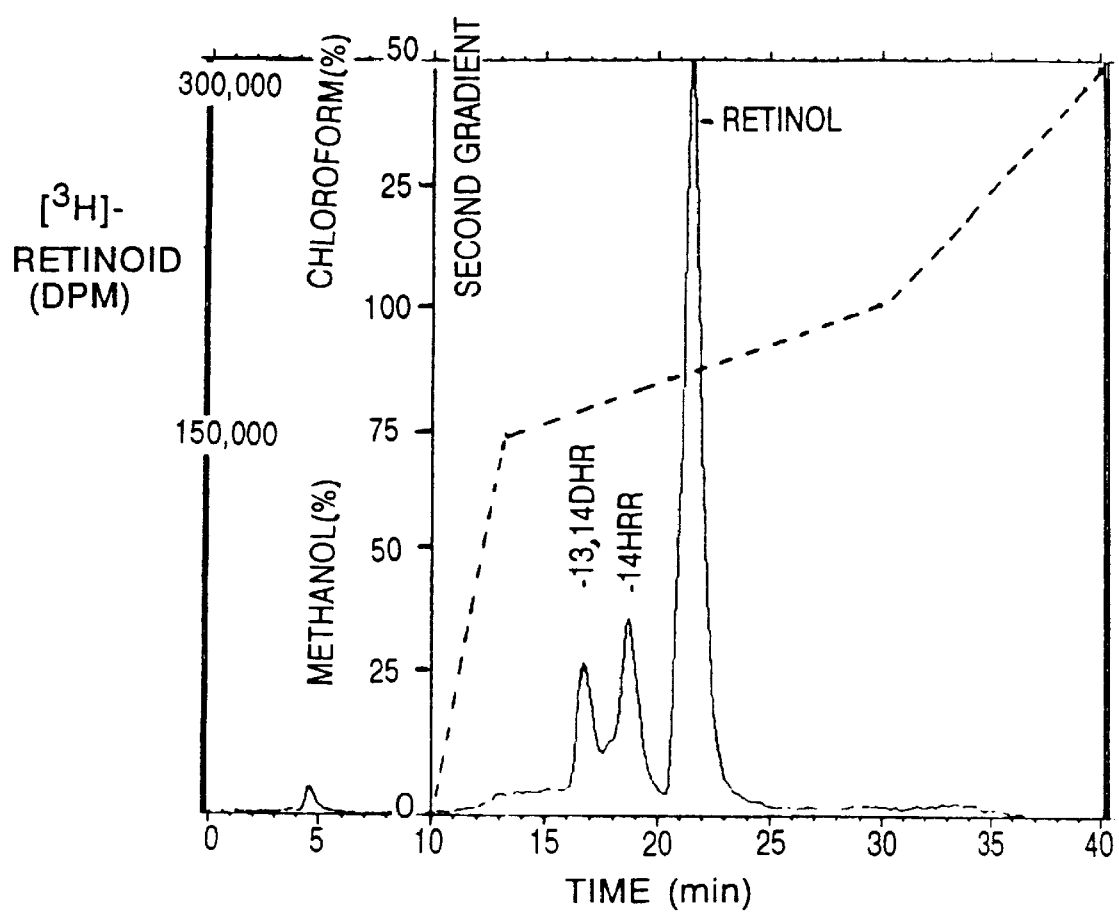

FIG. 20. High-pressure liquid chromatography of retinoids from anti-CD3 activated spleen cells.

HPLC system (Water, Milford, Mass.), analytical C$_{18}$ reversed-phase column (Vydac, Hesperia, Calif.); water-methanol-chloroform gradient; flow rate 1 ml/min.

Disintegradions per minute were determined with an on-line scintillation counter (Radiomatic, Tampa, Fla.). xx10$^x$ mouse spleen cells (BALB/c) were incubated in ITLB medium with 10$^{-7}$M retinol, and 20 μCi [$^3$H] retinol, specific activity: 49.3 Ci/mnol added in 3 cm petri dishes which had ng/ml anti-CD3 prebound. After 18 hours retinoids were extracted according to the procedure of McLean et al (13).

Figure 21A:
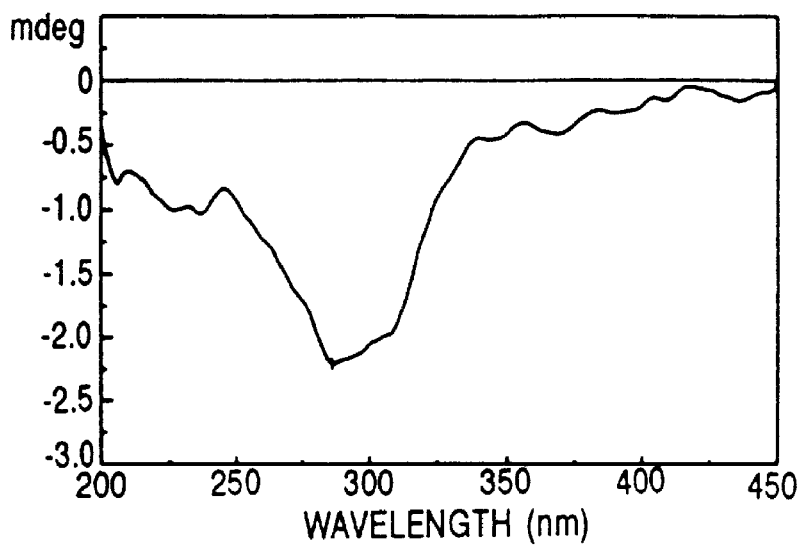
Figure 21B:
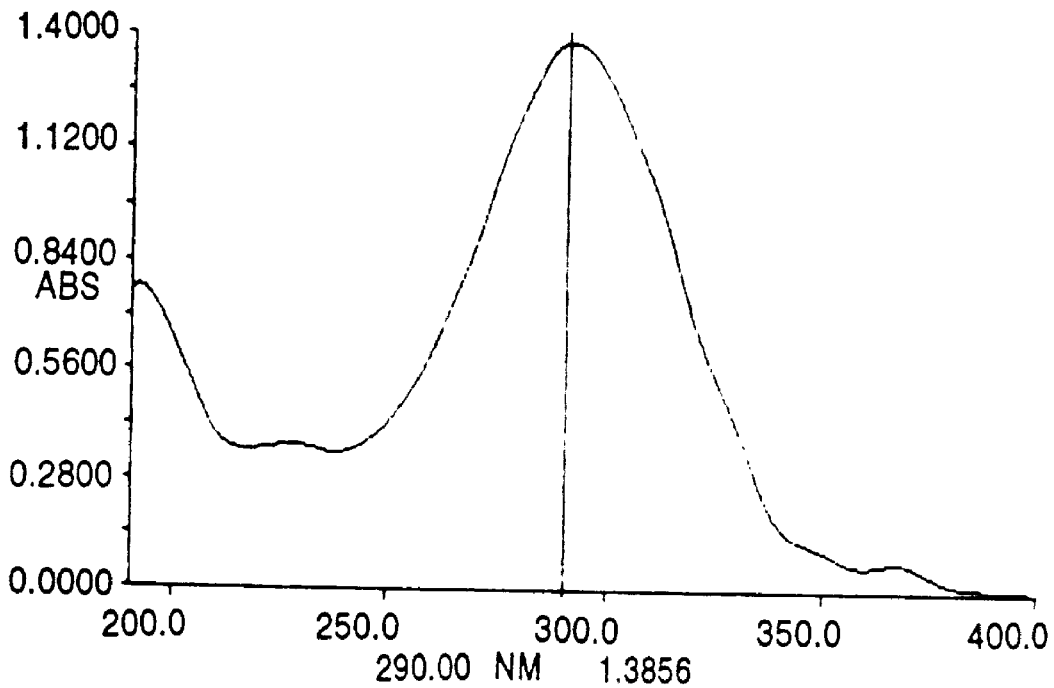

FIGS. 21A and 21B. FIG. 21A: Circular dichroism spectrum of biological 13,14DHR in methanol (Jasco J-720 spectropolarimeter). FIG. 21B) UV absorption of 13,14-DHR in methanol (Perkin-Elmer Model-Lambda 4B UV/DIS Spectrometer).

Figure 22A:
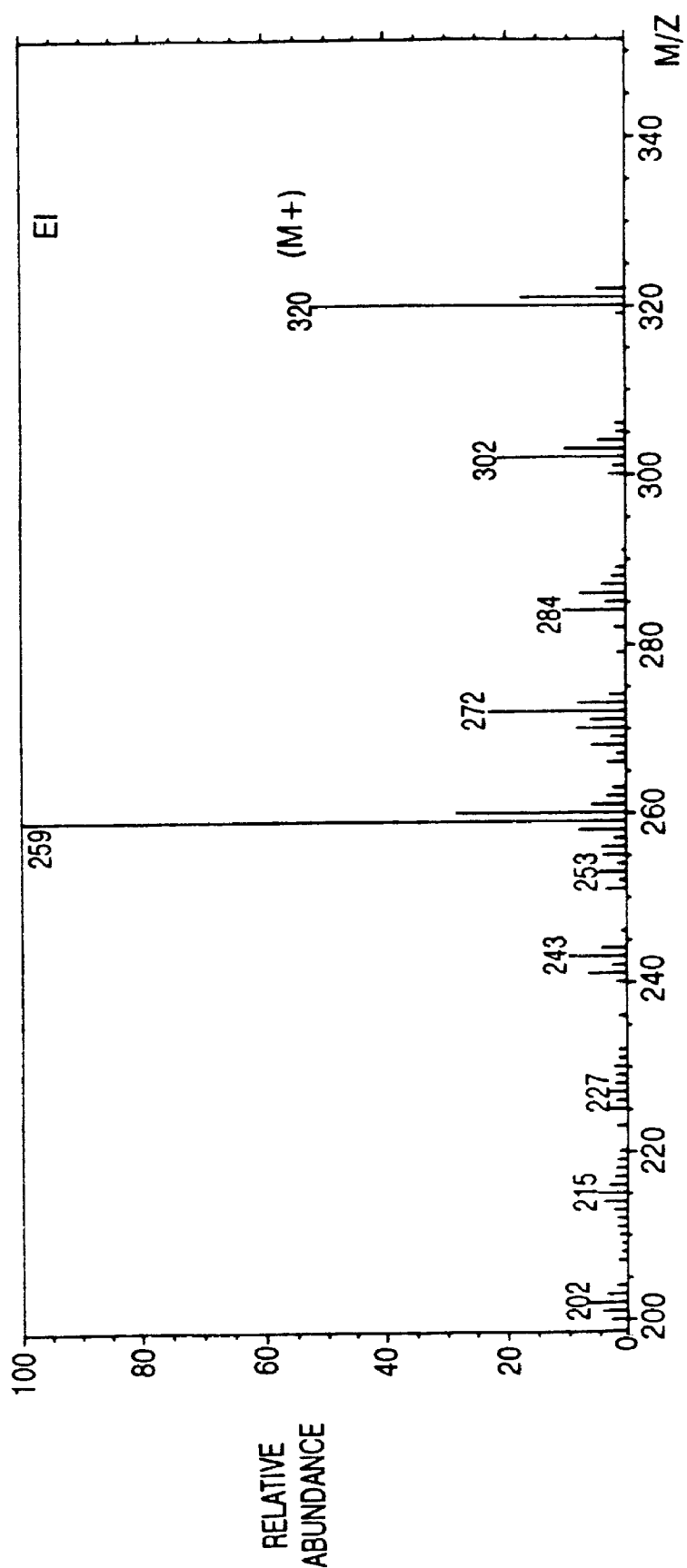

FIGS. 22A and 22B-1 through 22B-2. FIG. 22A: Low resolution EI mass spectrum of 13,14DHR.

Figure 1:
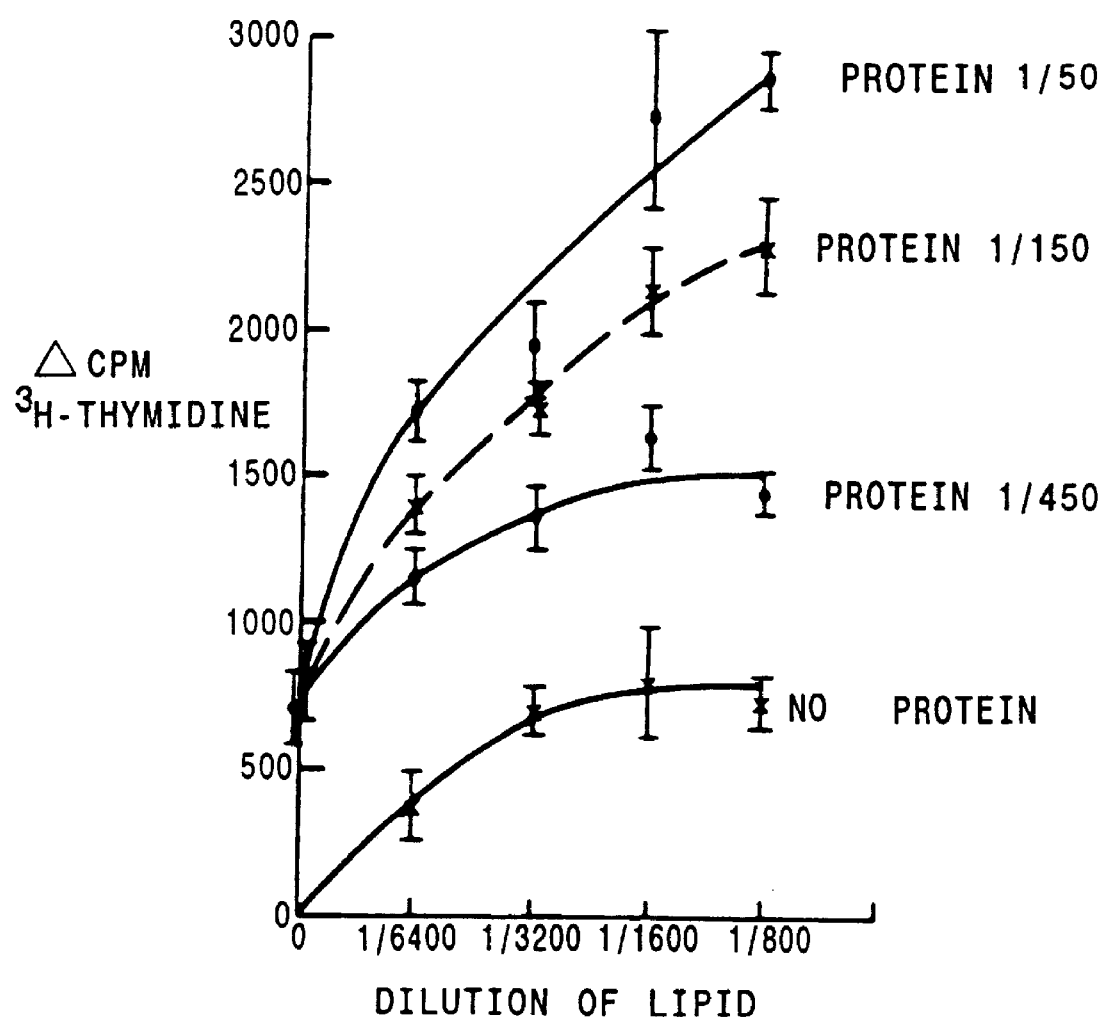
FIG. 1. Protein and lipids of conditioned medium are synergistic in their ability to sustain the growth of β lymphocytes.

FIGS. 22B-1 and 22B-2 High resolution mass spectrum of natural 13,14DHR.

FIGS. 23A-1 through 23B-2 $^1$H NMR: Nuclear magnetic resonance spectrum of natural 13,14DHR.

Figures 1, 23A:
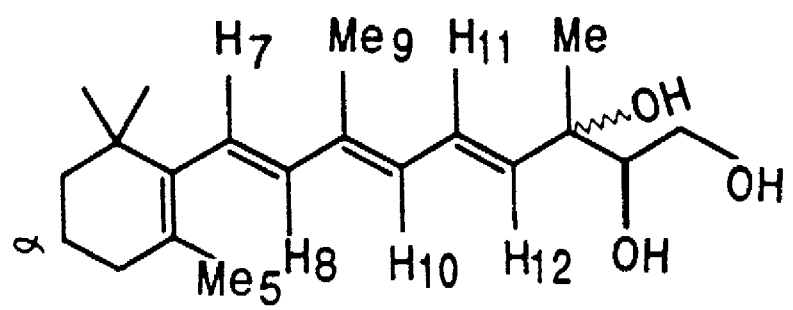
Figures 2, 23A:
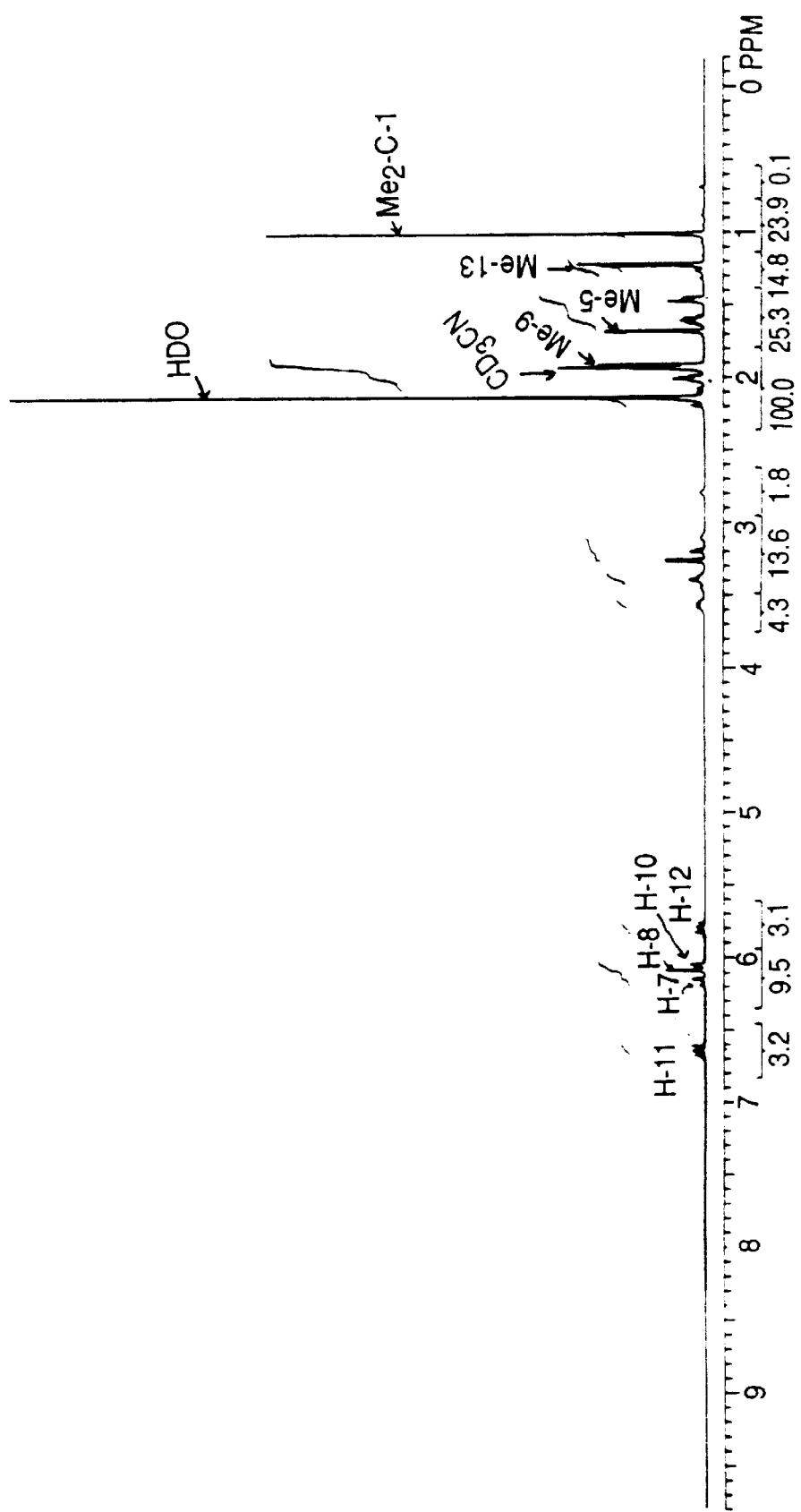
Figures 1, 23B:
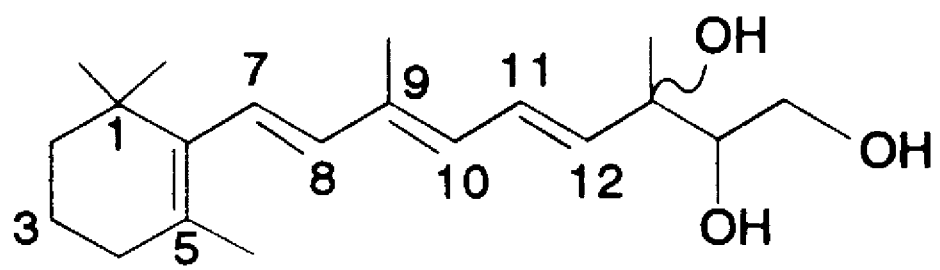
Figures 2, 23B:
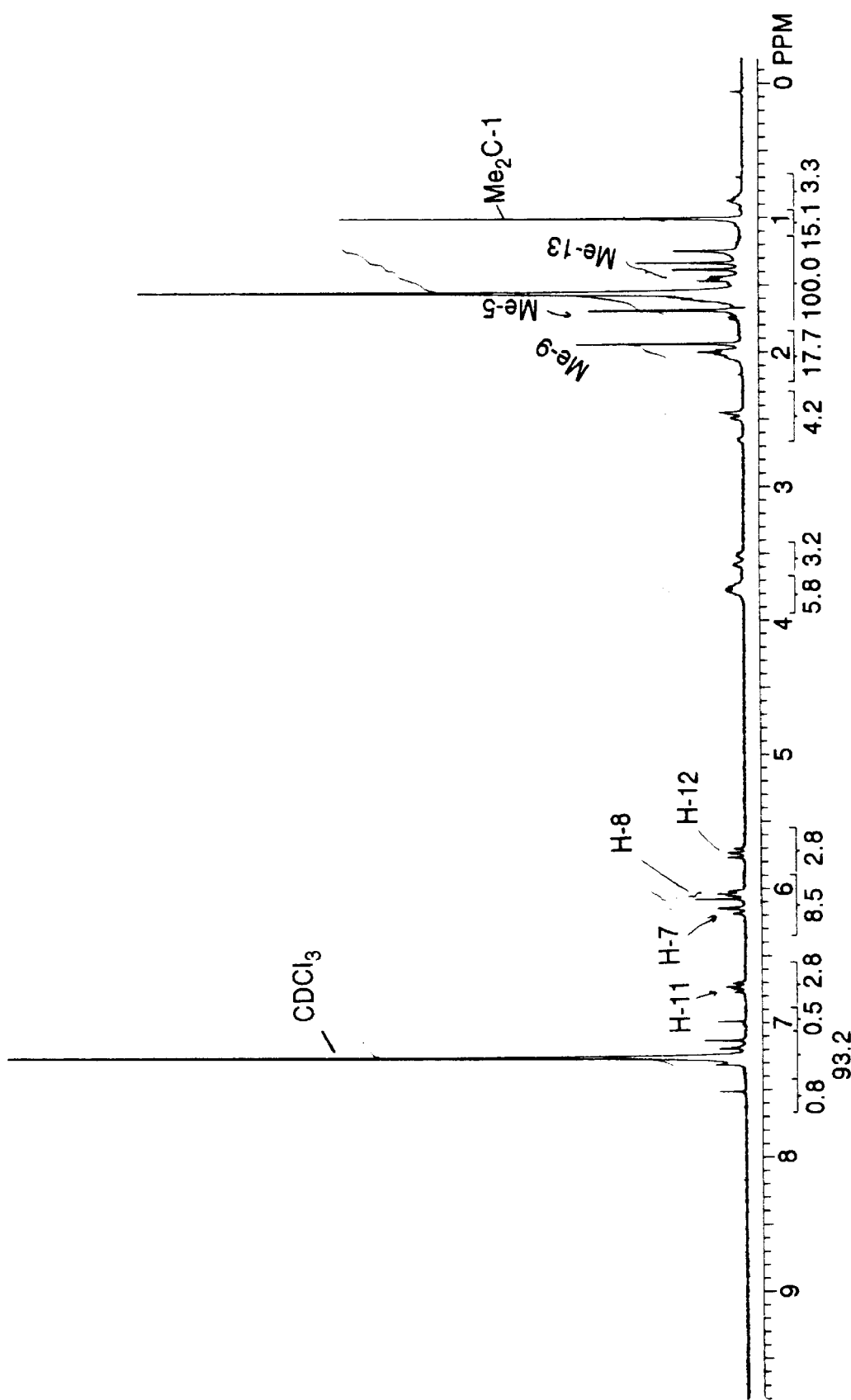

FIGS. 23A-1 through 23B-2 in CD$_3$CN;

FIGS. 23B-1 and 23B-2 in CDCl$_3$.

Figure 24:
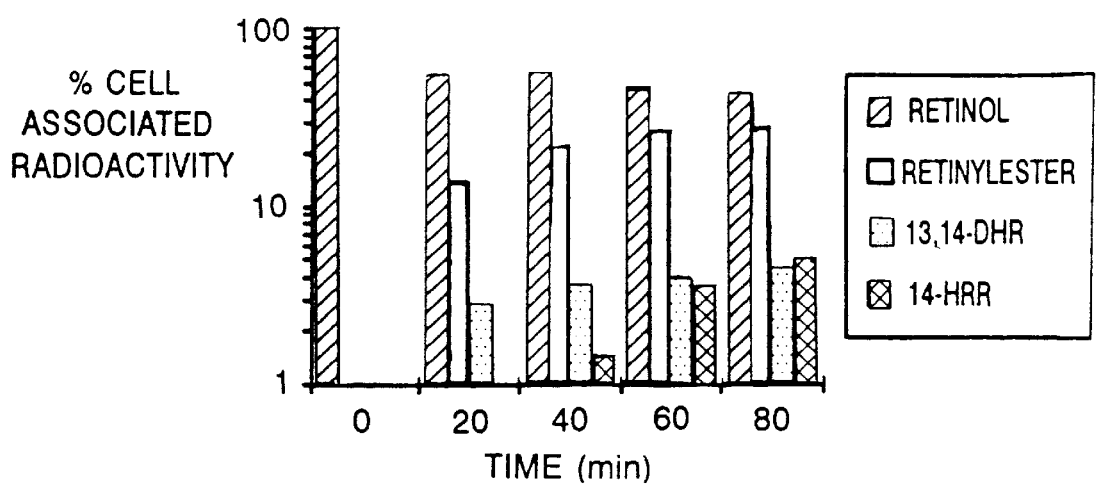

FIG. 24. Kinetics of biosynthesis of 14HRR in lymphoblastoid cells. 50 ml ITLB 600,000 5/2 cells/ml were incubated with 20 μCi of $^3$H retinol in serum-free ITLB medium. Cell pellets corresponding to 10 ml of culture were delipidated at 20 minute intervals and the corresponding lipid fraction separated on an analytical C$_{18}$ reversed-phase column (see FIG. 20). Radioactive peaks were identified by coelution with cold reference retinoids.

FIGS. 25A through 25D. 13,14DHR can be converted to 14HRR by lymphoblastoid cells. 200,000 5/2 cells/ml were incubated with or without 10$^{-6}$M 13,14DHR added in serum-free ITLB medium. After 1 and 2 hours, cells pellets corresponding to 10 ml of culture were delipidated and the corresponding lipid fractions separated on an analytical C$_{18}$ reversed-phase column according to FIG. 20. Peaks were identified according to their retention times and their UV absorption patterns.

Figure 25A:
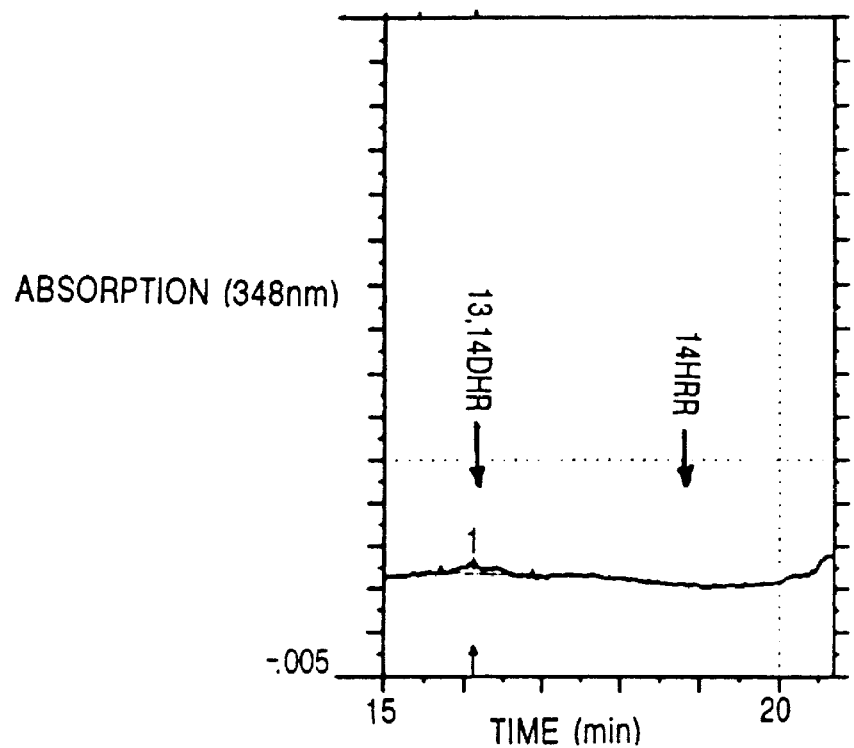

FIG. 25A. 1 hour no 13,14DHR added.

Figure 25B:
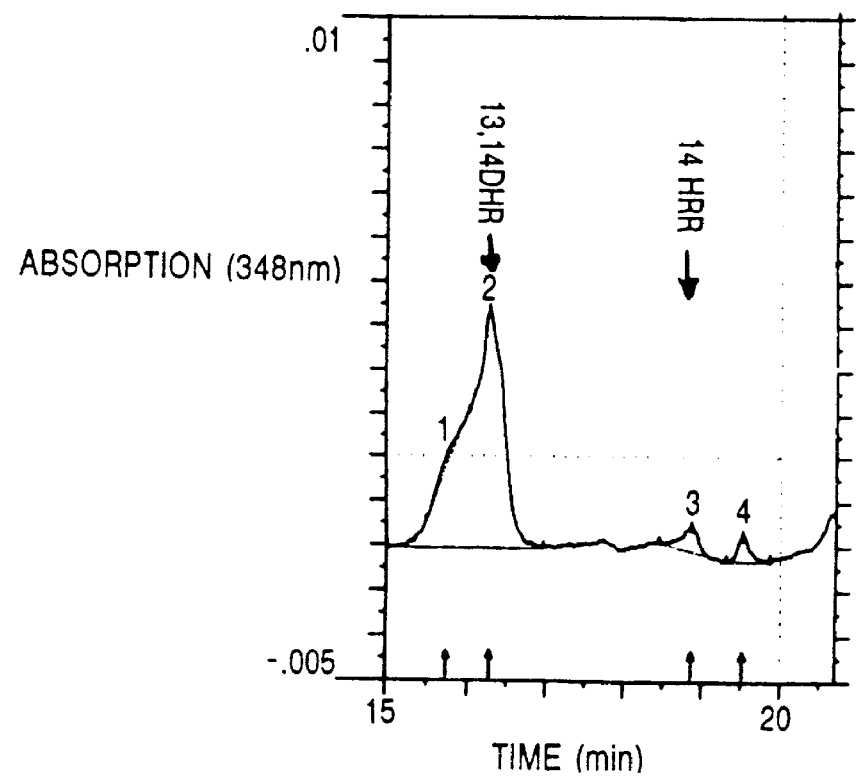

FIG. 25B. 1 hour 10$^{-6}$M 13,14DHR added.

Figure 25C:
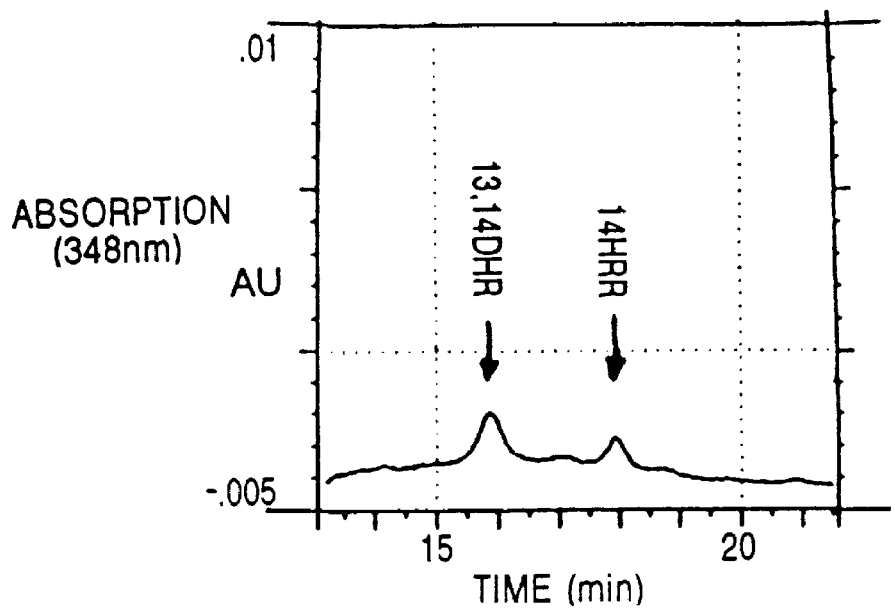

FIG. 25C. 2 hours 10$^{-6}$M 13,14DHR

Figure 25D:
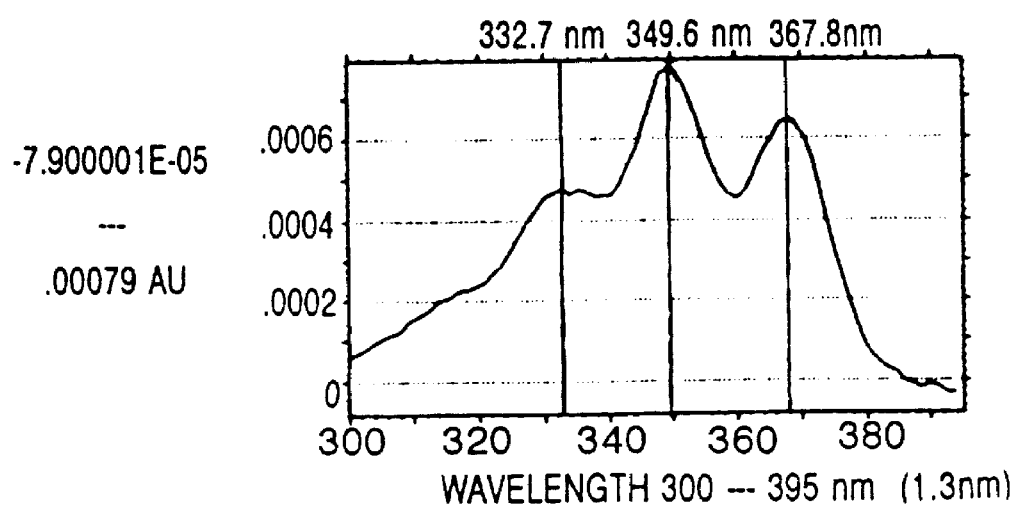

FIG. 25D. UV absorption peak of peak 18.6' of C (14HRR)

Figure 26:
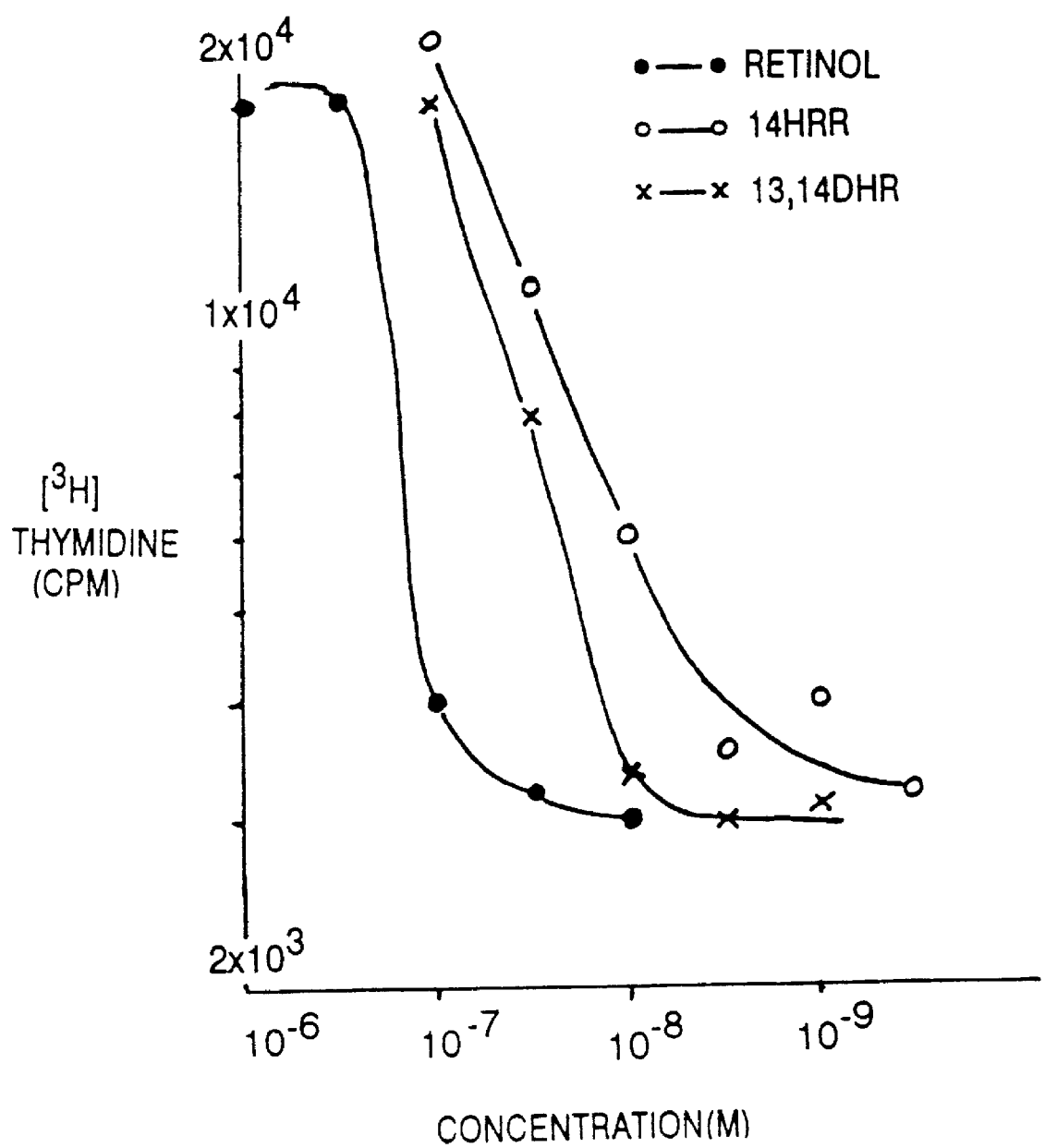

FIG. 26. Growth-supporting activity of 13,14DHR compared to that of retinol and 14HRR and dose response.

Lymphoblastoid 5/2 cells grown in RPMI/5% FCS were taken from their exponential growth phase, washed twice and seeded at 25,000 cells/ml in serum-free defined ITLB medium. The assay was done in 96-well microtiter plates in a final volume of 200 ul/well. The cells were cultured for 72 hours and cell growth determined by [$^3$H] thymidine (0.8 μCi/well) labeling for the last 16 hours. Retinoids were added at the indicated concentrations at the initiation of culture and every 24 hours thereafter.

FIGS. 27A-1 through 27B-3 $^1$HNMR: Nuclear magnetic resonance spectrum of compound 11 (less polar disastereomer).

Figures 1, 27A:
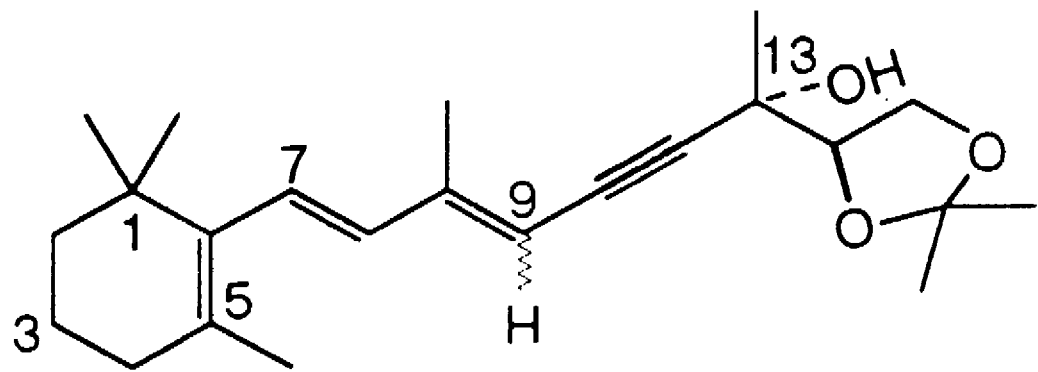
Figures 2, 27A:
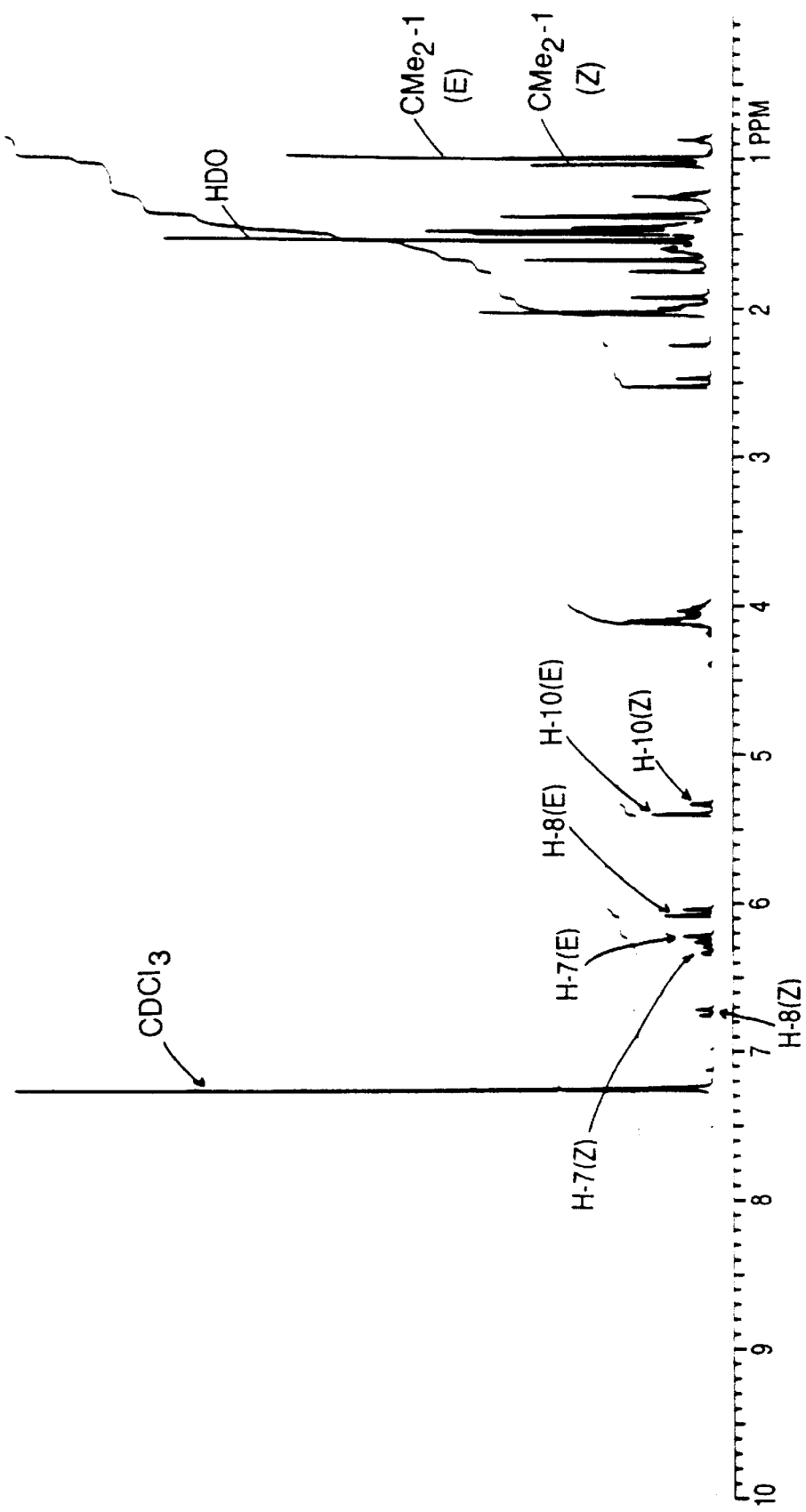
Figures 1, 27B:
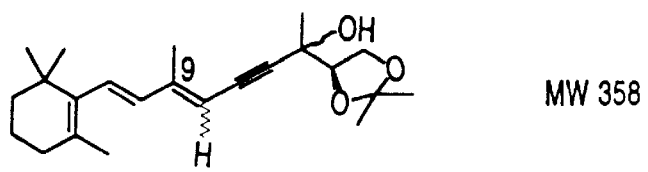
Figures 2, 27B:
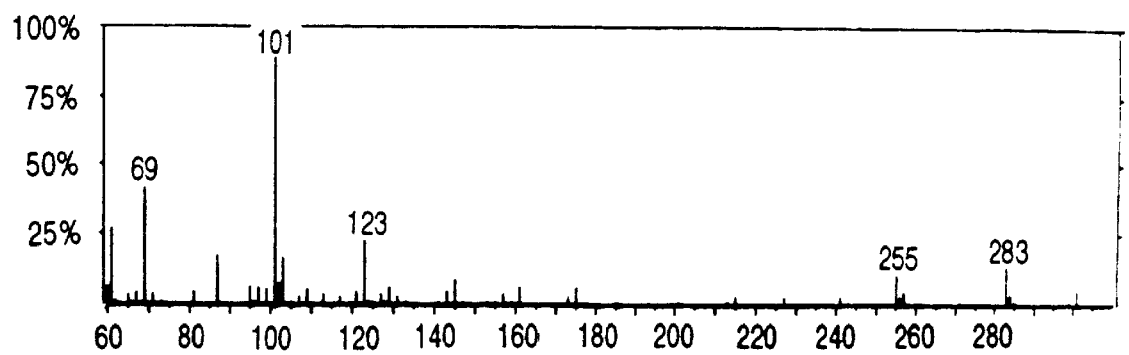
Figures 3, 27B:
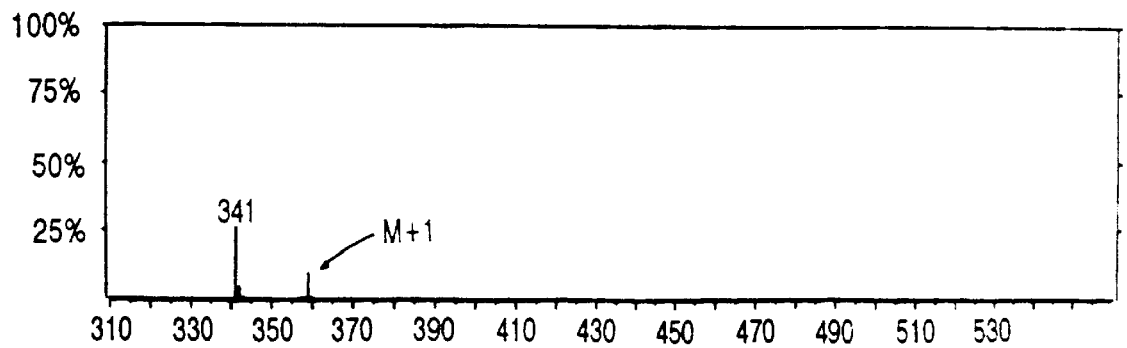

FIGS. 27B-1 through 27B-3 Low resolution mass spectrum of compound 11 (less polar disastereomer).

FIGS. 28A-1 through 28B-3 $^1$HNMR: Nuclear magnetic resonance spectrum of compound 11 (major isomer).

Figures 1, 28A:
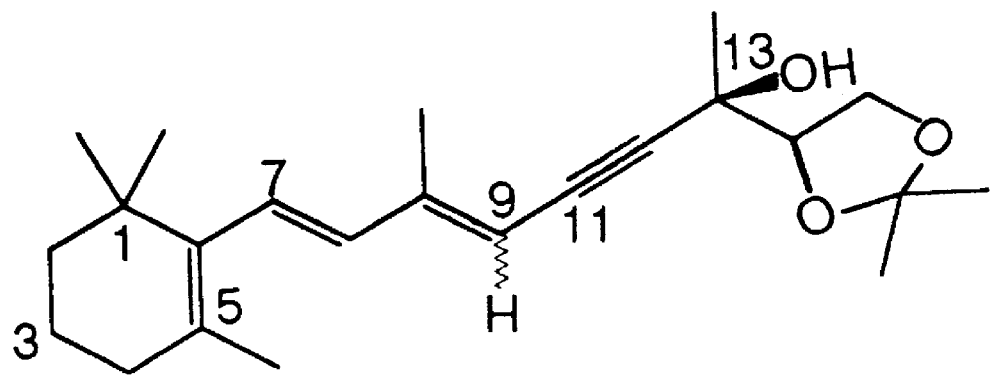
Figures 2, 28A:
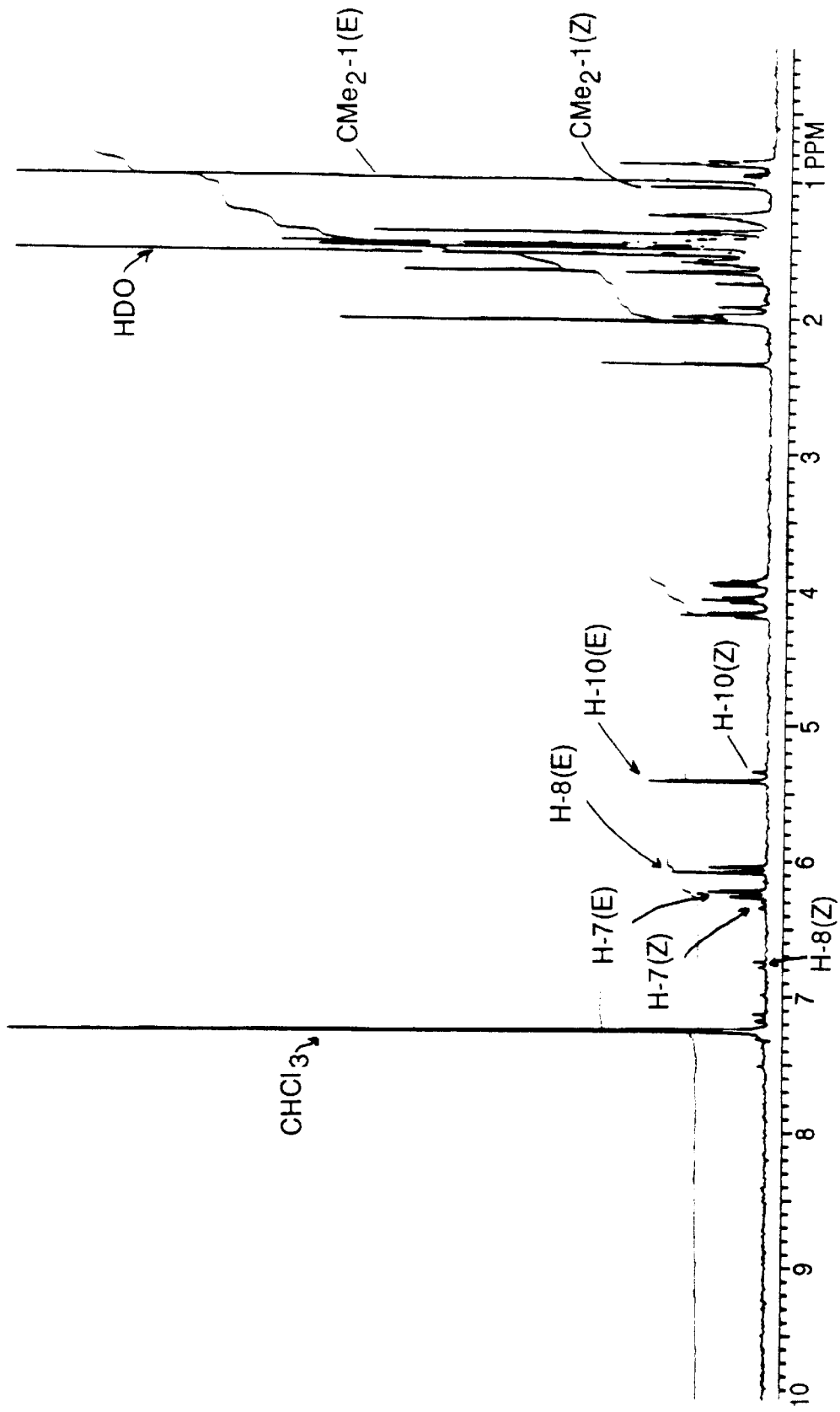
Figures 1, 28B:
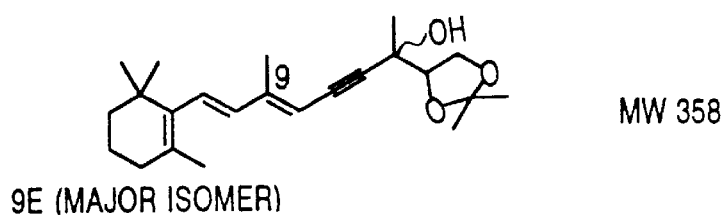
Figures 2, 28B:
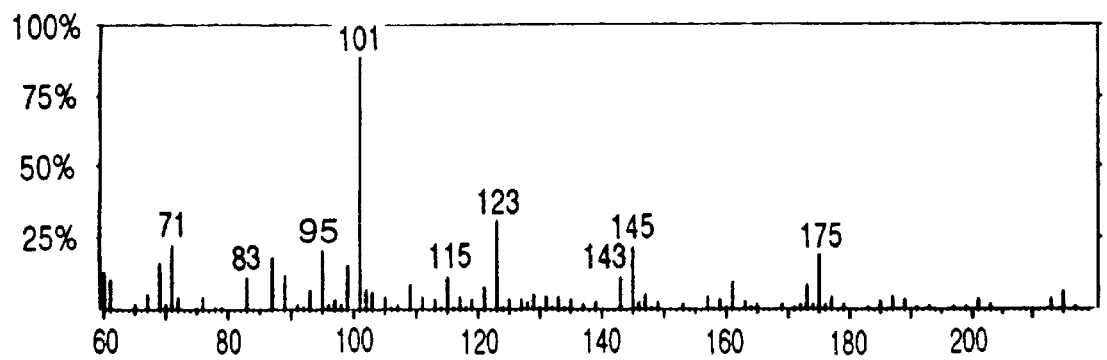
Figures 3, 28B:
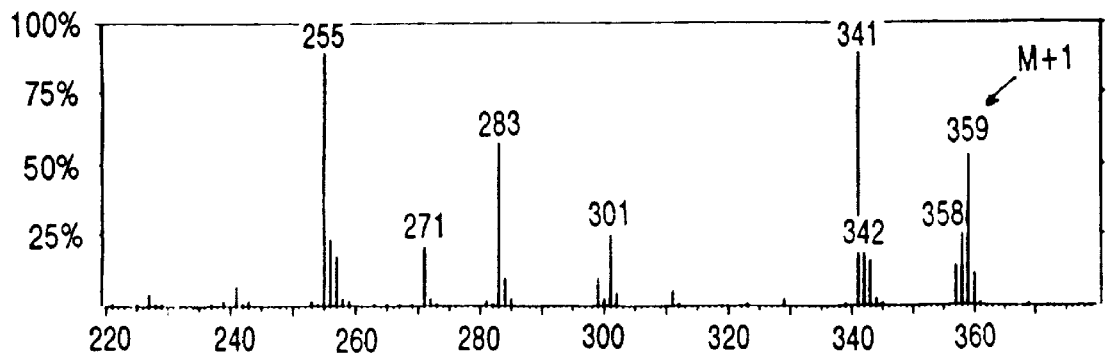

FIGS. 28B-1 through 28B-3 Low resolution mass spectrum of compound 11 (major isomer).

Figures 1, 29A:
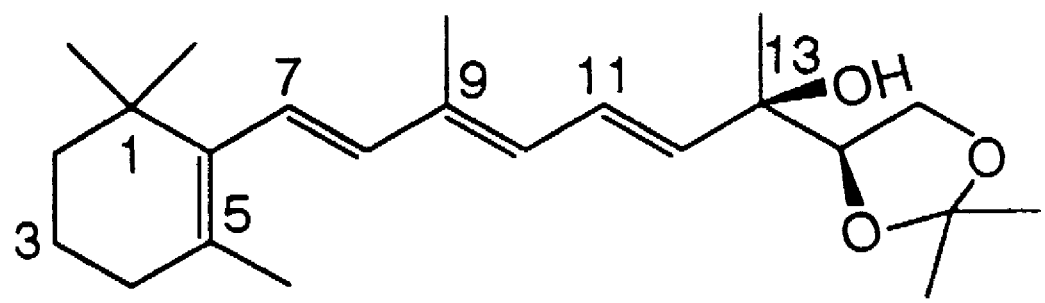
Figures 2, 29A:
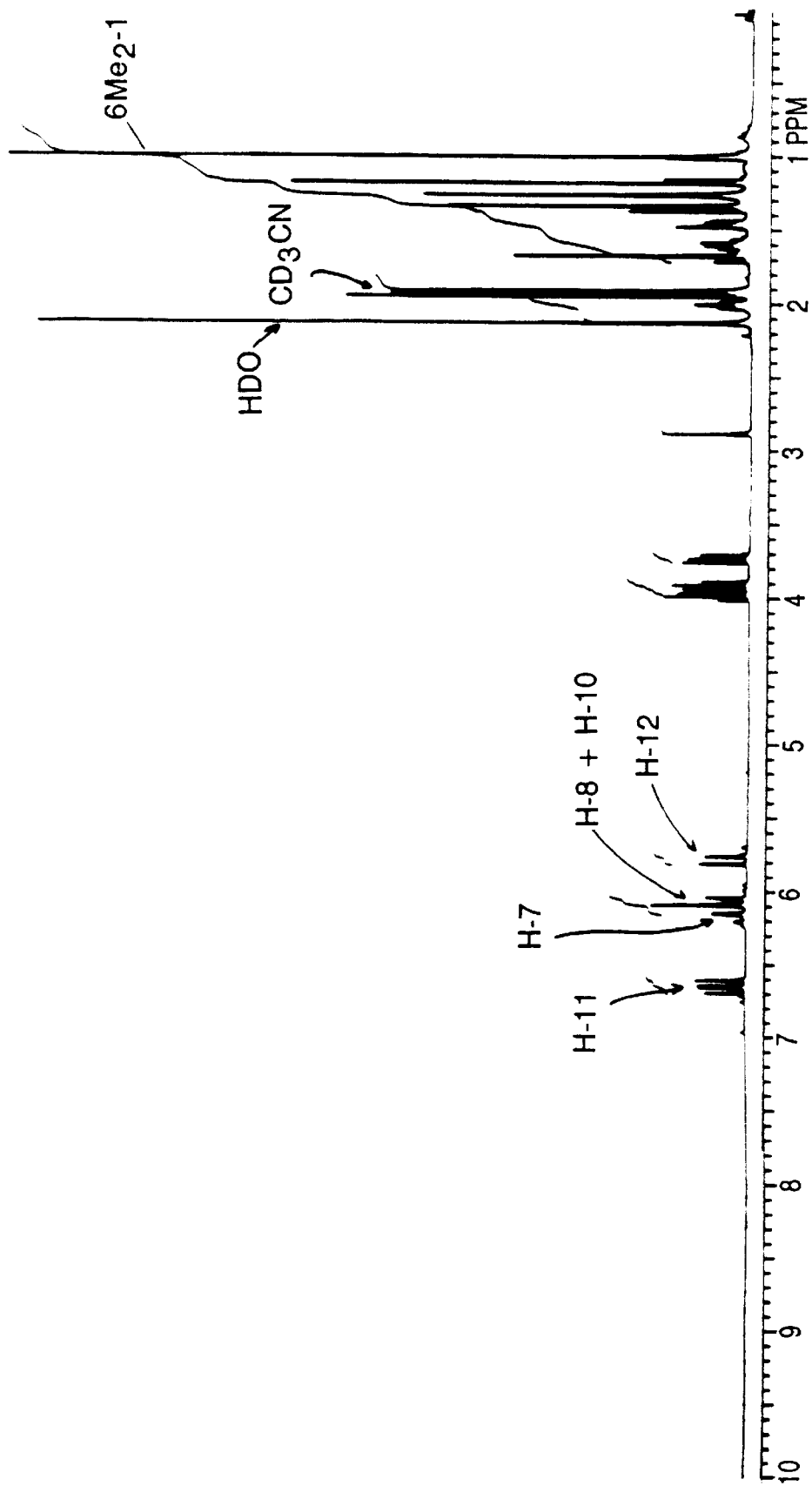

FIGS. 29A-1 and 29A-2 $^1$HNMR: Nuclear magnetic resonance spectrum of compound 12.

Figures 1, 29B:
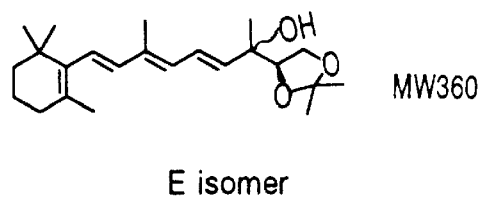
Figures 2, 29B:
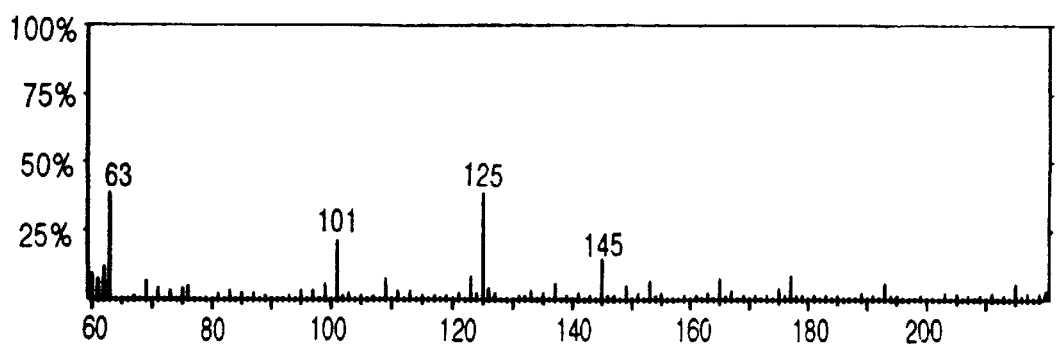
Figures 3, 29B:
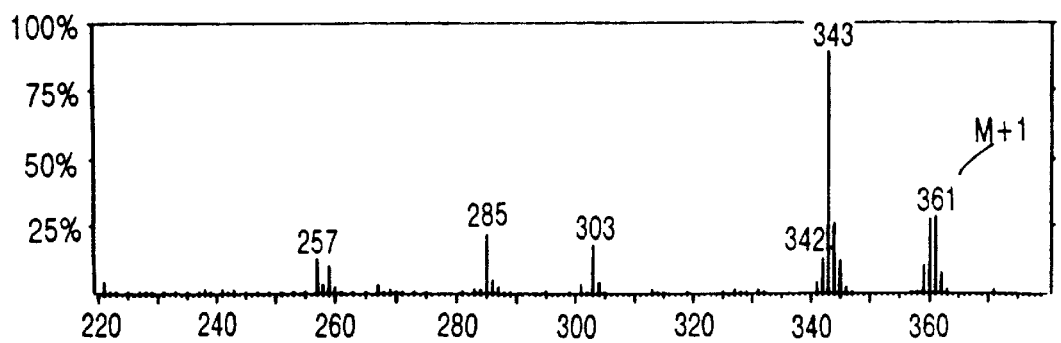

FIGS. 29B-1 through 29B-3 Low resolution mass spectrum of compound 12.

Figures 1, 29C:
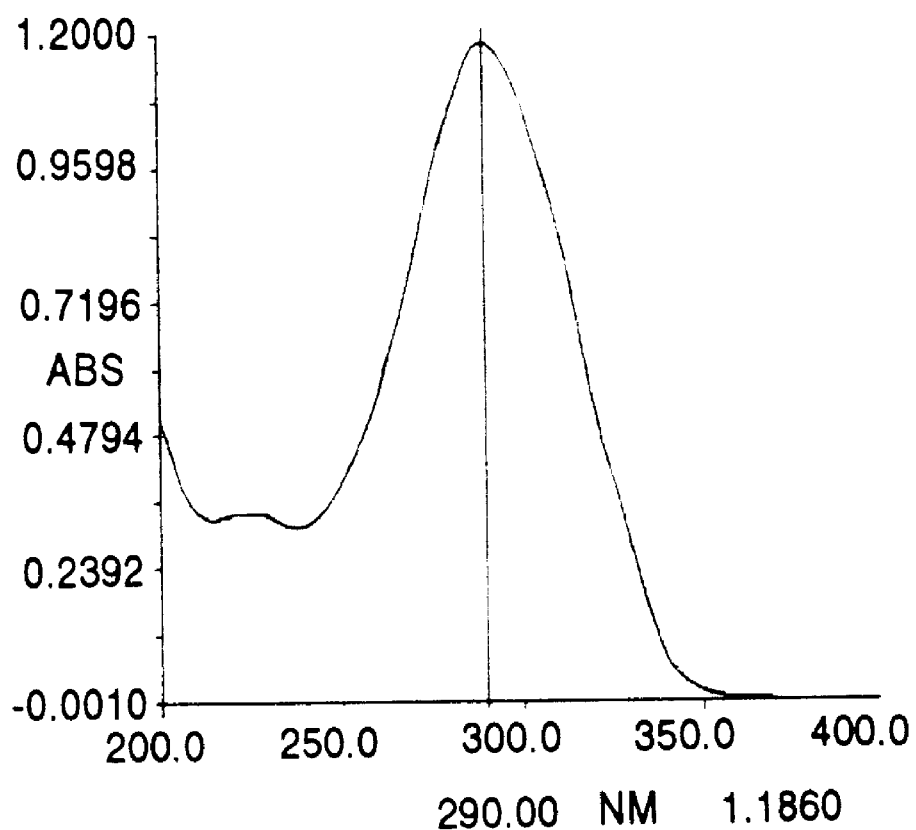
Figures 2, 29C:
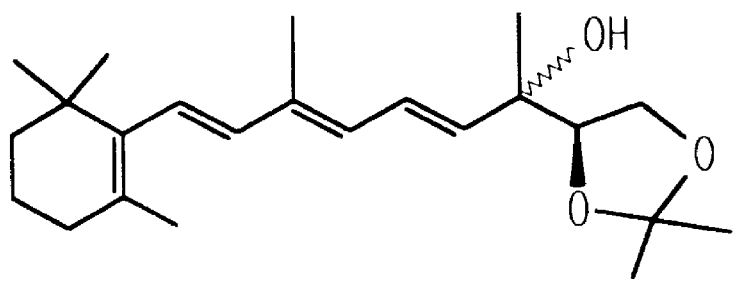
Figures 1, 30A:
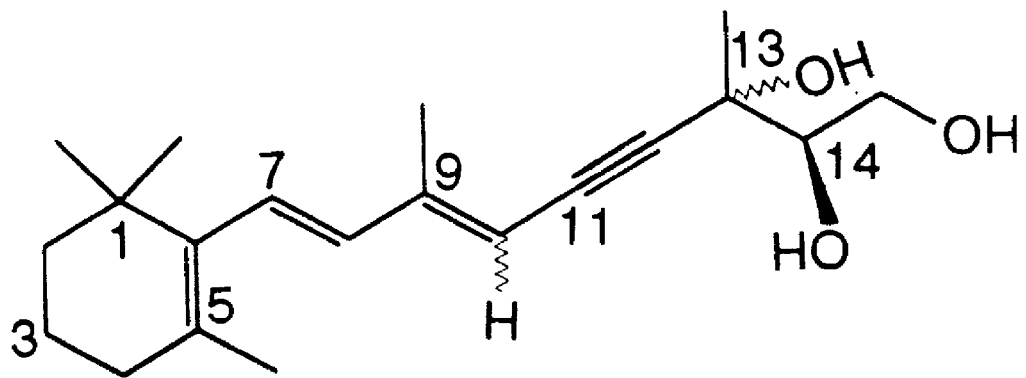
Figures 2, 30A:
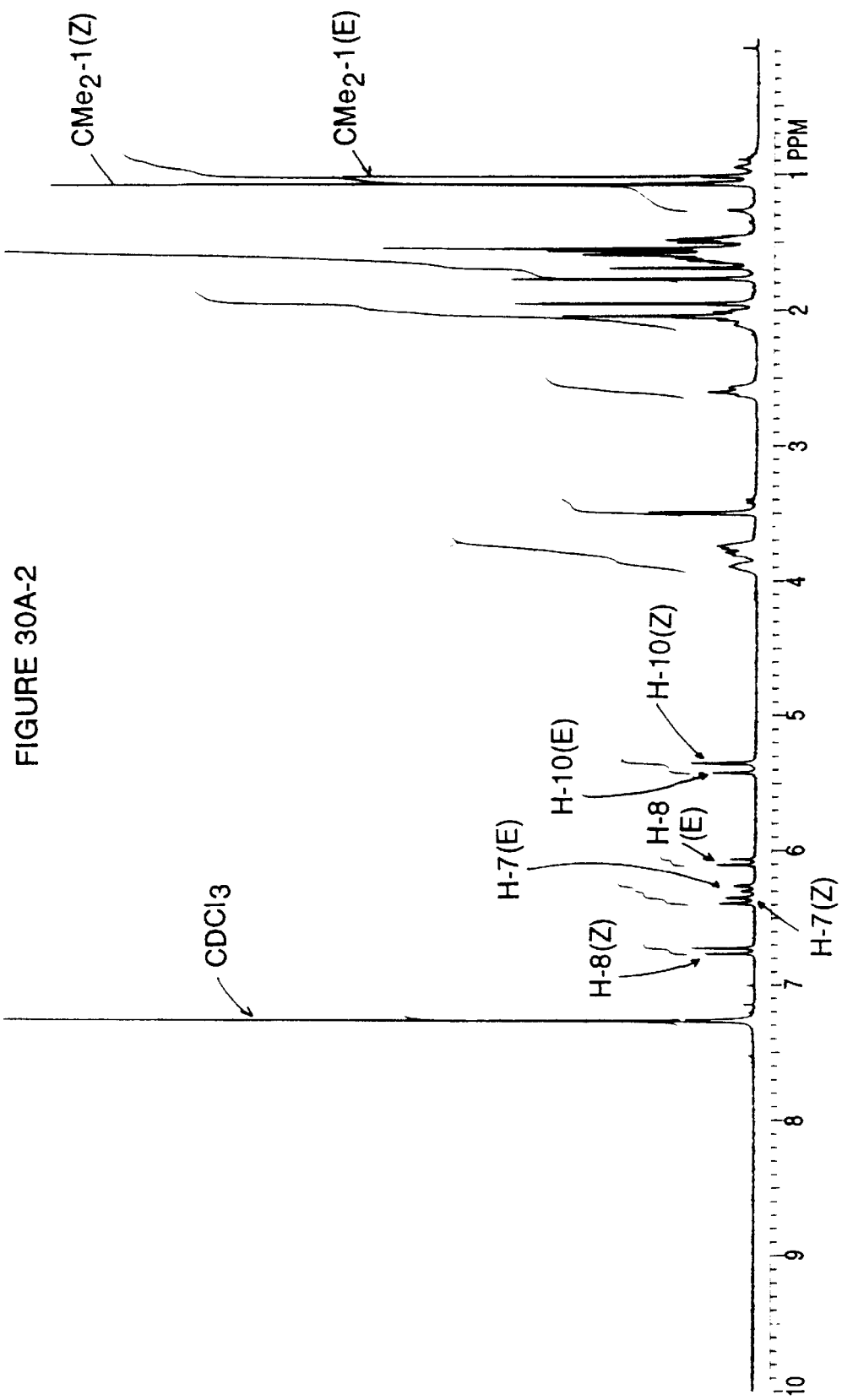
Figures 1, 30B:
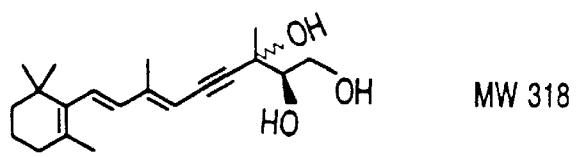
Figures 2, 30B:
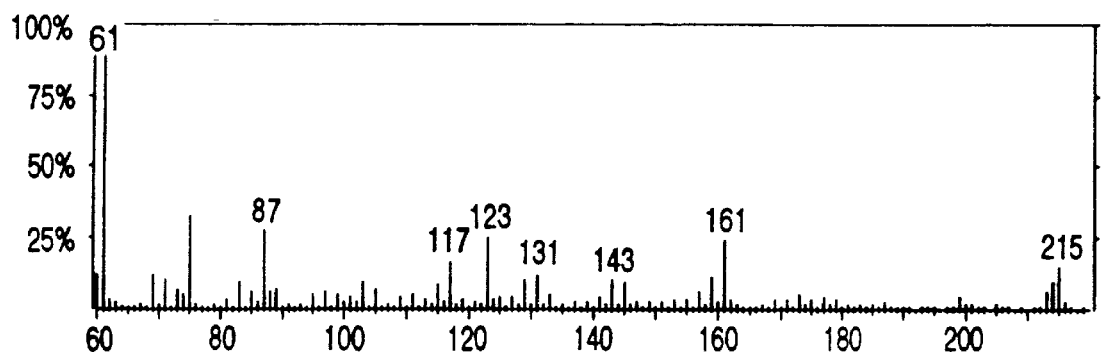
Figures 3, 30B:
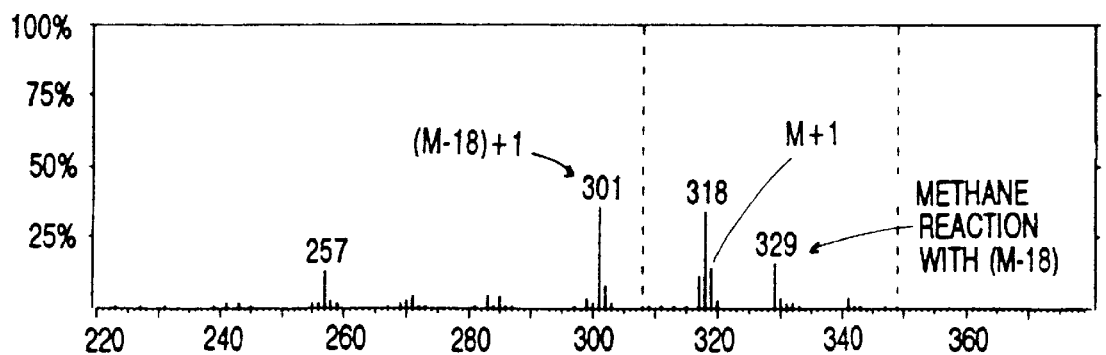
Figures 1, 31A:
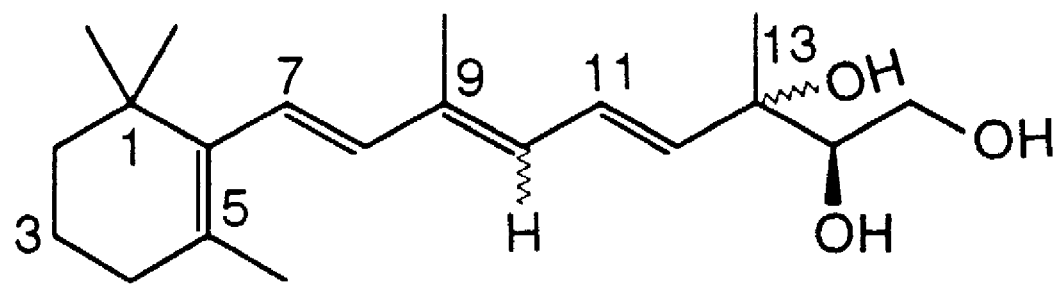
Figures 2, 31A:
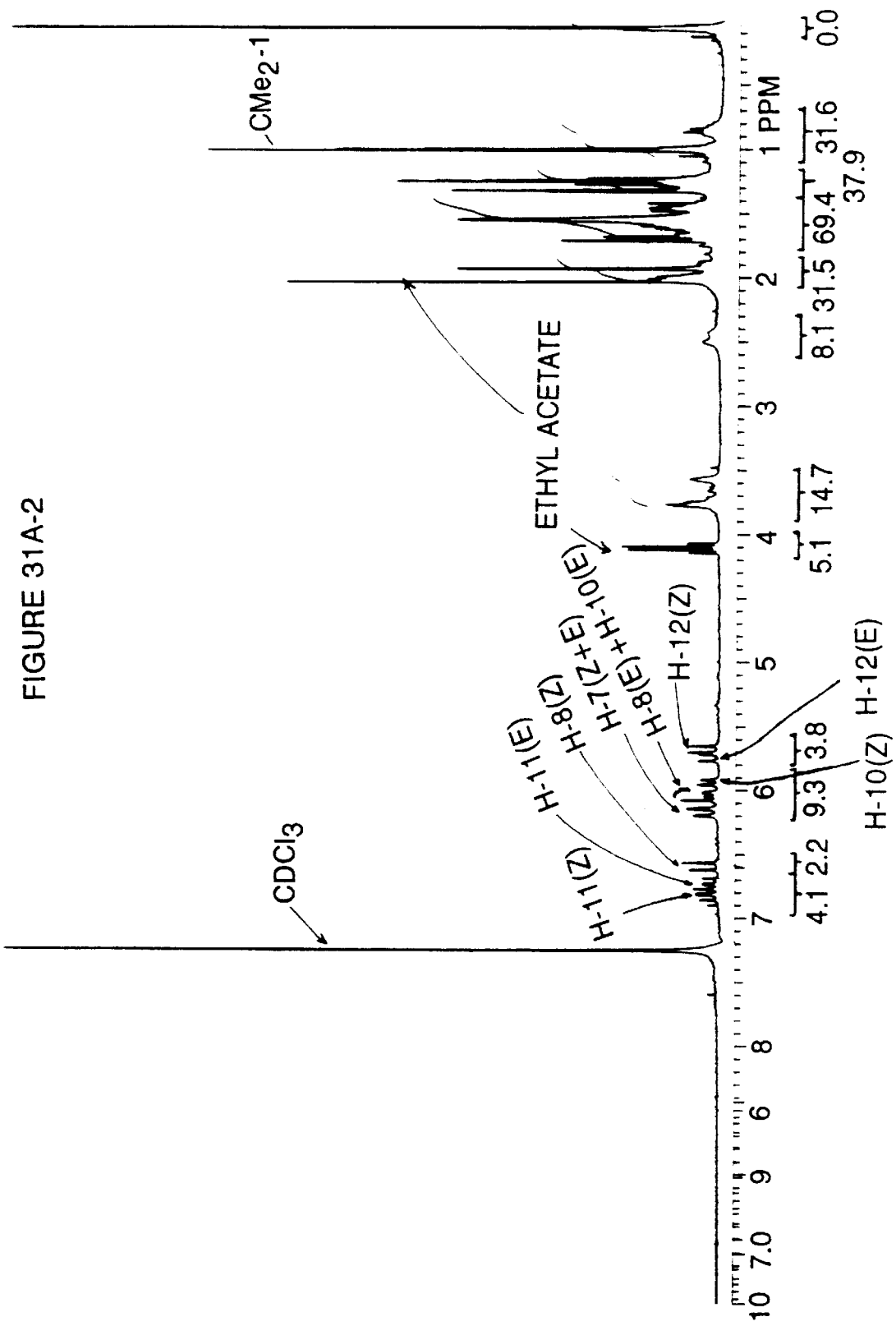
Figures 1, 31B:
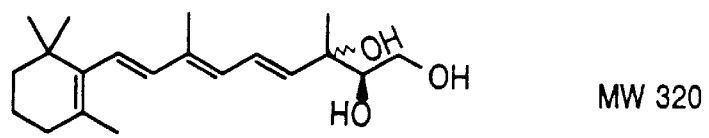
Figures 2, 31B:
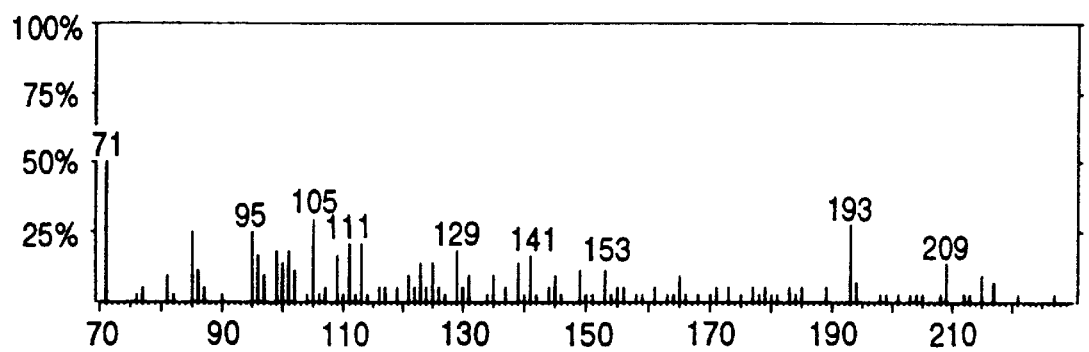
Figures 3, 31B:
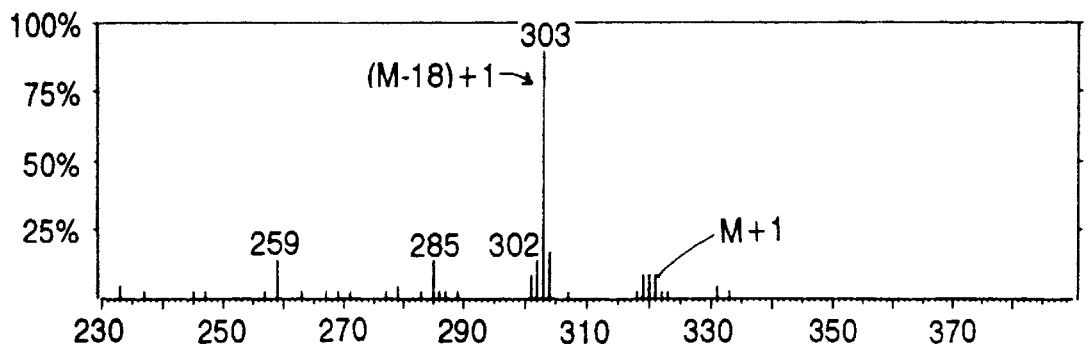

FIGS. 29C-1 and 29C-2 UV absorption of compound 12.

FIGS. 30A-1 through 30B-3 ¹HNMR: Nuclear magnetic resonance spectrum of compound 14.

FIGS. 30A-1 through 30B-3 Low resolution mass spectrum of compound 14.

FIGS. 31A-1 through 31B-3 ¹HNMR: Nuclear magnetic resonance spectrum of 13,14-DHR.

FIGS. 31B-1 through 32B-3 Low resolution mass spectrum of 13,14-DHR.

FIG. 32A-1 through 32D-2 ¹HNMR: Nuclear magnetic resonance spectrum of compound 4.

Figures 1, 32A:
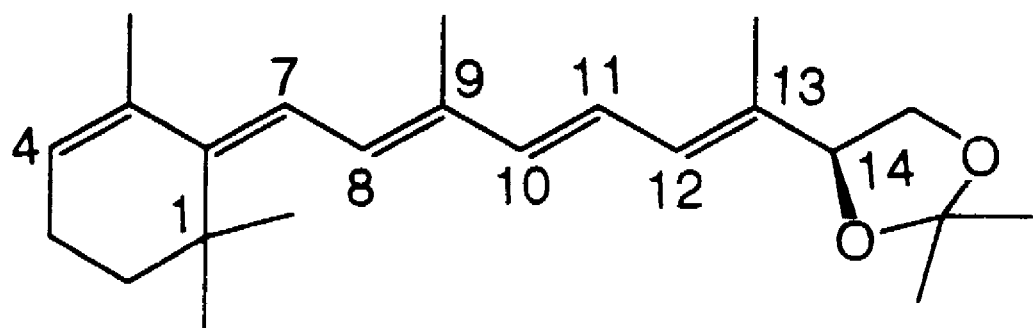
Figures 2, 32A:
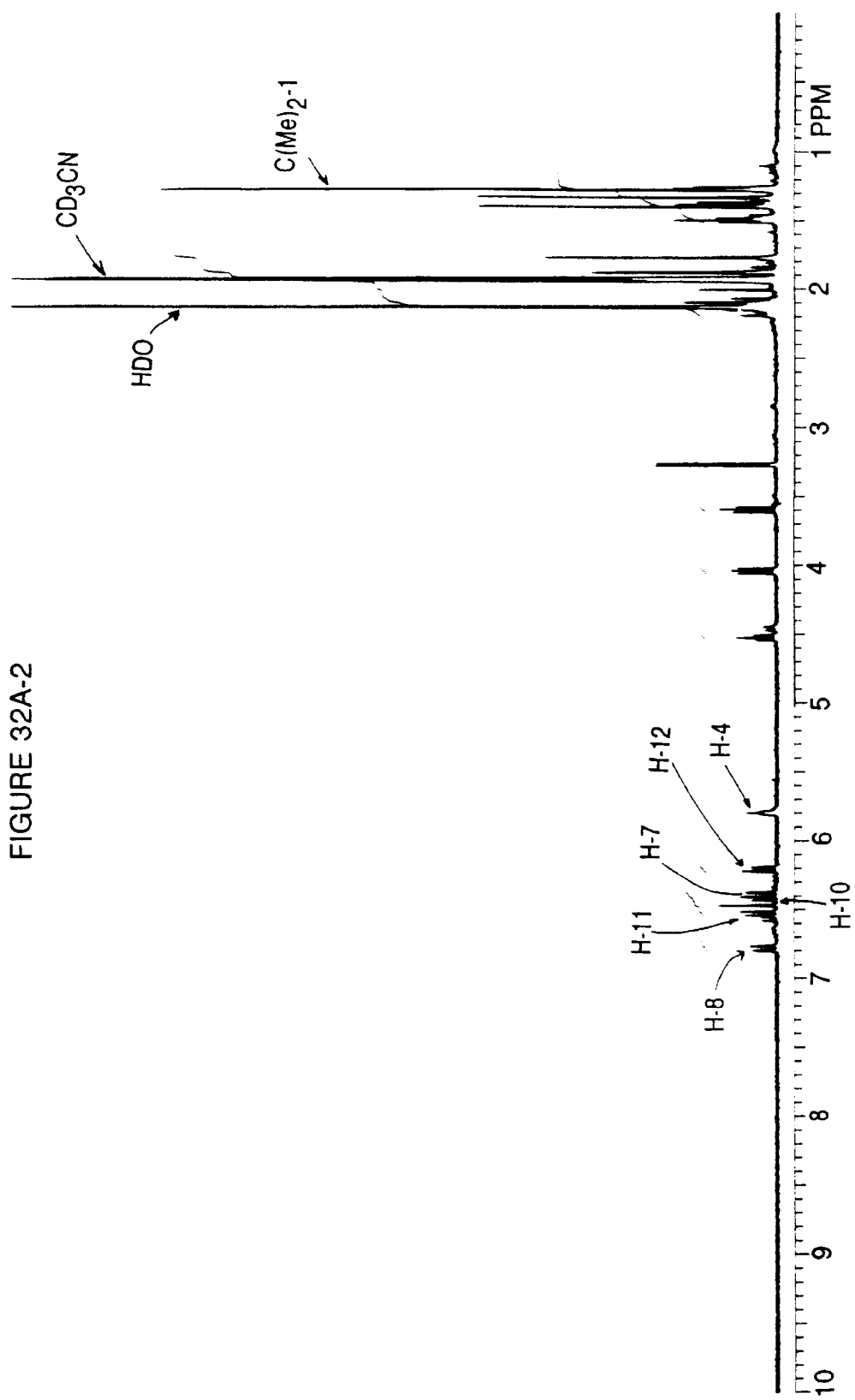
Figures 1, 32B:
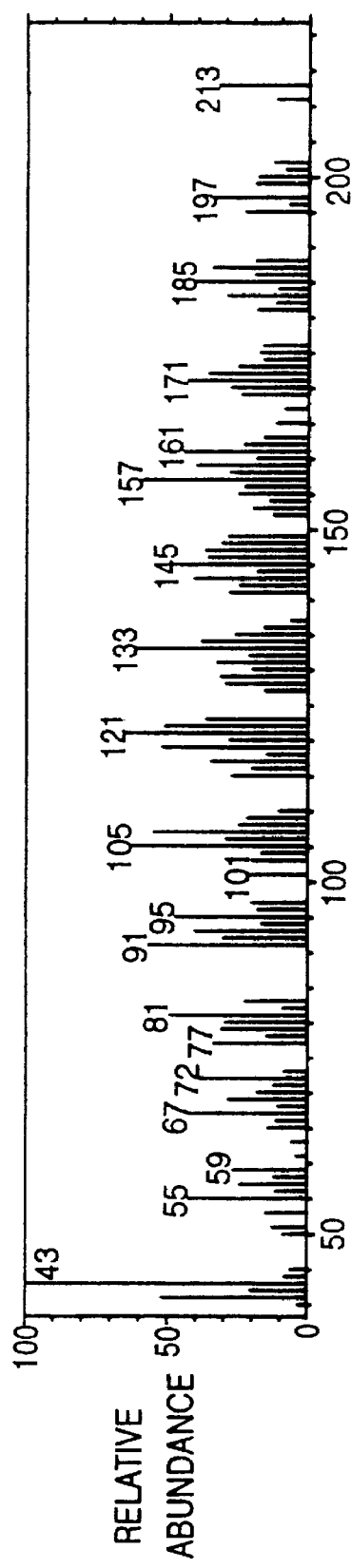
Figures 2, 32B:
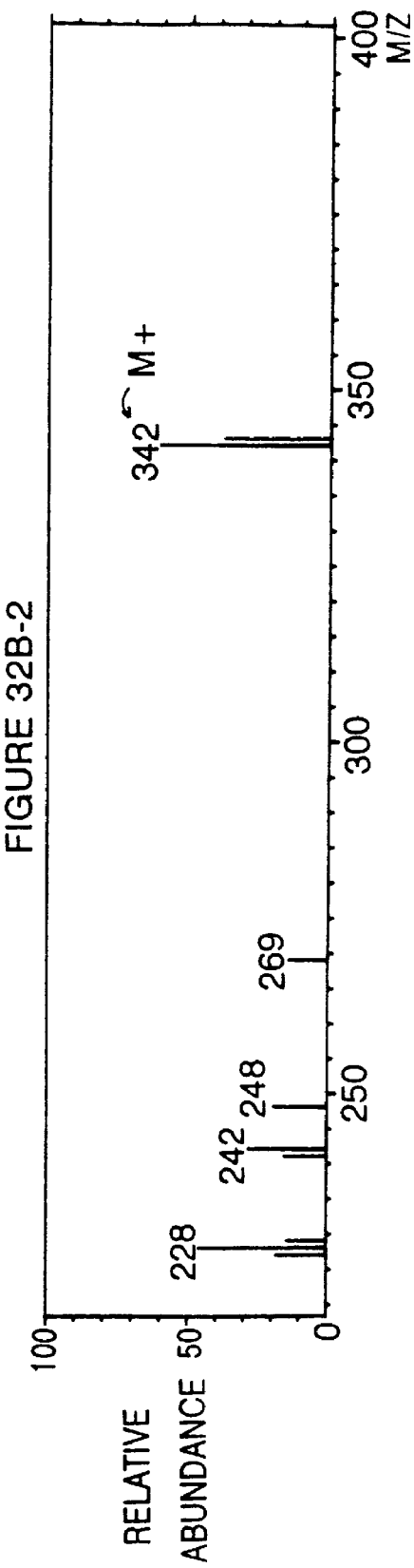
Figures 3, 32B:
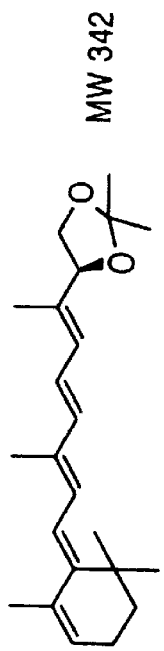

FIGS. 32B-1 through 32B-3 Low resolution mass spectrum of compound 4.

Figure 32C:
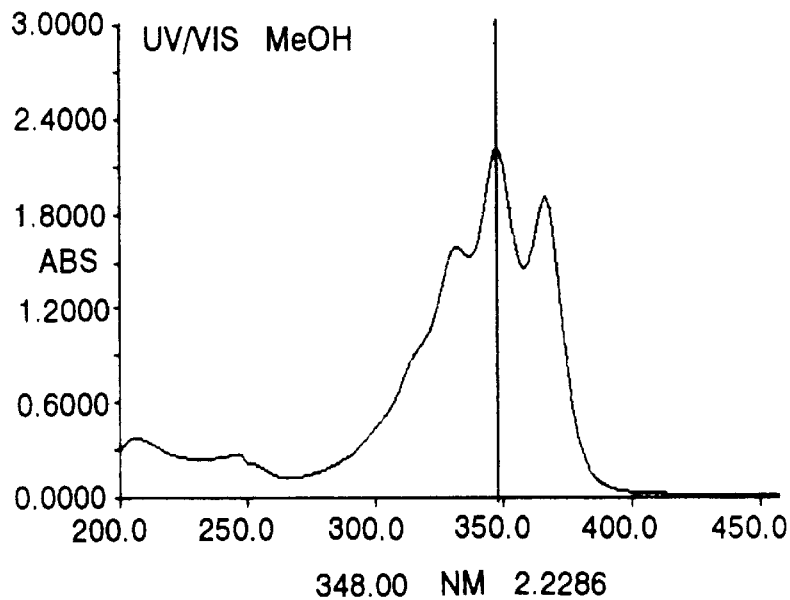

FIG. 32C UV absorption of compound 4 in methanol.

Figures 1, 32D:
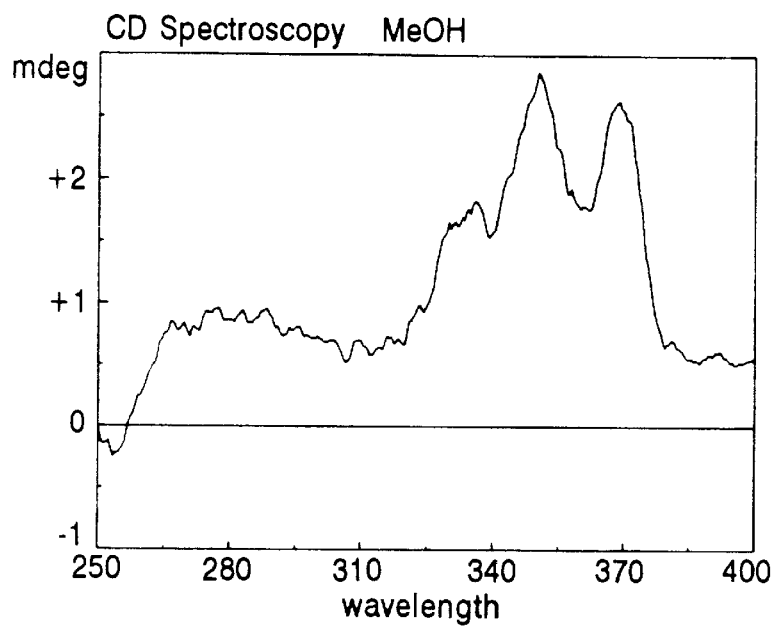
Figures 2, 32D:
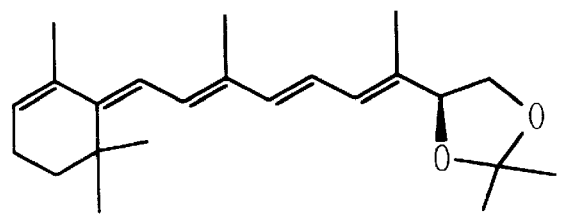

FIGS. 32D-1 and 32D-2 Circular dichroism spectrum of compound 4 in methanol.

FIGS. 33A-1 through 33B-3 ¹HNMR: Nuclear magnetic resonance spectrum of compound 9.

Figures 1, 33A:
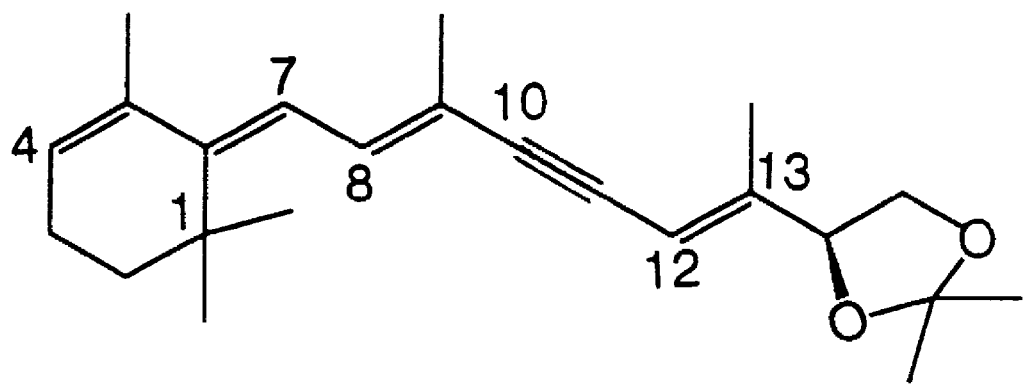
Figures 2, 33A:
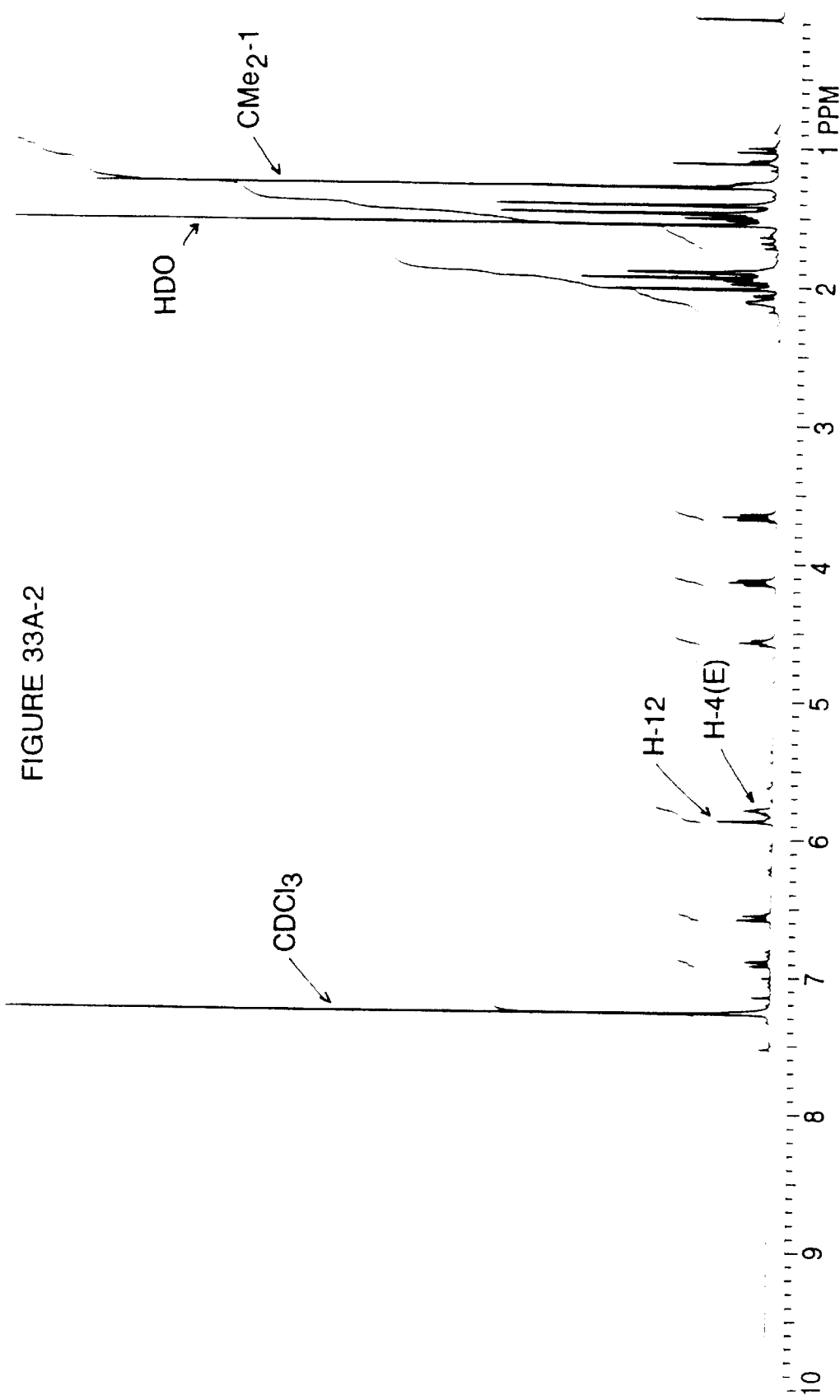
Figures 1, 33B:
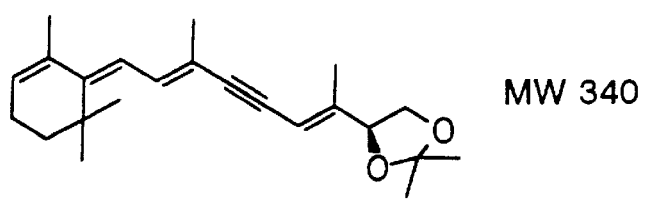
Figures 2, 33B:
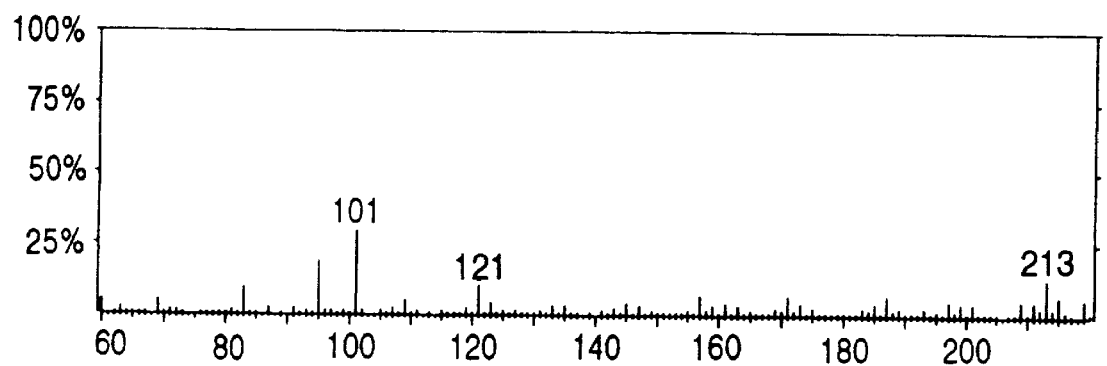
Figures 3, 33B:
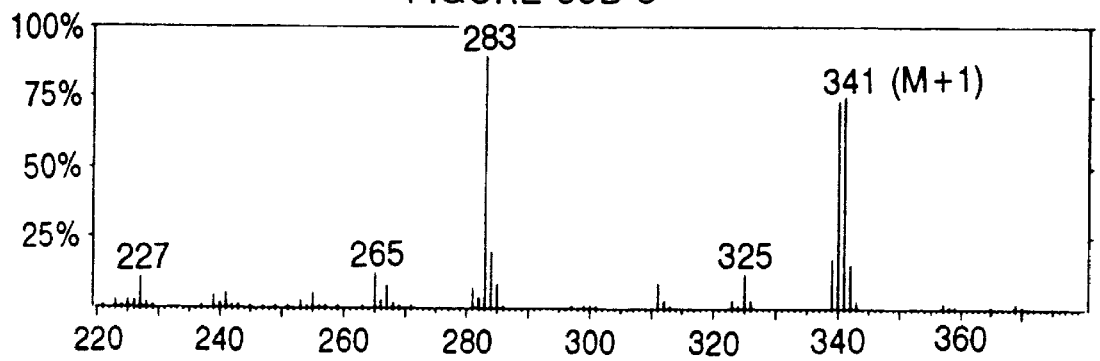

FIGS. 33B-1 through 33B-3 Low resolution mass spectrum of compound 9.

FIGS. 34A-1 through 34B-3 ¹HNMR: Nuclear magnetic resonance spectrum of compound 10.

Figures 1, 34A:
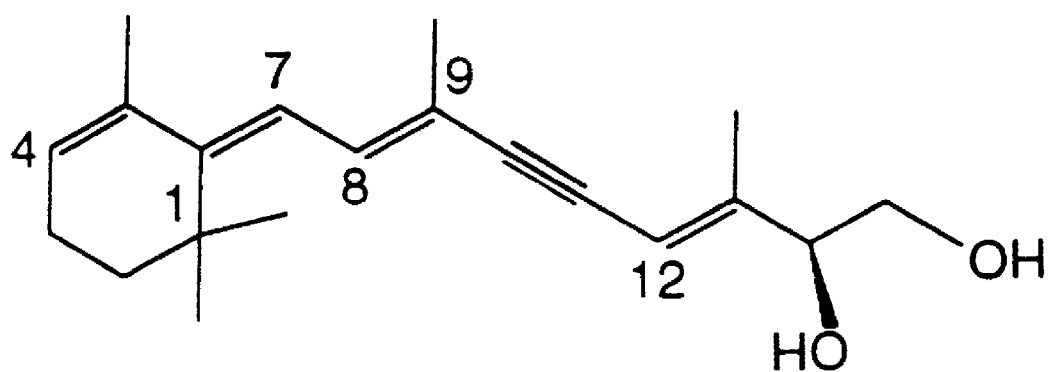
Figures 2, 34A:
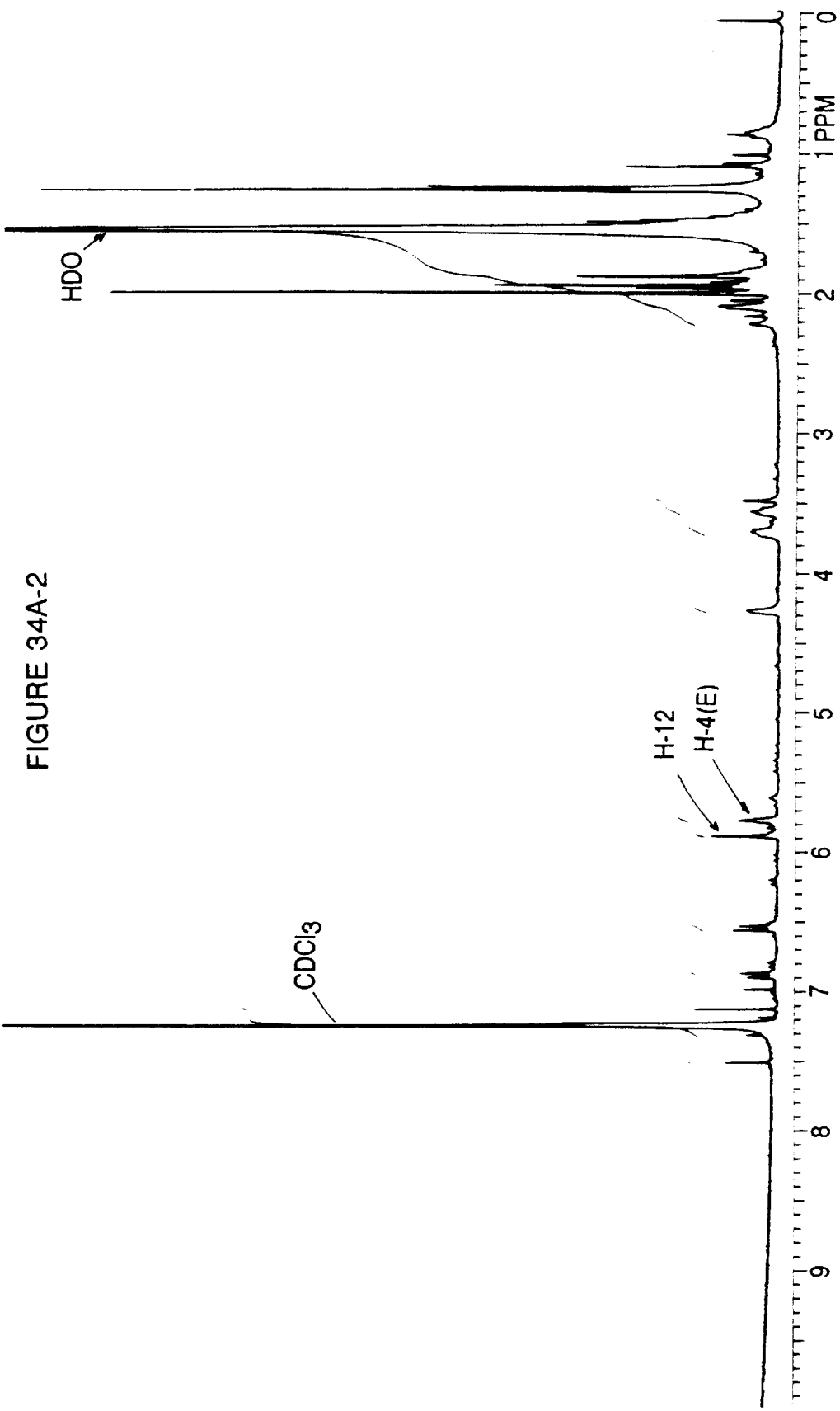
Figures 1, 34B:
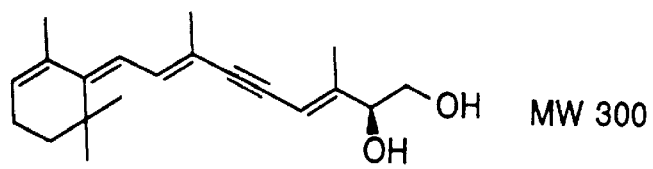
Figures 2, 34B:
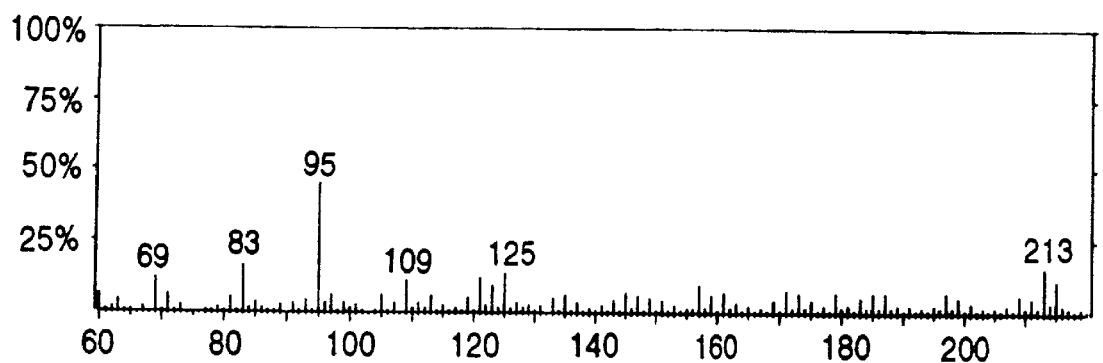
Figures 3, 34B:
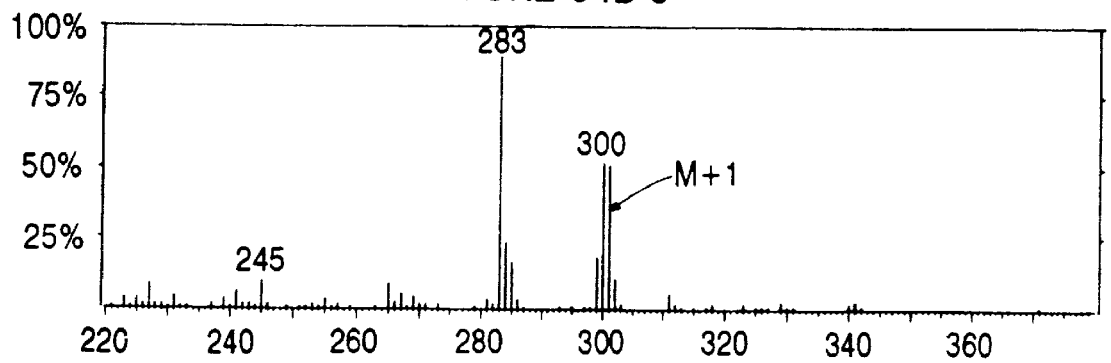

FIGS. 34B-1 through 34B-3 Low resolution mass spectrum of compound 10.

DETAILED DESCRIPTION OF THE INVENTION

This invention provides a purified retro-retinoid compound characterized by a molecular mass of about 302 daltons. The purified retro-retinoid compound of this invention is characterized by a compound having the atomic composition $C_{20}H_{30}O_2$ and having the structure:

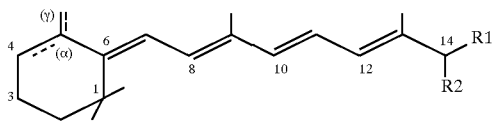

wherein the configuration of the C6, C8, C10 and C12 double bond independently is Z or E; and R1 is $CH_2OH$ and R2 is OH. However, in the preferred embodiment, the C6 double bond is trans. As used herein, the term "compound" shall mean all isomeric forms of the above compound as well as all homologs and analogs thereof. This compound may be purified from natural sources or chemically synthesized.

This invention also provides a pharmaceutical composition which comprises the purified retro-retinoid compound described hereinabove or alternatively, a synthetic product of the compound, and a pharmaceutically acceptable carrier. As used herein, the term "pharmaceutically acceptable carrier" encompasses any of the standard pharmaceutically carriers, such as a phosphate buffered saline solution, water, and emulsions such as an oil/water emulsion, and various types of wetting agents. In the preferred embodiment of the invention, the pharmaceutically acceptable carrier also comprises specific binding proteins, which may be, but are not limited to retinol binding protein (RBP), transthyretin (TTR), the complex formed by RBP and TTR, or albumin. Most specifically, the complex composition shall have a ratio of 4:1:1 with respect to RBP, TTR and the retro-retinol compound and a concentration of about 10 to about 100 µg/ml. Albumin is at a concentration of 1 milligram per milliliter. Most preferably, the carrier is a retinol binding protein.

This invention also provides a method for obtaining the purified retro-retinoid compound described hereinabove which comprises growing a suitable cell line under suitable conditions, contacting the grown cells with $10^{-5}$M all-trans retinol, extracting the cell pellet or the culture fluid with organic solvents such as, but not limited to, butanol, acetonitrile ethyl ether, chloroform, methylene chloride, separating the organic phase from the cell pellet or culture fluid, and isolating the retro-retinoid compound by HPLC column chromatography, wherein the retro-retinoid compound elutes on a C-18 column at 83% methanol/17% water.

In the preferred embodiment of this invention, the suitable cell line is a HeLa cell line, although other mammalian and avian cell lines, such as lymphoid cells, fibroblasts, myeloid, neuroblastoma, teratoma, hepatoma and breast carcinoma can also be utilized in this method. With respect to the malignant or transformed cell lines listed above, the "normal" or non-transformed or malignant line also is useful in this method. Cell should be grown in a nutrient medium such as Eagles modified medium containing 10% bovine serum. All-trans retinol is then added. The cells are then separated from the liquid medium and washed with a neutral solution such as phosphate buffered saline (PBS). Cells should then be resuspended in the neutral solution and an organic solvent such as butanol/acetonitrile is added. The cells should be vortexed and saturated $K_2HPO_4$ is added. The cells are again vortexed and the organic phase should be separated. The compound is then isolated by a run through C-18 column preequilibrated with water, and run through with a gradient of methanol/water to yield the compound at 83% methanol/ 17% water.

This invention further provides a method of enhancing the growth of a cell in a vitamin A reduced environment which comprises contacting a cell with an effective growth enhancing amount of a compound having the structure:

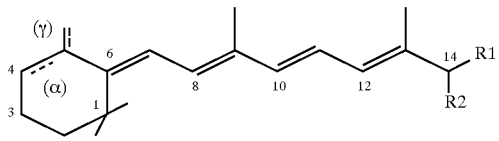

wherein the configuration of the C6, C8, C10 and C12 double bond independently is Z or E and the absolute configuration at C-14 is independently R or S; wherein R1 is alkyl, alkyl halide, alcohol, ester, ether, aldehyde, ketone, carboxylic acid, carboxylic ester, acid halide, amide, nitrile, or amine; and wherein R2 is hydroxyl, halide, alkoxy, ester, alkyl, alcohol, ether, aldehyde, ketone, carboxylic acid, carboxylic ester, nitrile, amine, azide, alkyl halide, acid halide, acid azide, or amide; or wherein R1 and R2 are replaced by a 14, 15-oxirane group; and wherein the retro structure is alpha or gamma.

As used herein, the term "enhancing the growth of a cell" means an increase of its proliferation, i.e., an increase in the cell number as a consequence of cell division. In addition, the term "vitamin A reduced environment" shall mean culture medium containing less than about $10^{-7}$M vitamin A.

The method may be practiced in vitro or in vivo. If the method is practiced in vitro, contacting may be effected by incubating the cells with the compound. The concentration of the compound is the concentration which is effective to enhance the growth of the cell as described in FIG. 8. Therefore, the effective amount is varied with the type of cell.

Another factor in determining the effective amount of the compound is the degree of vitamin A deficiency in the environment. Thus, the effective concentration of each compound will also vary with the degree of vitamin A deficiency within the cell and the amount of compensation which is to be provided by the compound.

The method of the present invention is also intended for the treatment of animals, e.g. mammals, including human patients. When the compound is to be administered in vivo, it is intended that the compound be administered as a composition comprising the compound in a pharmaceutically acceptable carrier.

Methods of the administration to animals are well known to those of skill in the art and include, but are not limited to, administration, intravenously or parenterally. Administration of the composition will be in a dosage such that the compound enhances the growth of the cell to be effected. Administration may be effected continuously or intermittently such that the amount of the composition in the patient is effective to enhance the growth of the target cell to be effected.

In the preferred embodiment of this invention, R1 is CH$_2$OH and R2 is —OH, and the C6 double bond is trans. In addition, administration of the compound is effected continuously.

This invention also provides a method for enhancing transcription of a gene regulated by retinoids in any cell which comprises contacting the cell with an effective transcription enhancing amount of a compound having the structure:

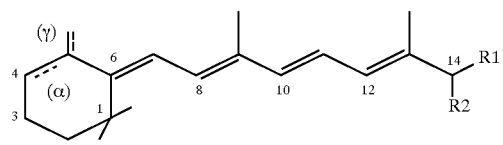

wherein the configuration of the C6, C8, C10 and C12 double bond independently is Z or E and the absolute configuration at C-14 is independently R or S; wherein R1 is alkyl, alkyl halide, alcohol, ester, ether, aldehyde, ketone, carboxylic acid, carboxylic ester, acid halide, amide, nitrile, or amine; and wherein R2 is hydroxyl, halide, alkoxy, ester, alkyl, alcohol, ether, aldehyde, ketone, carboxylic acid, carboxylic ester, nitrile, amine, azide, alkyl halide, acid halide, acid azide, or amide; or wherein R1 and R2 are replaced by a 14, 15-oxirane group; and wherein the retro structure is alpha or gamma.

As used herein, the term "enhancing transcription of a gene" is defined as the accelerated production of messenger RNA in cells. C-fos and CD-38, two examples of genes which are regulated by retinol and therefore, whose transcription may be enhanced by the use of the claimed method.

As used herein, the term contacting, is to mean contacting in vitro or in vivo. Methods of in vitro and in vivo contacting are described hereinabove. The effective amount of a compound is the amount which enhances transcription of certain genes in the cell and will vary with the type of cell as well as the gene to be regulated. Methods of determining the effective amount are well known to those of skill in the art.

This invention also provides a method for enhancing an immune response which comprises administering to the subject an effective immune-enhancing amount of a compound having the structure:

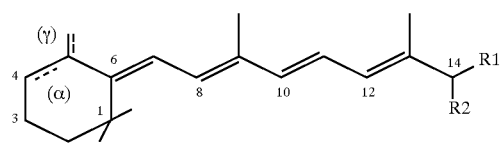

wherein the configuration of the C6, C8, C10 and C12 double bond independently is Z or E and the absolute configuration at C-14 is independently R or S; wherein R1 is alkyl, alkyl halide, alcohol, ester, ether, aldehyde, ketone, carboxylic acid, carboxylic ester, acid halide, amide, nitrile, or amine; and wherein R2 is hydroxyl, halide, alkoxy, ester, alkyl, alcohol, ether, aldehyde, ketone, carboxylic acid, carboxylic ester, nitrile, amine, azide, alkyl halide, acid halide, acid azide, or amide; or wherein R1 and R2 are replaced by a 14, 15-oxirane group; and wherein the retro structure is alpha or gamma and a pharmaceutically acceptable carrier. In the preferred embodiment of this invention, R1 is CH$_2$OH and R2 is —OH and the C6 position is trans. This method is effective for enhancing the subject's cellular immune response as well as the subject's humoral immune response. As used herein, the definition of the terms "cellular immune response" and "humoral immune response" are known to those of skill in the art. For the purposes of this invention, the subject may be, but is not limited to, an animal, such as a mammal, or a human patient.

It is contemplated that this invention is to be practiced in vivo. Accordingly, an effective amount is an amount which is effected to enhance the immune response of the subject. Accordingly, the effective amount will vary with the subject being treated, as well as the condition to be treated. For the purposes of this invention, the methods of administration are to include, but are not limited to, administration intravenously or parenterally.

The present invention also provides a purified retinoid compound characterized by a molecular mass of about 320 daltons and an atomic composition of C$_{20}$H$_{32}$O$_3$.

This invention also provides a purified retinoid compound having the structure:

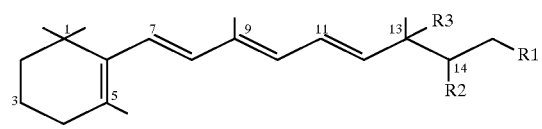

wherein the configuration of the C7, C9, and C11 double bond independently is Z or E. The absolute configuration at C13 and C14 is independently R or S. However, in the preferred embodiment, the three double bonds are trans. R1 is alkyl, alkyl halide, alcohol, ester, ether, aldehyde, ketone, carboxylic acid, carboxylic ester, acyl halide, amide, nitrile, or amine; R2 and R3 are independently hydroxyl, halide, alkoxy, ester, alkyl, alcohol, ether, aldehyde, ketone, carboxylic acid, carboxylic ester, nitrile, amine, azide, alkyl halide, acid halide, acid azide, or amide; or wherein R2 and R3, or R1 and R2 are replaced by a 13,14-oxirane or 14,15-oxirane group, respectively. As used herein, the term "compound" shall mean all isomeric forms of the above compound as well as all homologs and analogs thereof. This compound may be purified from natural sources or chemically synthesized. The preferable compound is where R1, R2 and R3 are hydroxyl groups.

This invention also provides a pharmaceutical composition which comprises the purified retinoid compound described directly above or alternatively, a synthetic product of the compound, and a pharmaceutically acceptable carrier.

As used herein, the term "pharmaceutically acceptable carrier" encompasses any of the standard pharmaceutically carriers, such as a phosphate buffered saline solution, water, and emulsions such as an oil/water emulsion, and various types of wetting agents. In the preferred embodiment of the invention, the pharmaceutically acceptable carrier also comprises specific binding proteins, which may be, but are not limited to retinol binding protein (RBP), transthyretin (TTR), the complex formed by RBP and TTR, or albumin. Most specifically, the complex composition shall have a ratio of 4:1:1 with respect to RBP, TTR and the retro-retinol compound and a concentration of about 10 to about 100 $\mu$g/ml. Albumin is at a concentration of 1 milligram per milliliter.

The present invention also provides a growth medium comprising the compound directly above at a concentration effective to enhance cell growth. Such types of growth media include, but are not limited to, a basal medium known in the art (e.g. RPMI 1640 amino acid/salt mixture, insulin, transferrin, albumin and linoleic acid). Preferably, the concentration of the compound in the growth medium is about $10^{-7}$M to about $10^{-6}$M.

Also provided by the present invention is a method of enhancing the growth of cells in culture which comprises culturing the cells in the growth medium above.

This invention further provides a method of enhancing the growth of a cell which comprises contacting a cell with an effective growth enhancing amount of the compound directly above.

As used herein, the term "enhancing the growth of a cell" means an increase of its proliferation, i.e., an increase in the cell number as a consequence of cell division.

The method may be practiced in vitro or in vivo. If the method is practiced in vitro, contacting may be effected by incubating the cells with the compound. The concentration of the compound is the concentration which is effective to enhance the growth of the cell. Therefore, the effective amount is varied with the type of cell.

Another factor in determining the effective amount of the compound is the degree of vitamin A deficiency in the environment. Thus, the effective concentration of each compound will also vary with the degree of vitamin A deficiency within the cell and the amount of compensation which is to be provided by the compound.

The method of the present invention is also intended for the treatment of animals, e.g. mammals, including human patients. When the compound is to be administered in vivo, it is intended that the compound be administered as a composition comprising the compound in a pharmaceutically acceptable carrier.

Methods of the administration to animals are well known to those of skill in the art and include, but are not limited to, administration, intravenously or parenterally. Administration of the composition will be in a dosage such that the compound enhances the growth of the cell to be effected. Administration may be effected continuously or intermittently such that the amount of the composition in the patient is effective to enhance the growth of the target cell to be effected. In the preferred embodiment of this invention, the administration of the compound is effected continuously.

This invention also provides a method for enhancing an immune response which comprises administering to the subject an effective immune-enhancing amount of the compound directly above.

This method is effective for enhancing the subject's cellular immune response as well as the subject's humoral immune response. As used herein, the definition of the terms "cellular immune response" and "humoral immune response" are known to those of skill in the art. For the purposes of this invention, the subject may be, but is not limited to, an animal, such as a mammal, or a human patient.

It is contemplated that this invention is to be practiced in vivo. Accordingly, an effective amount is an amount which is effected to enhance the immune response of the subject. Accordingly, the effective amount will vary with the subject being treated, as well as the condition to be treated. For the purposes of this invention, the methods of administration are to include, but are not limited to, administration intravenously or parenterally.

This invention also provides a method for enhancing transcription of a gene regulated by retinoids in any cell which comprises contacting the cell with an effective transcription enhancing amount of the compound directly above.

As used herein, the term "enhancing transcription of a gene" is defined as the accelerated production of messenger RNA in cells. C-fos and CD-38, are two examples of genes which are regulated by retinol and therefore, whose transcription may be enhanced by the use of the claimed method.

As used herein, the term contacting, is to mean contacting in vitro or in vivo. Methods of in vitro and in vivo contacting are described hereinabove. The effective amount of a compound is the amount which enhances transcription of certain genes in the cell and will vary with the type of cell as well as the gene to be regulated. Methods of determining the effective amount are well known to those of skill in the art.

The present invention also provides a processing for synthesizing the compound having the structure:

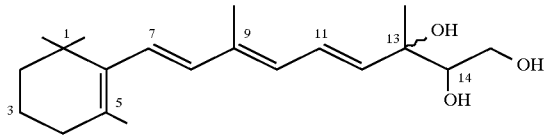

which comprises:

(a) contacting a compound having the structure:

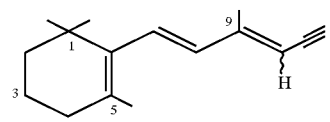

under suitable conditions with a compound having the structure:

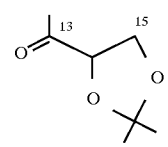

to form a compound having the structure:

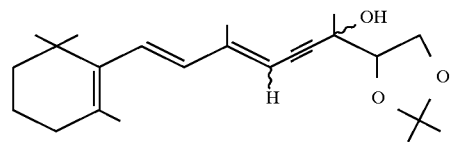

(b) reacting the compound found in step (a) under suitable conditions to form a compound having the structure:

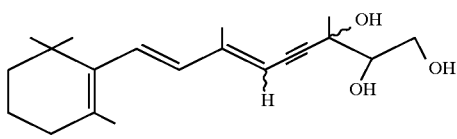

(c) reacting the compound formed in step (b) under suitable conditions to form the compound having the structure:

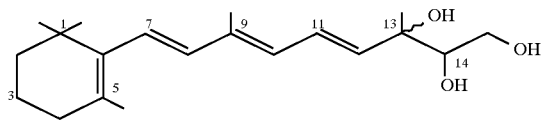

The present invention also provides a compound having the structure:

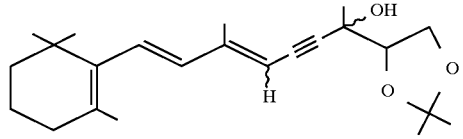

The present invention further provides a compound having the structure:

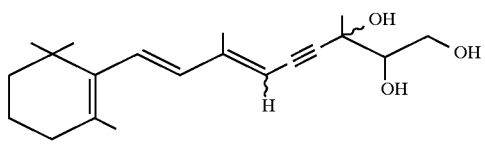

In addition, this invention provides a method for obtaining the purified retinoid compound described hereinabove which comprises growing a suitable cell line under suitable conditions, contacting the grown cells with retinol to form a cell pellet, extracting the cell pellet or the culture fluid with a suitable organic solvent such as, but not limited to, butanol, acetonitrile ethyl ether, chloroform, methylene chloride, and purifying the retinoid compound from the organic phase by HPLC column chromatography, wherein the retinoid compound elutes on a C-18 column (Vydac) at 81% methanol/19% water.

In the preferred embodiment of this invention, the suitable cell line is a HeLa cell line, although other mammalian and avian cell lines, such as lymphoid cells, spleen cells, fibroblasts, myeloid, neuroblastoma, teratoma, hepatoma and breast carcinoma may also be utilized in this method. With respect to the malignant or transformed cell lines listed above, the "normal" or non-transformed or malignant line also is useful in this method. Cell should be grown in a nutrient medium such as Eagles modified medium containing 10% bovine serum ITLB medium. Retinol is then added. The cells are then separated from the liquid medium and washed with a neutral solution such as phosphate buffered saline (PBS). Cells should then be resuspended in the neutral solution and an organic solvent such as butanol/acetonitrile is added. The cells should be vortexed and saturated $K_2HPO_4$ is added. The cells are again vortexed and the organic phase should be separated. The compound is then isolated by a run through C-18 column preequilibrated with water, and run through with a gradient of methanol/water to yield the compound at 81% methanol/19% water.

The present invention also provides a pharmaceutical composition which comprises 14-hydroxy-4,14-retro-retinol and a retinol binding protein.

Also provided by this invention is a compound having the structure:

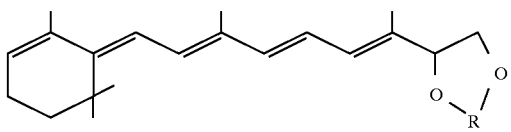

wherein R is $C(Me)_2$ or $Si(tButyl)_2$.

The present invention further provides a compound having the structure:

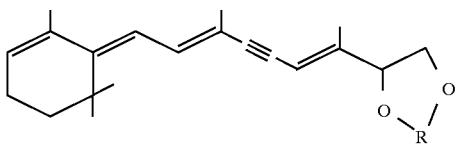

wherein R is $C(Me)_2$ or $Si(tButyl)_2$.

The present invention still further provides a compound having the structure:

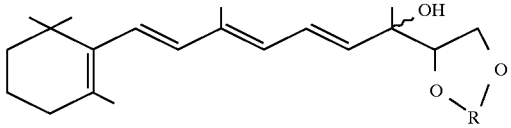

wherein R is $C(Me)_2$ or $Si(tButyl)_2$.

Lastly, the present invention provides a compound having the structure:

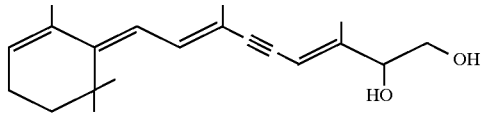

This invention is illustrated in the Experimental Details section which follows. This section is set forth to aid in an understanding of the invention but is not intended to, and should not be construed to, limit in any way the invention as set forth in the claims which follow.

EXPERIMENTAL DETAILS

Example A

Materials and Methods

Retinoids

Ro-10-1670 (Etretine, Ro 13-7410 (TTNPB), Ro 40-6085 (AM 80), and 3,4,-didehydroretinol were generous gifts of Hoffman-LaRoche, Inc. Nutley, N.J. 3,4-didehydroretinol was oxidized to 3,4-didehydroretinal and 3,4-didehydroretinoic acid according to the procedure of Mayer et al. (21). Retinyl esters were a gift of Dr. W. Blaner, Columbia University, N.Y. All other unlabeled retinoids used were purchased from Sigma Chemical Co. (St. Louis, Mo.). [$^3$H] retinol was purchased from Amersham, Arlington Heights, Ill. and was >98% pure according to HPLC analysis. The retinoids were dissolved in methanol/chloroform (3:1) (vol/vol) at a concentration of $3\times10^{-2}M$ with $10^{-4}M$ butylated hydroxytoluene (BHT) (Sigma Chemical Co.)

added and stored in the dark at −20° C. in a nitrogen atmosphere. Immediately before bioassays, the stock solutions were diluted in serum-free medium.

Cell Lines

The human EBV-transformed B-cell line 5/2 was established from the peripheral blood of a healthy donor. The cell line was grown in RPMI 1640 supplemented with 8% fetal calf serum, L-glutamine (2 mM), and antibiotics. The cell line was tested regularly for mycoplasma infections and was consistently negative.

Synthesis of Retroretinol

Retroretinol is prepared by treatment of retinal enolacetate with $NaBH_4$, and can be converted to retroretinyl acetate by acetylation of retroretinol (18). Retroretinyl acetate has also been prepared by treatment of retinyl acetate with aqueous HBr (19). Retrovitamin A methyl ether was synthesized in 1952 (20). Derivations of the above may be synthesized by methods well known to those of skill in the art.

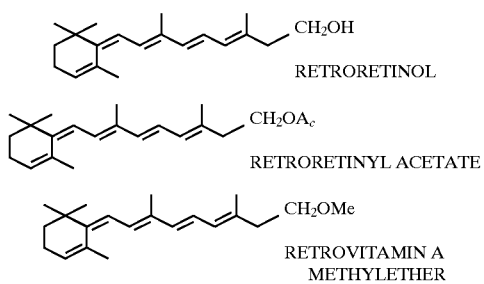

Chemical Synthesis of 14 hydroxy retro-retinol (14HRR)

Route 1

Compound 2 (below) is prepared from 2,6,6-trimethylcyclohexenone 1 according to methods well known by those of skill in the art (21). Intermediate 3 is synthesized from commercially available (R) or (S) glyceraldehyde.

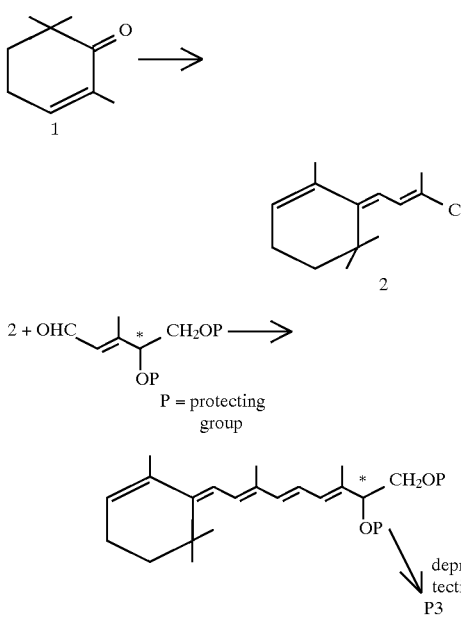

-continued

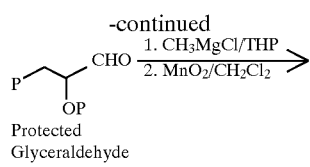

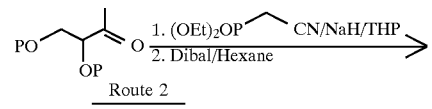

Route 2

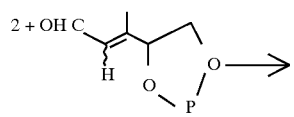

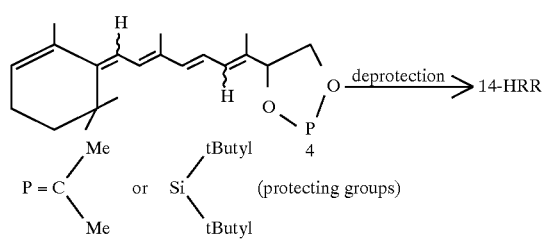

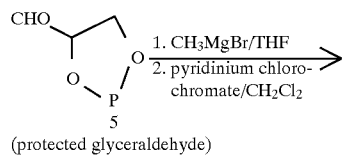

Route 3

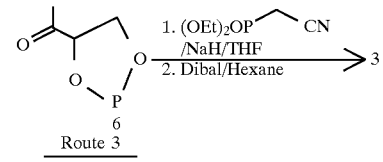

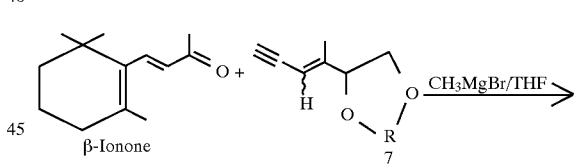

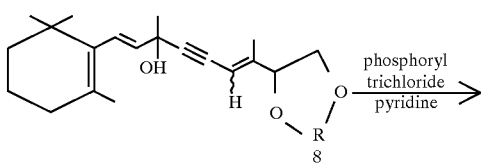

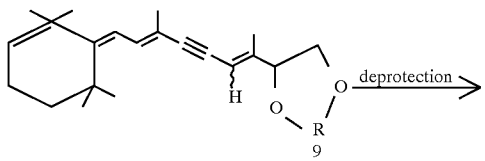

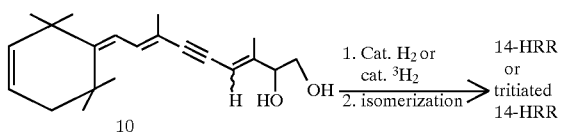

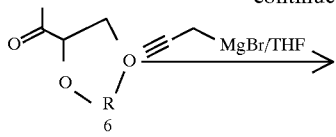

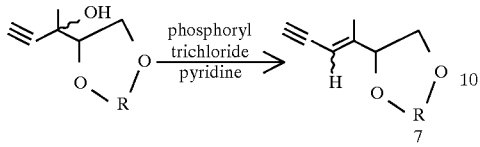

Intermediate 7 can be obtained from R or S compound 6 (see Route 1)

Route 4

Conversion of 13,14DHR (or synthetic precursors of 13,14-DHR) to 14-HRR.

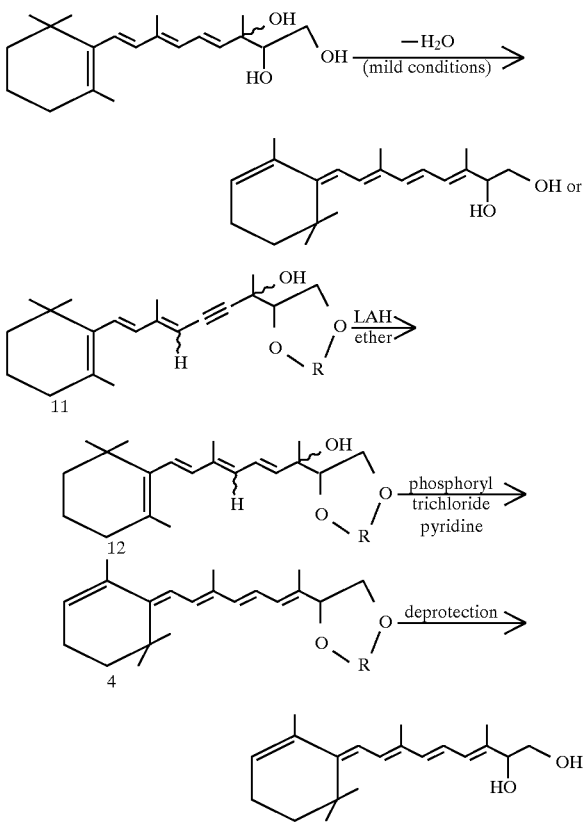

The synthesis of 14-HRR may be carried out using the four routes starting with (R)-glyceraldehyde-acetonide (R=CMe$_2$ in 5; see ref. 59 and 60).

The proton NHR and mass spectra of compounds 4, 10, 11, and 12 are shown in FIGS. 32, 34, 27 and 28, and 29, respectively. For the synthesis of 11, see later section dealing with synthesis of 13,14-DHR.

Cell Proliferation Assay

The assay system is a modification of the assay developed by Blazar et al. (12). Specifically, cells taken from their exponential growth phase were washed twice and seeded with or without retinoids at graded cell concentrations in serum-free HB 101 medium (Hana Biologics, Berkeley, Calif.) or in FCS containing RPMI medium. Assays were done in 96 well microtiter plates in a final volume of 200 μl/well or in 25 cm$^2$ tissue culture flasks. The cells in the microtiter plates were cultured for 72 hours and cell growth was determined by labeling for the last 16 hours with 0.8 μCi/well of [$^3$H]thymidine (sp. act. 6.7 Ci/mmol). Growth in the culture flasks was determined in three aliquots of 100 μl taken at 24 hours intervals and cultured in the presence of 0.8 μCi of [$^3$H]thymidine for an additional 6 hour period. To determine the viable cell number, nine aliquots per time point were differentially counted in a Neubauer chamber in the presence of trypan blue.

Purification of 14 hydroxy retro-retinol (14HRR)

HeLa cells were grown in spinner flasks in Eagles modified medium containing 10% bovine serum to a density of 7×10$^5$ cells/ml. 10$^{-5}$M all-trans retinol (Sigma) was added 16 hours before harvesting the cells. The cells were spun down and washed with phosphate buffered saline (PBS). 12 ml of packed cells were resuspended in 24 ml PBS and 9.6 ml-butanol/acetonitrile 1:1 (v/v) was added. After vortexing for one minute, 7.2 ml of a saturated K$_2$HPO$_4$ was added. The mixture was vortexed again for one minute, and the organic phase were separated by centrifugation at 8000 rpm for 10 minutes.

The organic phase was diluted with an equal volume of water and loaded on a preparative C-18 HPLC column (Vydac) which was preequilibrated with water. The column was eluted with a gradient of water to methanol. 14HRR eluted at 83% methanol/17% water as determined by the characteristic absorption spectrum in the photodiode array detector. The 14HRR-containing fraction was rechromatographed on a semipreparative C$_{18}$ column (Vydac) using as eluant a linear gradient of water to acetonitrile. 14HRR eluted at 25% water, 75% acetonitrile.

To concentrate 14HRR, the purified material from the semipreparative C18 column was loaded on an analytical C4 column (VYDAC) and eluted with a linear gradient water to methanol. 14HRR eluted at 28% water, 72% methanol. 10$^{11}$ HeLa cells yielded 25 optical units of 14HRR at 348 nm. This material was analyzed by NMR.

RNA and DNA Staining

To analyze cell progression through the cell cycle, cells were stained with acridine orange (Polysciences Inc., Warrington, Pa.). In brief, 0.4 ml of acid detergent (0.1% Triton X-100; 0.08N HCl; 0.15M NaCl) was added to 0.2 ml of the cell suspension. Thirty seconds later, 1.2 ml of acridine orange staining solution (6.0 ug/ml acridine orange, 10$^{-3}$M EDTA, 0.15M NaCl, 0.1M citrate-phosphate buffer at pH 6) was added to each sample. Cells were measured immediately using a FC200 flow cytometer (Ortho Diagnostics, Westwood, Mass.) as described (19,20). The red (600 to 640 nm) and green (515 to 575 nm) luminescence emissions from each cell were optically separated, measured by separate photomultipliers, and the data collected and stored in a Compaq Deskpro 386 computer. The number of cells in G$_1$, S and G$_2$+M cell cycle compartments were calculated using interactive computer programs.

Results

Lymphoblastoid 5/2 cells grown in the presence of 10$^{-6}$M retinol were spiked with $^3$H-labeled retinol. After 16 hours the cell pellet was delipidated according to the method of McLean et al. and separated on a reversed phase C-18 HPLC column (FIG. 7). By comigration with standards, 13-cis retinol, all-trans retinol, and several retinyl esters were identified. Retinoic acid, 3,4-didehydroretinol acid as well as 3,4-didehydroretinol were not detectable. Three peaks, P1, P2 and P3, could not be immediately identified. One peak eluting at 36–39 minutes (corresponding 83% methanol 7% water) provisionally called P3, but now known as 14HRR, was unusual because unlike P1 eluting at 31–34 minutes, its relative amount increased when the retinol concentration was lowered or when retinol was given to the cells bound to RBP. 14HRR was tested in the B-cell growth assay and found it was active and capable of replacing retinol (FIG. 8). Since HeLa cells contain 14HRR, these cells were also used. 50 ml of packed HeLa cells ($10^{10}$ cells) yielded 25 $OD_{348nm}$ units of pure P3 after the following sequence of steps: 1. Growth in the presence of $10^{-5}M$ retinol; 2. Extraction of cell pellet according to McClean et al. (13); 3. Preparative C-18 HPLC column eluted with a water/methanol gradient; 4. semipreparative $C_{18}$ HPLC column eluted with a water/acetonitrile gradient; 5. analytical $C_4$ column eluted with a water/methanol gradient. P3 is unstable in chloroform and does not survive an acid extraction step. P3 displayed an absorption with a fine structure and absorption maxima at 326.

An EI mass spectrum of 14HRR was obtained. This spectrum (FIG. 11B) indicated the presence of a compound with a molecular mass of 302 daltons. High resolution mass spectroscopy showed a mass of 302.2265, which is consistent with an atomic composition of $C_{20}H_{30}O_2$. This means that P3 not only has a retro structure but an additional oxygen atom as compared with its precursor retinol.

Proton NMR confirmed the features of 14-hydroxy-retro-α-retinol structure. 14HRR is bioactive down to a concentration of $10^{-8}M$. It is 10 to 15 times more potent than retinol on a molar basis, but unlike retinol, cultures have to be replenished daily with 14HRR. This is due either to chemical instability or to a more rapid metabolic degradation of 14HRR by the cells.

The use of $^3H$ retinol bound to fetal calf serum was used as an assay to test for 14HRR in other cell lines. All 26 mammalian cells tested results of 13 cells lines shown in Table 1, radioactivity peak at the position where 14HRR normally elutes. In the instances tested, the material in this peak also showed the characteristic UV spectrum of 14HRR.

TABLE I

Retinol metabolism of 13 selected cell lines

| Cell type cts. | Line | % of taken up retinol | | | |
|---|---|---|---|---|---|
| | | P3 (%) | Retinol (%) | Ester (%) | Total |
| Burkitt's lymphoma-human $\times 10^5$ | Raji 4° | 0 | 99 | 0 | 2.5 |
| $\times 10^5$ Lymphoblastoid | Raji 37° | 3 | 79 | 14 | 4.0 |
| cells-human $\times 10^5$ | 5/2 | 4 | 67 | 24 | 5.7 |
| cells-human $\times 10^5$ | Ket | 3 | 52 | 41 | 4.6 |
| Leukemia (ALL) $\times 10^5$ human | SKL3 | 2 | 71 | 24 | 1.6 |
| Leukemia (ALL) $\times 10^5$ | RPMI | 2 | 58 | 38 | 1.2 |
| Leukemia, pre-B $\times 10^5$ mouse | SLA | 3 | 85 | 9 | 6.1 |
| Leukemia, T-Cell $\times 10^5$ mouse | EL-4 | 5 | 40 | 44 | 2.8 |
| Leukemia, T-Cell $\times 10^5$ | ERLD | 9 | 63 | 20 | 2.8 |
| Monocytic $\times 10^5$ leukemia mouse | P388D.1 | 0.5 | 71 | 26 | 1.4 |
| B-cell hybridoma $\times 10^5$ | SK3886 | 3 | 92 | 2 | 4.7 |
| Cervical $\times 10^5$ carcinoma-human | Hela | 3 | 71 | 20 | 1.0 |
| Teratocarcinoma $\times 10^5$ human | N-tera2 | 0.4 | 0.7 | 97 | 13.5 |
| Neuroblastoma $\times 10^5$ human | SK—N—SH | 0.9 | 56 | 25 | 2.0 |

Legend: $2.5 \times 10^6$ cells were grown overnight in 5 ml RPMI/10% FBS. The FBS was preincubated at room temperature with 14.4 uCi [$^3H$] retinol (NEN) for 4h. The cell pellet was washed twice with PBS. The retinoid were extracted according to MClean et al. 90 and separated on an analytical $c_{18}$ reverse phase column according to FIG. 7. The DPM were determined using an on-line scintillation counter.

Example B

SUMMARY

Murine thymic T cells depleted of antigen-presenting cells proliferate poorly in response to crosslinking anti-CD3 mAb or Con A when cultured in conventional FCS-containing serum. However, in a serum-free medium formulated to contain, in addition to basic ingredients, insulin, transferrin, albumin, linoleic acid and retinol, proliferation is vigorous. The presence of retinol is critical, because when omitted, cells do not become activated. The subsets of T cells proliferating with the assistance of retinol cofactor are both $CD4^+$ and $CD8^+$ thymic T cells, and $CD4^+$ peripheral T cells. Mature $CD8^+$ T cells of lymph nodes can also be activated in ITLB medium plus retinol, provided that IL-2 is added. Retinol needs to be present at the time when TCR triggering is initiated, suggesting that early activation events ($G_0$ to $G_1$ transition) are dependent on retinol. It is currently less clear whether or not subsequent events associated with $G_1$ to S phase transition also require the presence of retinol. 14-hydroxy-retro-retinol is a metabolic product of retinol in lymphocytes, and this retinoid effectively supports T cell activation in conjunction with a mitogen in lieu of retinol. Thus, while retinol and its intracellular product, 14HRR, are unable to activate T cells on their own, they are important cofactors. The requirement for retinol in CD3-mediated T cell activation cannot be satisfied by retinoic acid or interleukins 1, 2, 4 and 6, and TNF-alpha whereas IFN-gamma can substitute for retinol. Our experiments are compatible with the idea that retinol, in the course of cellular activation, is converted to 14HRR which is needed as intracellular messenger. If substantiated by molecular studies now underway, our data should lead to the description of a new signal pathway distinct from the retinoic acid signal pathway observed in non-lymphoid cells, but perhaps functioning by a similar mechanism, i.e., ligand-assisted transcriptional regulation.

INTRODUCTION

The activation of resting T cells is initiated by interaction of the T cell receptor (TCR) with antigen-peptide bound to major histocompatibility complex (MHC) on antigen-presenting cells (APC). Pairs of ligand-receptor structures on the interacting cells contribute secondary signals (For review, see 22,23). While these molecular interactions have been described in considerable detail, the intracellular events ensuing are still poorly understood. However, the emerging overall picture presents multiple, interactive signal cascades that converge on the nucleus to effect transcriptional activation. As a general rule these events are mediated by two different chemical classes of molecules, proteins and small lipophilic molecules, that shuttle to the nucleus to regulate transcription. For example, the protein products of the rel gene family (e.g., NF-kB) translocate upon activation from the cytoplasm to the nucleus and regulate transcription (24). Small lipophilic molecules including the steroids, vitamin D, thyroid hormone and several forms of retinoic acids bind to and activate their specific receptors belonging to the superfamily of steroid receptors of transcriptional activation (8,24,25).

To study the requirements of T cell activation, cellular immunologists customarily use culture media supplemented with fetal calf serum (FCS). Because FCS contains a number of growth factors and hormones, including steroids, vitamin D and retinoids, it is desirable to reduce this complexity. Several serum components appear to be indispensable while others may be inhibitory, as documented recently for PDGF (26). The essential ones include albumin, thought to play a role in the stabilization and transport of fatty acids and possibly other lipids, transferrin for regulation of iron metabolism, and insulin, ostensibly for control of carbohydrate metabolism (27,28). Our laboratory has recently described retinol as a further serum constituent necessary for the growth of B lymphocytes (3). Both human and murine activated B cells perish rapidly in culture when deprived of retinal, and this may be related to earlier findings that vitamin A-deficient mammals exhibit severe defects in lymphopoiesis and immune function (29–31). The essential role of retinal for the immune system has recently been highlighted in epidemiological studies where even mild vitamin A deficiency was associated with immune dysfunction (2).

We have hypothesized that retinol serves in lymphocytes as a precursor for one or more intracellular retinoid derivatives that might mediate the retinal effects, possibly through participation in signal transduction. The analogy supporting this hypothesis is retinoic acid. This molecule is derived from retinal, passes into the nucleus of target cells and binds to specific retinoic acid receptors, leading to increased transcription of selected genes. While this mechanism is well documented for a variety of tissues and cell types, it does not apply to B lymphocytes. B cells neither produce detectable levels of retinoic acid, nor respond to it (32). We therefore performed a biochemical analysis of the intracellular retinoids of B cells and found several known retinoids (e.g., retinol and retinyl esters) and at least two hitherto undescribed retinoids. Because one of these, 14-hydroxy-retro-retinol (14HRR), was capable of supporting the proliferation of B cells in the absence of an external supply of retinal, we have speculated that this compound might serve as an intracellular mediator of retinol effects by a pathway distinct from that of retinoic acid (33). T lymphocytes also synthesize 14HRR (as indeed many other cell types studies by us) and we were therefore led to study whether T cell activation is critically dependent on 14HRR or its precursor molecule, retinal. The results reported here support this assumption.

Materials and Methods

Abbreviations: 14HRR, 14-hydroxy-retro-retinol; RBP, retinol-binding protein; TTR, transthyretin; Con A, concanavalin A; CRBP, cellular retinol-binding protein Reagents and culture medium The following antibodies were purified by protein A-sepharose chromatography: Anti-CD3e; clone 1452C11 (34), anti-I-A$^d$, clone MKD$^6$ (35); anti-IE$^d$, clone 13/18 (37); anti-Lyt2.2, clone 19/178 (38); anti-L3T4, clone GK1.5 (39) used as ascites fluid; anti-IL-4M, clone 11B11 (36). Fluorochrome labeled antibodies were from commercial sources: Anti-CD4 PE (Becton Dickinson, San Jose, Calif.); anti-CD8 FITC (Boehringer Mannheim, Indianapolis, Ind.); normal rat IgG FITC and normal rat IgG PE for controls were from Southern Biotechnology (Birmingham, Ala.).

Retinoids

All-trans retinol, all-trans retinal and all-trans retinoic acid were purchased from Sigma Chemical Co. (St. Louis, Mo.). The retinoids were dissolved at a concentration of $3 \times 10^{-2}$M in methanol or DMSO with $10^{-4}$M butylated hydroxytoluene (Sigma Chemical Co.) added and stored in the dark at $-20°$ C. in a nitrogen atmosphere. Immediately before use, the stock solutions were diluted in serum-free medium. 14-Hydroxy-retro-retinol (14HRR) was isolated from the pellets of HeLa cells fed with retinol by using a series of reversed-phase HPLC columns as described (33). 14HRR was pure according to the retention time on an analytical $C_{18}$ reversed-phase column and the typical UV absorption spectrum.

Interleukins and growth factors

Human recombinant IL-1-α was a gift from Hoffman LaRoche Co.; hrIL-2 and hrIL-6 were purchased from Boehringer Mannheim; murine rIL-4 was purchased from R&D Systems; rTNF-alpha was donated by Genentech, Inc. (San Francisco, Calif.); mouse recombinant IFN-gamma was purchased from Genzyme Corp. (Cambridge, Mass.). Bovine insulin and human transferrin were purchased from Collaborative Research (Bedford, Mass.). Delipidated bovine albumin, all-trans retinol, linoleic acid and concanavalin A were bought from Sigma (St. Louis, Mo.).

Mice

BALB/c mice of either sex were bred and housed in the Sloan-Kettering laboratory Animal Facility. Our Institution guarantees compliance with regulations promulgated by the Animal Welfare Act.

Preparation of cells

Thymuses of 3 to 6-week-old BALB/c mice were teased in serum-free RPMI medium supplemented with 1% BSA, $10^{-6}$M linoleic acid and antibiotics. Depletion of accessory cells was achieved by two cycles of complement-dependent lysis with a mixture of anti-IA$^d$ (5 μg/ml) and anti-IE$^d$ (1:500 diluted ascites fluid). Briefly, cells were incubated on ice for 30 minutes with Ia antibodies, spun down, resuspended in 1:40 diluted rabbit complement, and incubated at 37° C. for 45 minutes. Incubations and two subsequent washes were carried out with RPMI medium containing 1% BSA. Cell viability was evaluated by trypan blue dye exclusion. To determine the extent of depletion of accessory cells, samples were stained with FITC-conjugated anti-Fc receptor antibody and analyzed by flow cytometry on a FACScan instrument (Becton Dickinson). No FcR-bearing cells were detected by this procedure.

Mature T cells were obtained from pooled intestinal, axillary, inguinal and submandibular lymph nodes of 4 to 10-week-old BALB/c mice. To fractionate cells into CD4 and CD8 subsets and at the same time remove APC, a combination of adherence and complement lysis was used as follows:

The cell suspension in a volume of 2 ml was applied to a nylon wool column (40) (0.6 g of washed nylon fibers in the barrel of a 10 ml syringe) and incubated at 37° C. for 40 min. The non-adherent cells were recovered by washing with warm serum-free medium at a flow rate of 1 ml/min. The cells were then spun down and treated as described for thymocytes with two cycles of complement lysis, using either a mixture of MKD6, 13/18 and 19/178 (to obtain CD4-enriched T cells) or MKD6, 13/18 and GK1.5 (to obtain CD8-enriched T cells). The success of the enrichment procedures was monitored cytofluorimetrically using FITC-conjugated anti-CD8 and PE-conjugated anti-CD4. In either case, the T cell subsets were over 95% homogeneous. Analysis with FITC-conjugated anti-mouse IgG(k) revealed less than 2% contamination by B cells.

Proliferation assays

Cells were cultured in serum-free medium, referred to as ITLB, containing RPMI 1640 supplemented with $8 \times 10^{-7}$M insulin (5 μg/ml), $7 \times 10^{-8}$M transferrin (5 μg/ml), $2 \times 10^{-6}$M linoleic acid, $2 \times 10^{-6}$M delipidated BSA (0.12 mg/ml), 2 mM L-glutamine, 1 mM sodium pyruvate and antibiotics. They were seeded into 96-well flat-bottom plates at varying cellular densities in a final volume of 100 μl. In control experiments, cells were cultured in medium containing 10% FCS or 3% human serum and $5 \times 10^{-5}$M 2ME. T cells and thymocytes were activated with immobilized, purified anti-mAb CD3e or by the addition of Con A in the presence or absence of different concentrations of retinoids. Unless indicated otherwise, retinoids were replenished every 12 hours to maintain a reasonably constant concentration of these labile compounds in culture. The optimal concentration for stimulation of T cells was determined for each batch of anti-CD3 mAb and Con A. The optimal range of Con A was particularly narrow in serum-free medium (0.5–0.2 μg/ml) and varied with the cell density used. To assess the costimulatory activities of retinoids with other lymphokines, various concentrations of IL-1, IL-2, IL-4, IL-6, IFN-gamma and TNF-alpha were added to cultures. Cultures were carried out in duplicate. Plates were incubated at 37° C. in a humidified 5% $CO_2$ atmosphere. Cellular proliferation was determined by [$^3$H] thymidine uptake (0.5 uCi/well; New England Nuclear, Boston, Mass.) after the incubation times indicated for each experiment with a 4 hour labeling pulse. Cells were harvested onto glass filter and [$^3$H]TdR incorporation was determined by liquid scintillation counting. The data presented are the means of duplicate or six replicate cultures. The restriction to duplicate measurements was necessary to conserve scarce 14HRR. They were within 20% of each other. Each experiment was repeated at least twice.

Flow cytometry

To determine the phenotype of blast cells generated in the thymocyte cultures stimulated with immobilized anti-CD3 antibody and retinoids as well as the purity of CD4 and CD8 subsets isolated from pooled mouse lymph nodes, cells ($10^5$–$10^6$ cells/sample), stained with FITC-conjugated anti-CD4 antibody and PE-conjugated anti-CD8 antibody, were analyzed by two-color flow cytometry with a FACScan. Dead cells were eliminated by forward low-angle scatter. Isotope controls were included in all experiments. To determine the phenotype of activated thymocytes only blast cells were gated for collection and analysis.

Results

Stimulation of thymocytes with anti-CD3e in serum-free medium is dependent on the presence of retinoids Thymoctyes depleted of APC did not proliferate appreciably in response to crosslinking anti-CD3 mAb as the sole induction stimulus when cultured in FCS-containing medium (FIG. 14A). They also failed to proliferate in serum-free medium ITLB in the absence of retinoids, unless very high doses of anti-CD3 antibody (in excess of 2 μg/ml) were employed (FIG. 14B). However, in the presence of retinol at $3 \times 10^{-6}$M concentration or 14HRR at $6 \times 10^{-7}$M concentration, vigorous responses were elicited. These responses were positively correlated with cell density, but were independent over a wide dose range of the anti-CD3 concentration used to coat the plastic culture trays. Addition of 3% human serum also supported anti-CD3-initiated thymocyte proliferation, but these responses faded rapidly with decreased cell density. Growth curves of thymocyte cultures established by differential counts of cells in the presence of trypan blue showed a selective and exponential proliferation of blast cells when stimulated with anti-CD3e and retinol in combination. Anti-CD3e alone produced only a modest and transient blast transformation whereas retinol on its own produced no discernible T cell activation (FIG. 14C). When all viable cells were scored, it became evident that while the cultures as a whole declined, this decline was accelerated by anti-CD3e stimulation (representing perhaps the well-known induction of apoptosis). Surprisingly retinol by itself appeared to maintain a higher state of viability than anti-CD3e "only" stimulation, or omission of test reagents altogether. This rescue effect will have to be investigated in detail. The phenotypes of blast cells generated in the retinol- and 14HRR-supported cultures were determined by flow cytometric immunofluorescence as exclusively single positive T cells, with the approximate 70% $CD4^+$ and 30% $CD8^+$ cells (data not shown).

The proliferative responses of thymocytes were clearly dependent on the presence of all-trans retinol added at initiation of culture. Under these conditions the optimal retinol concentration was between 3 and $1 \times 10^{-6}$M (FIG. 15A). Because retinol decays in serum-free tissue culture medium with an estimated half-life of 24 hours (32), we have replenished retinol twice daily and have found that with repeated feeding, five- to ten-fold lower retinol concentrations were sufficient to sustain cell proliferation over the 3-day culture period (FIG. 14A). We have described that retinol is metabolized by lymphocytes to 14HRR and have hypothesized that this molecule serves as an intracellular mediator (33). To test this assumption in T cells, 14HRR was added instead of retinol and dose responses were recorded. A single addition of 14HRR given at the start was ineffective, probably due to the brief half-life of 14HRR of 4 hours (data not shown). However, when provided at 12 hour intervals, 14HRR was as potent as retinol in supporting T cell proliferation with a dose optimum of $5 \times 10^{-7}$M (FIG. 15A). Among other retinoids tested, 13-cis-retinol (data not shown) and all-trans retinal were equally effective as all-trans retinol. However, all-trans retinoic acid was completely inactive over a wide dose-range tested irrespectively of how often the cultures were fed.

The growth kinetics of anti-CD3-activated thymocytes in serum-free medium revealed exponential growth over a four day period (FIG. 16) that was totally dependent on the presence of either retinol ($3 \times 10^{-6}$M) or 14HRR ($6 \times 10^{-7}$M). Human serum (3%) was also capable of supporting exponential growth, although in the experiment with $10^5$ cells per well shown in FIG. 16 the proliferative indices were only half of those obtained with retinoids. Human serum contains retinol at $2 \times 10^{-6}$M. Attempts to remove retinol from serum by dilipidation and subsequently replenish it were unsuccessful.

To test whether or not activation through the TCR is unique or whether other modes of stimulation lead to proliferation sustained by retinol, we have used Con A at the optimal concentration of 0.5 μg/ml in serum-free ITLB medium. Thymocyte proliferation was entirely retinol dependent, the cultures with $3\times10^{-6}M$ retinol growing exponentially, and those without retinal perishing rapidly (FIG. 15B).

Stimulation of peripheral lymphocyte subsets is also retinol dependent.

Figure 17B:
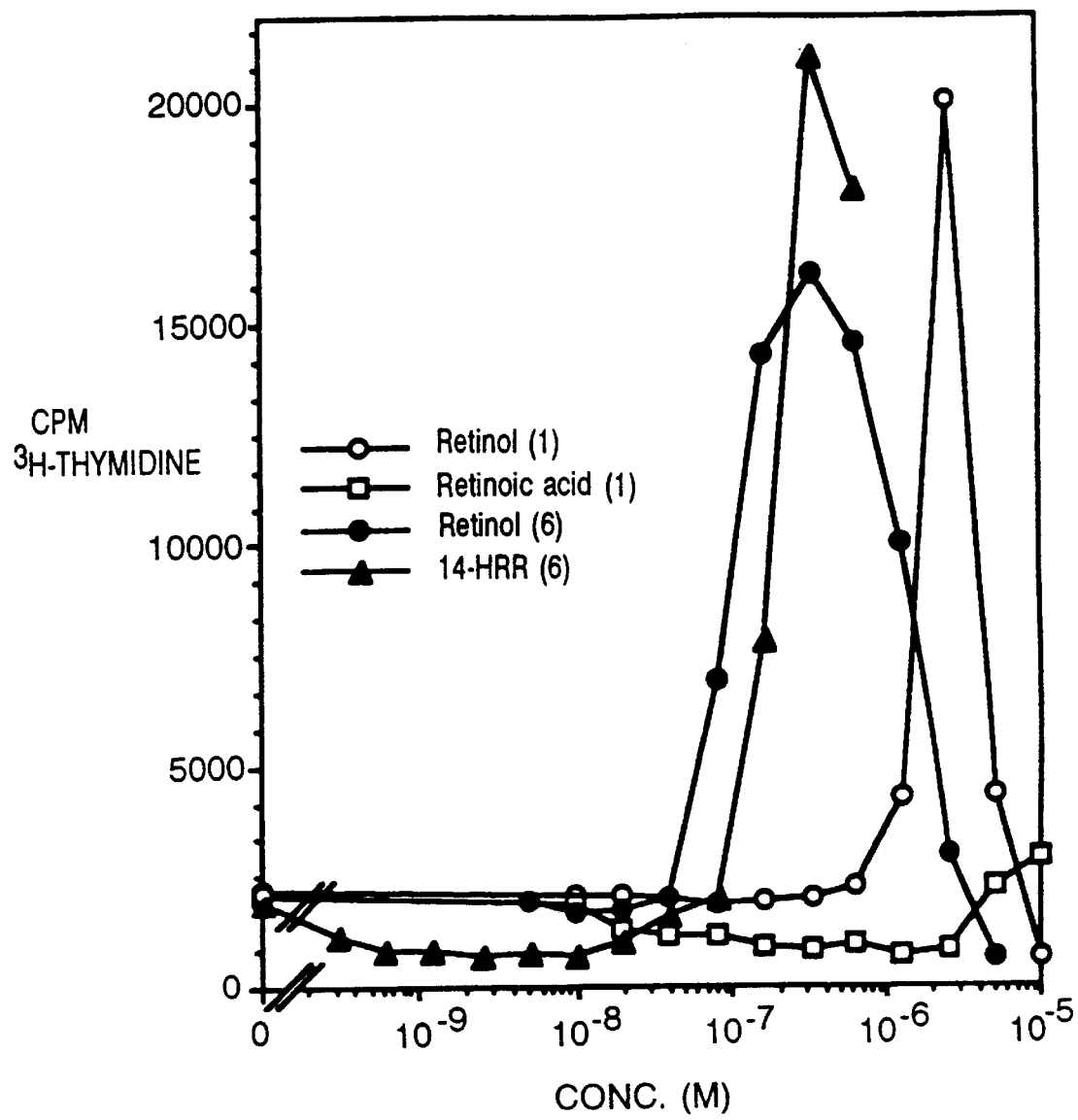
Figure 17D:
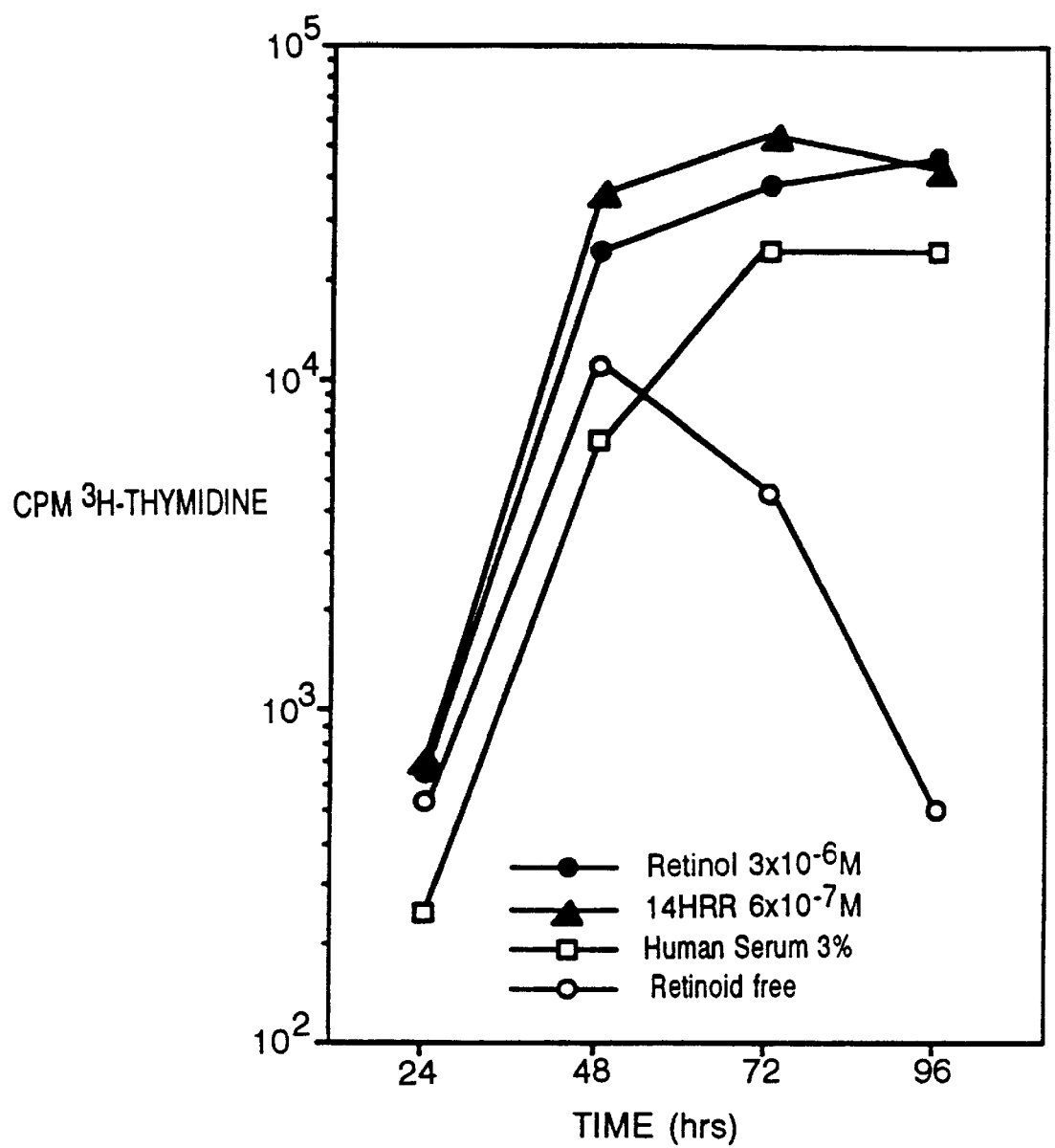

Because the phenotype analysis had implicated mature T cells among the thymocytes responsive to anti-CD3 activation in the presence of retinoid, we tested whether this finding also held true for peripheral T cells. FIG. 17 indicates that stimulation of lymph node T cells was dependent on the presence of retinal although at high cell density ($2\times10^6$/ml) the dependence was less pronounced than at low density ($5\times10^5$/ml or below) (FIG. 17A). The dose response curves for lymph node T cells were very similar to those for thymocytes (compare FIGS. 15 and 17B). Furthermore, 14HRR is effective over the same dose range as observed for thymocytes, whereas retinoic acid is nearly inert, except for a very modest stimulatory activity elicited at $10^{-5}M$ concentration.

Because a proportion of lymph node T cells proliferated upon activation by anti-CD3 independently of retinal, we tested whether these cells might belong to a particular subset. However, when $CD4^+$ and $CD8^+$ subsets were purified by negative immunoselection, and tested for proliferation in the presence or absence of retinol, they behaved no differently from unseparated cells, i.e., each subset responded to the activating signal (anti-CD3 for $CD4^+$ cells; anti-CD3 plus IL-2 for $CD8^+1$ cells) only if retinal or 14HRR were present (FIGS. 17C and D).

Retinol is required at onset of culture

We have determined the kinetics of requirement of retinal by thymocytes and have found that the highest responses were elicited when retinol was supplied together with the activation signal. When delayed by 12 hours, retinal still produced a growth supporting effect but this trailed behind by a margin of 4:1. A delay of 24 hours caused complete failure of activation.

Retinal cannot be replaced by interleukins

We have investigated whether lymphokines or cytokines known to impact on T cell activation can substitute for retinal or modulate its effect in anti-CD3-activated thymocytes. None of the four interleukins, IL-1, IL-2, IL-4 or IL-6, was capable of overcoming the requirement for retinal. However, among cytokines, interferon-gamma can sustain thymocyte proliferation in the absence of retinol, whereas TNF-α does not. When testing for synergy between retinol and lymphokines, we found all except IL-2 to moderately enhance proliferation of thymocytes. Interferon-gamma showed a clear additive effect with retinol (Table II).

Discussion

Our results indicate that retinoids play a key role in the activation of murine T cells. Using minimal culture medium consisting of RPMI 1640 supplemented with insulin, transferrin, linoleic acid, delipidated serum albumin and all-trans retinol, activation of thymic and lymph node T cells is highly effective, whether these cells are stimulated by TCR crosslinking or unphysiologically by the lectin Con A. Retinol is not absolutely required because proliferation is initiated in its absence when the anti-CD3 density is very high, but even then proliferation reaches only one quarter the level of comparable cultures with retinol (FIG. 14B). Thus, it appears that a very strong TcR signal suffices to activate some T cells whereas retinol facilitates the activation of a much larger population. Retinol is needed at the initiation of culture and cannot be withheld for longer than a few hours without loss of proliferation capacity (FIG. 18). It is unclear from present experiments whether once activated, continued proliferation of normal T cells is also critically dependent on retinol in the culture medium. This issue is under investigation. 13-cis-retinol and retinal but not all-trans retinoic acid can substitute for retinal. The retinoid, 14-hydroxy-retro-retinol (14HRR) was also capable of supporting activation and sustaining proliferation of T cells, provided that is was replenished twice daily to compensate for its rapid decay. Our experiments do not distinguish between defined stages in the activation process of resting T cells beyond a broad requirement during early and late events. The impact on early events is implied by the observation that a 12-hour delay in retinol addition leads to stagnation, whereas the requirement for late vents follows from the observation that a single addition of 14HRR does not enable sustained proliferation. Although retinol appears to be an important cofactor, its presence may not be absolutely required in situations where potent alternate second signals are given. For instance, interferon-gamma proved quite efficient in anti-CD3-mediated activation in the absence of retinol (Table II).

Retinol, an essential vitamin, circulates in blood as a stable complex with retinol-binding protein (RBP) and transthyretin (TTR) (41). Its concentration in plasma is closely regulated at $1-2\times10^{-6}M$, whereas intracellular concentrations vary between tissues and appear to depend on the extant concentration of cellular retinol-binding protein (CRBP) (42). Because the tissue distribution of CRBP is nearly universal (43), it is inferred that retinol is present ubiquitously as well (44). A general physiological purpose of retinal itself has not been discerned, but there is agreement that retinal is used as a metabolic precursor of other retinoids, including 11-cis-retinal functioning as the photoreceptor in vision (45), all-trans retinoic acid which has been implicated in differentiation (46) and morphogenesis (47), and 9-cis retinoic acid that has been found to activate the RXR receptor (48,49).

Pursuing the hypothesis that retinol serves as a precursor of intracellular retinoid mediators, we have analyzed the metabolic products of retinol in B lymphocytes in previous studies (32,33). B lymphocytes did not produce retinoic acids, but they synthesize a new class of retinoids, the retro-retinoids, hitherto seen in nature only in the form of anhydro-retinol (50). Retro-retinoids are characterized by a completely planar ring-to-tail configuration, rigidly enforced by the rearrangement of the carbon double bond system so as to fix the six-membered ring by a double bond to the polyene tail. 14-hydroxy-retro-retinol is the first retro-retinoid to be isolated from mammalian cells and is 20–40 times more potent on a concentration basis in preventing necrotic cell death in β lymphocytes than its parent molecule, retinol.

Our results in this study show that retinol is an essential component in serum-free medium without which T cells can be activated only superficially and T cell proliferation does not proceed. Serum is a customary supplement of culture media used for in-vitro experimentation in cellular immunology, and the retinol herein might be part of the secret why it is such an effective ingredient in growth medium. As implied by our results, however, components of serum other than retinol, albumin (as a transport protein of fatty acids), transferrin (to regulate iron metabolism) and insulin may not be needed for lymphocyte cultures. Indeed, the advantage of avoiding unknown influences by hormones and growth factors (notably PDGF) forms a compelling reason for experimentation in defined serum-free medium as discussed in detail by Daynes and colleagues (26).

In the serum-free medium composition used here, retinol is not protected by its physiological serum carrier proteins, RBP and TTR, is therefore labile and decays with a half-life of <24 h in cell culture (32). The optimally effective dose of retinal is $2 \times 10^{-6}$M, when given once in a 3-day culture, or $2 \times 10^{-7}$M when provided at 12 hour intervals. This dose range corresponds to the concentration of retinal in normal sera, i.e., $1-2 \times 10^{-6}$M.

The question whether retinal mediates its effect on T cells through its metabolic product, 14HRR, cannot be answered definitely by the experiments shown in this study but the following arguments support this mechanism: First, 14HRR is capable of supporting T cell activation and proliferation in the absence of any extraneous source of retinal. Second, the dose response curves for retinal and 14HRR in T cells are very similar, a finding of some concern, because a putative downstream mediator (i.e., 14HRR) might have been expected to be active at lower concentrations than its precursor. However, 14HRR is intrinsically a much more labile molecule than retinal. Previous analyses with B lymphocytes have demonstrated activity for 14HRR at $5 \times 10^{-8}$M concentration compared to $2 \times 10^{-7}$M for retinal, a 40-fold difference (33). Why T cells require higher concentrations of 14HRR is unclear. Third, 14HRR is a metabolic product of retinal on the basis of isotope labeling experiments and because of the fact that 14HRR is an optically active compound—and therefore enzymatically derived (33). Fourth, 14HRR (in contrast to retinal) does not revert to retinal. Fifth, it is noteworthy that T lymphocytes neither respond to externally provided retinoic acid nor synthesize appreciable amounts of it. Thus, 14HRR does not appear to be an intermediary compound in retinoic acid synthesis, an unlikely possibility on structural considerations anyway.

While these considerations leave unanswered the question whether 14HRR might be the intracellular mediator itself, they strongly suggest a regulatory retinol pathway distinct from that of retinoic acid observed in non-lymphoid cells. Retinoic acid has frequently been referred to as the active mediator of retinol effects, but our findings suggest alternative mediators and pathways. Having dismissed retinoic acid as an actual mediator in lymphocytes, it might be useful to recall the mechanism of retinoic acid action as a possible analogy by which 14HRR (or its active derivative) might function. Retinoic acid appears to be synthesized locally be unspecified regulatory cells and to pass into target cells where it is bound by a class of specific cytoplasmic retinoic acid binding proteins. The function of these cytoplasmic complexes is unknown. Retinoic acid then translocates to the nucleus and binds to one of three known specific nuclear receptor proteins, RAR-alpha, -beta or -gamma (6,51–53). Binding of the ligand, all-trans retinoic acid or 9-cis retinoic acid confers regulatory changes to the transcription of the respective gene(s) that bind RAR. The same principle governs gene activation by interaction of 9-cis retinoic acid with RXR (48,49). Moreover, ligand-assisted transcriptional regulation is also the mechanism by which steroids function. Indeed, because retinoids and steroids are biochemically related as members of the same isoprenoid superfamily, it becomes increasingly clear that a large system of ligands has evolved from this chemical family to fulfill the demands of differential gene usage in complex organisms (54). The discovery of a parallel large family of genetically homologous and structurally related nuclear receptors emphasizes this point (7). By analogy, 14HRR might also be involved in ligand-assisted transcription. Whereas we have no direct evidence for this, in work to be published elsewhere we have observed that 14HRR facilitates the expression of immediate early genes in fibroblasts. If substantiated for T cells, this finding would handsomely explain the requirement for retinoids in T cell activation.

Throughout our work we have been concerned that our results might violate the precept of dual signaling in T cell activation (55) (and see review by Mueller et al. (56)). According to this hypothesis TcR receptor occupancy must be accompanied by a second signal emanating under physiological conditions from an as yet undefined accessory cell/T cell interaction. The B7/CD28 pair of intereaction molecules might fulfill that function (57). Our findings, however, imply that the accessory signal, regardless of whether this is given by B7 or through another mechanism, is not obligatory because we obtained maximal activation of thymocytes and T cells in the absence of accessory cells by immobilized anti-CD3e mAb or Con A alone. This finding runs counter to expectation and must be ascribed to the unusual culture conditions employed by us, notably the addition of the retinol cofactor. In commonly used FCS-containing medium we find indeed no activation in the absence of APC, whether or not additional retinol is supplied. The dramatic difference in T cell stimulation in serum-free ITLB medium supplemented with retinol implies that FCS imparts inhibitory signals to T cells as suggested by Daynes et al. (26). On the other hand, we have not used protein-free conditions and cannot rule out the possibility that transferrin or insulin impart to T cells mitogenic signals that mimic a requisite secondary signal. The important question in our continuing investigation is to determine how retinol and its metabolic product, 14HRR, are to be integrated into the intracellular signaling events alongside the other known biochemical consequences of TcR triggering: IP3 and DAG production.

We have attempted to determine whether retinal is required during the activation phase, $G_0$ to $G_1$, during the progression through S phase, or during both phases. Our results support the notion that retinal is needed for initial activation, because a delay in addition of retinol after the TCR signal was given caused a marked decrease in proliferation. The answer to the second question is less clear because retinol, once given to cells, cannot easily be removed by washing due to its lipid nature. However, a single dose of 14HRR given at initiation of culture, and decaying with a half-life of ~4 hr, was insufficient to drive T cell proliferation speaking for a continuous requirement of retinol also for transition to S phase. Supporting this notion is also our published record concerning continuously growing lymphoid tissue culture lines that are dependent on retinal (3).

To complement the study of activation requirements in serum-free medium we have inquired into the role of exogenous lympho- and cytokines. The salient points of these experiments are that none of the interleukins tested (IL-1, IL-2, IL-4 and IL-6) nor TNF-alpha are substitutes for retinol. They are in agreement with the assumption that retinol needs to be physically present as a source for further metabolic modifications. However, this argument is partly negated by the observation that IFN-gamma can circumvent the retinol requirement and initiate durable proliferation in the absence of retinol or 14HRR, whereas strong additive effects were seen when retinoids were present simultaneously with IFN-gamma.

TABLE II

Growth-stimulating Effect Of Retinol On Thymocytes In The Presence Of Different Interleukins

| Stimulating Agent | U/ml | Growth-stimulating effect with or w/o Retinol CPM anti-CD3 | |
|---|---|---|---|
| | | no Retinol | $10^{-6}$ M Retinol |
| IL-1 | 10 | 959 ± 30 | 118,924 ± 3,051 |
| IL-2 | 2 | 458 ± 156 | 77,343 ± 11,739 |
| IL-4 | 5 | 991 ± 105 | 115,849 ± 20,630 |
| IL-6 | 5 | 1,005 ± 815 | 130,590 ± 25,803 |
| IFN-gamma | 40 | 81,876 ± 11,868 | 220,359 ± 27,726 |
| TNF-alpha | 12 | 464 ± 95 | 122,905 ± 11,577 |
| IL-2 + IL-4 | 2/5 | 1,081 ± 103 | 103,025 ± 5,280 |
| none | — | 585 ± 207 | 79,247 ± 17,567 |

Proliferation of activated thymocytes in response to interleukins in presence and absence of retinol. Purified thymocytes ($5\times10^5$ cells/well) were activated with immobilized anti-CD3 antibody in serum-free medium in the presence or absence of interleukins and retinol ($3\times10^{-6}$M). Proliferation was assayed after three days by tritiated thymidine incorporation.

Example C
A. Chemical studies 13,14DHR was first observed as a metabolite of retinol in activated lymphocytes. Mouse spleen cells were activated with anti-CD3 and labeled with $^3$H retinol (New England Nuclear, Cat. #) for an 18 hour culture period. Cells were then harvested and the cell-dissociated retinoids extracted with organic solvent according to the method of McLean. (13). The retinoids were chromatographed on a reversed-phase $C_{18}$ column (Vydac) using a water/methanol/chloroform gradient, as indicated in FIG. 20. The radioactivity eluting over time was monitored by an on-line liquid scintillation counter. FIG. 20 represents a plot of radioactivity versus elution time. 13,14DHR is characterized by retention time of 16.8 minutes with the gradient shown. The substances emerging at time 18.5 and 21.5 are 14HRR and all-trans retinol, respectively.

Large-scale purification of this compound from 100 L of Hela cells by a series of chromatographic steps yielded 160 μg of material of apparent homogeneity. 13,14 DHR elutes from a preparative $C_{18}$ column of 250 by 22 mm internal diameter (ID) with water/methanol at 19/81 v/v; a semi-preparative $C_{18}$ column of 250 by 10 mm ID with water-acetonitrile at 30/70 v/v; and an analytical C4 column of 250 by 4.6 mm ID with water/methanol at 26/74 v/v. The structure of this compound was solved by the following spectroscopic measurements:

UV absorption. As shown in FIG. 21B, 13,14DHR displays a single symmetrical absorption peak with maximum at 291 nm in methanol. This shift in λ max to a shorter wavelength in comparison to retinol (λ max=324 nm) is indicative of the loss of one double bond in the polyene tail of the retinoids.

Mass spectroscopy. The low resolution electron ionization mass spectrum is presented in FIG. 22A. The molecular ion has a mass of 320. The major fragments have m/z of 302, 284, 272, and 259. High-resolution mass spectrum (matrix PFK) gave an observed value of 320.2354 for the molecular ion corresponding to the atomic composition of $C_{20}H_{32}O_3$ (calculated value: 320.2351). Therefore, 13,14DHR has two additional oxygen and two additional hydrogen atoms compared to the parent molecule, retinol.

Proton nuclear magnetic resonance. The results of $^1$H-NMR are shown in FIG. 23. CD spectroscopy shown in FIG. 21A. These structural parameters taken together define the structure of 13,14 dihydroxy-retinol (FIG. 19).

B. Biological studies

1. Production of 13,14DHR precedes production of 14HRR

The kinetics of biosynthesis of 13,14DHR and 14HRR were determined in 5/2 lymphoblastoid cells. These cells were cultured in the presence of $^3$H retinol for different time periods, and the cell-associated retinoids extracted as referenced above. They were then chromatographed on an analytical $C_{18}$ column as described in FIG. 20. The sizes of peaks emerging at 16.8 minutes, representing 13,14DHR, and 18.5 minutes, representing 14HRR, were measured and plotted in the bar diagram of FIG. 24. It is clearly evident that production of 13,14DHR precedes that of 14HRR.

2. 13.14DHR can be converted to 14HRR

Lymphoblastoid 5/2 cells devoid of retinol were cultured in the presence or absence of $10^{-6}$M 13,14DHR for 1 and 2 hours in ITLB medium. The retinoids extracted from the cell pellets were separated by HPLC according to FIG. 20. The 13,14DHR-fed cultures produced 14HRR which was identified by its retention time and its specific UV absorption pattern (fine structure and specific absorption maxima) (FIG. 25). There was no 14HRR measurable in control cultures.

These experiments indicate that retinol is first converted to 13,14DHR and then to 14HRR. In the absence of retinol, 14HRR is synthesized from 13,14DHR. Therefore 13,14DHR is a biosynthetic intermediate in 14HRR biosynthesis from retinol.

B. Biological activity of 13,14DHR

5/2 cells were grown in the absence of retinol in a medium containing the basic RPMI 1640 amino acid/salt mixture, insulin (5 μg/ml), transferrin (5 μg/ml), albumin (0.1%) and linoleic acid ($10^{-6}$M) (ITLB). They failed to replicate under these conditions. As reported previously, the addition of retinol or 14HRR restores the capacity to proliferate. When 13,14DHR was added instead, proliferation was restored as well. The dose-response curve shown in FIG. 26 indicates an effective concentration of $10^{-7}$M.

T cells also respond to the action of 13,14DHR. As reported, the activation of resting T cells is critically dependent on retinol as a co-factor in the culture medium. Initiation of proliferation cannot be accomplished in the absence of retinol. 13,14DHR can effectively substitute for retinol. The 13,14DHR effective concentration is $10^{-6}$M (similar to that needed for support of 3 cell proliferation). We conclude that 13,14DHR acts as a modulator of lymphocyte function.

C. Chemical Synthesis of 13,14DHR

Route 1

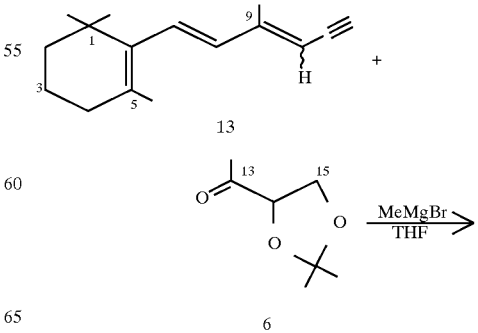

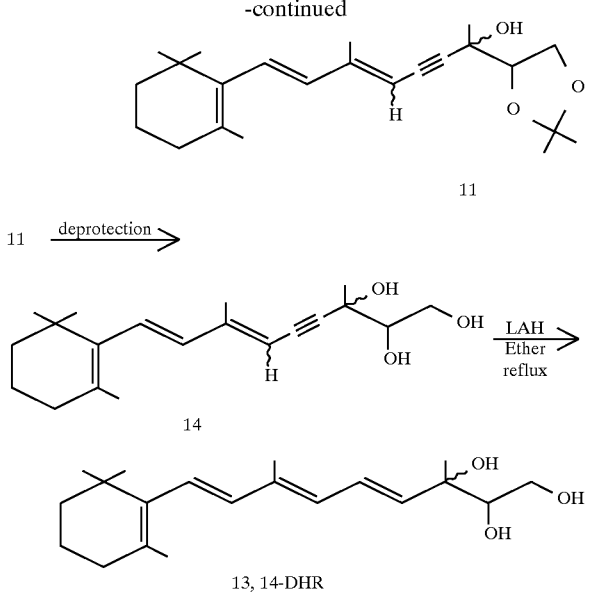

Compound 13: mixture of 9E/9Z isomers obtained according to literature procedures (58).

Compound 6 can be obtained as R or S (see section on synthesis of 14-HRR.

The synthesis of 13,14-DHR was carried out starting with (R)-glyceraldehyde aceonide (P=CMe$_2$; see refs. 59, 60) and led to a mixture of (13R, 14R)- and (13S, 14R)-DHR separable by chromatography. Each diastereomer is a mixture of 9E and 9Z isomers also separable by chromatography.

The absolute configuration at C13 center is assigned for each isomer by CD studies.

(13S, 14S)- and (13R, 14S)-DHR may be synthesized accordingly starting from protected S-glyceraldehyde.

Route 2

Candidates for biological precursors of 13,14-DHR are the following 13,14-epoxy-retinols.

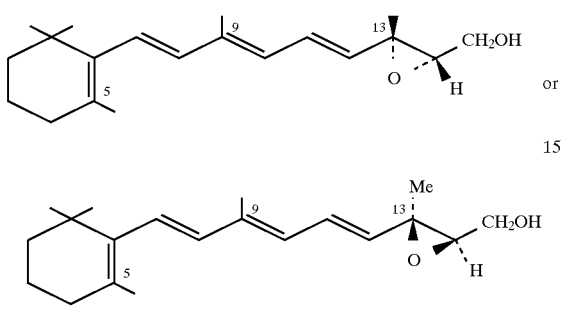

Both compounds may be prepared by asymetric-epoxidation of retinol (61) and submitted to biological and chemical conversion to 13,14-DHR.

REFERENCES

1. Wolbach, S. B. et al. *J. Exp. Med.* 42:753 (1925).
2. Rahmathullah, L. et al. *N. Eng. J. Med.* 323:929–935 (1990).
3. Buck, J. et al. *J. Ex. Med.* 171:1613–1624 (1990).
4. Slack, J. M. *Nature (London)* 327:553–554 (1987).
5. Petkovich, M. et al. *Nature (London)* 330:444–450 (1987).
6. Giguere, V. et al. *Nature (London)* 330:624–629 (1987).
7. Mangelsdorf, D. J. et al. *Nature (London)* 345:224–229 (1990).
8. Evans, R. M. *Science* 240:889–895 (1988).
9. McDonald, P. N. and Ong D.E. *J. Biol. Chem* 262:10550 (1987).
10. Schreckenbach, T., B. Walckhoff, D. Oesterhelt *Eur. J. Biochem.* 76:499–511 (1977).
11. Reppe, K., in "Houben-Weyl, Methoden der Organischen Chemie", Thieme-Verlag Stuttgart (E. Muller Ed.), Vol. V 1d:7–31 (1970).
12. Blazar, B. A. et al. *Cancer Res.* 43:4562 (1983).
13. McLean, et al. *Clin. Chem.* 28:693–696 (1982).
14. Gonnella, N. C., K. Nakanishi, V. S. Martin, K. B. Sharpless *J. Am. Chem. Soc.* 104:3775–3776 (1982).
15. Natori, S., in "Natural Products Chemistry", K. Nakanishi et al., Eds. Vol. I, Kodansha Ltd., Tokyo, Academic Press, Inc. New York, N.Y., pp 30–32 (1974).
16. Beecham, A. F. *Tetrahedron.* 27:5207 (1971).
17. Vetter, W. et al., in "Carotenoids", O. Isler Ed. Berkhauser Verlag Basel, 204–243 (1971).
18. Gosswein, L. 1976, Diplomarbeit. Univ. of Wurzburg.
19. Beutel, R. H. et al. *J. Am. Chem. Soc.* 77:5166–5167 (1955).
20. Oroshnik, W. et al. *J. Am. Chem. Soc.* 74:295–304 (1952).
21. Mayer, H. et al. *Helv. Chim. Aca.* 50:1606–1619 (1967).
22. Allison, J. P. and L. L. Laurie *Annu. Rev. Immunol.* 5:503 (1987).
23. Reinherz, E. L., O. Acuto, M. Fabbi, A. Bensussan, C. Milanese, H.-D. Royer, S. C. Meurer and S. F. Schlossman *Rev. Immunol.* 81:95–130 (1983).
24. Lewin, B. *Cell* 64:303–312 (1991).
25. Green, S. and P. Chambon *Trends Genet.* 4:309–314 (1988).
26. Daynes, R. A., T. Dowell and B. A. Araneo *J. Exp. Med.* 174:1323–1333.
27. Iscove, N. N., and P. Melchers *J. Exp. Med.* 147:923 (1978).
28. Herzberg, V. L., and K. A. Smith *J. Immunol.* 138:998–1004 (1987).
29. Wolbach, S. B. and P. R. Howe *J. Exp. Med.* 42:753 (1925).
30. David, C. Y., and J. L. Sell *J. Nutr.* 113:1914 (1983).
31. Bieri, J. G., E. G. McDaniel, and W. E. Rogers *Science* (Wash. D.C.) 163:574 (1969).
32. Buck J., A. Myc, A. Garbe, and G. Cathomas. *J. Cell Biol.* 115:851–859 (1991).
33. Buck, J., F. Derguini, E. Levi, K. Nakanishi, and U. Hammerling *Science* 254:1654–1656 (1991).
34. Leo, O., M. Foo, D. H. Sachs, L. E. Samelson, and J. A. Bluestone *Proc. Natl. Acad. Sci. USA* 84:1374 (1987).
35. Kappler, J. W., B. Skidmore, J. White, and P. Marrack *J. Exp. Med.* 153: 1198–1214 (1981).
36. Ohara, J. and W. E. Paul *Nature* 315:333–336 (1985).
37. Hammerling, G. J., U. Hammerling, and H. Lemke *Immunogenetics* 8:433–445 (1979).
38. Hammerling, G. J., U. Hammerling, and L. Flaherty *J. Exp. Med.* 150:108 (1979).
39. Dialynas, D. P., D. B. Wilde, P. Marrack, A. Pierres, K. A. Wall, W. Harran, G. Otten, M. R. Locken, M. Pierres, J. Kappler, and F. W. Fitch *Immunol. Rev.* 74:29–56 (1983).
40. Julius, M. E., E. Simpson, and L. A. Herzenberg *Eur J. Immunol.* 3:645–649 (1973).
41. Goodman, D. S. Plasma retinol-binding protein. In the Retinoids. Vol. 2. M. B. Sporn, A. B. Roberts, and D. S. Goodman, editors, Academic Press, New York, 41–48 (1984).

42. Chytil F., and D. E. Ong. Cellular retinoid-binding protein. In The Retinoids. Vol. 2. M. B. Sporn, A. B. Roberts, and D. S. Goodman, editors, Academic Press, New York, 89–123 (1984).
43. Kato, M., W. S. Blaner, J. R. Mertz, K. Das, and D. S. Goodman *J. Biol. Chem.* 260:4832–4838 (1985).
44. Noy. N., and W. S. Blaner *Biochemistry* 30:6380–6386 (1991).
45. Wald, G. *Science* 162:230–239 (1968).
46. Roberts, A. B. and M. B. Sporn. Cellular biology and biochemistry of the retinoids. In The Retinoids. Vol. 2. M. B. Sporn, A. B. Roberts, and D. S. Goodman, editors. Academic Press, New York, 209–286 (1984).
47. Tabin, C. J. *Cell* 66:199–217 (1991).
48. Levin, A. A., L. J. Sturzenbecker, S. Kazmer, T. Bosakowski, C. Huselton, G. Allenby, J. Speck, C. Kratzeisen, M. Rosenberger, A. Lovey, and J. F. Grippo *Nature* 355:359–361 (1992).
49. Heyman, R. A., D. J. Mangelsdorf, J. A. Dyck, R. B. Stein, G. Eichele, R. M. Evans, C. Thaller *Cell* 68:397–406 (1992).
50. Castle, D. C., A. E. Gillam, I. M. Heilbron, and J. W. Thompson *Biochem. J.* 28:1702–1711 (1934).
51. Giguere, V., S. Lyn, P. Yip, C. H. Siu, and S. Amin *Proc. Natl. Acad. Sci. USA* 87:6233–6237 (1990).
52. Krust, A., P. Kastner, M. Petkovich, A. Zelent, and P. Chambon *Proc. Natl. Acad. Sci. USA* 86:5310–5314 (1989).
53. Brand N., M. Petkovich, A. Krust, P. Chambon, H. de The, A. Marchio, P. Tiollais, and A. Dejean *Nature (London).* 332:850–853 (1988).
54. Moore, D. D. *New Biol.* 2:100–105 (1990).
55. Bretscher, P. and M. Cohn Science 169:1042 (1970).
56. Mueller, D. L., M. K. Jenkins, and R. H. Schwartz *Annu. Rev. Immunol.* 7:445–480 (1989).
57. Linsley, P. S., E. A. Clark, and J. A. Ledbetter *Proc. Natl. Acad. Sci. USA* 87:5031–5035 (1990).
58. J-L Olive, M. Mousseron-Canet, J. Dornand *Bull. Soc. chim. Fr.* 9, 3247 (1969).
59. E. Baer, H. O. L. Fischer *J. Biol. chem.* 128, 463 (1939).
60. S. J. R. Baker *J. Am. Chem. Soc.* 74, 827 (1952).
61. T. Katsuki, K. B. Sharpless *J. Am. Chem. Soc.* 102, 5974–5976 (1980).

What is claimed is:

1. A purified retinoid compound having the structure:

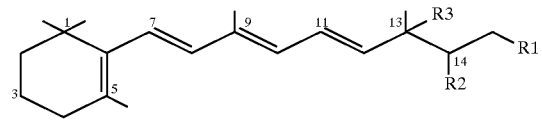

wherein the configuration of the C7, C9, and C11 double bond independently is Z or E and the absolute configuration at C13 and C14 is independently R or S; wherein R1 is hydroxyl, alkyl, alkyl halide, alcohol, ester, ether, aldehyde, ketone, carboxylic acid, carboxylic ester, acyl halide, amide, nitrile, or amine; wherein R2 and R3 are independently hydroxyl, halide, alkoxy, ester, alkyl, alcohol, ether, aldehyde, ketone, carboxylic acid, carboxylic ester, nitrile, amine, azide, alkyl halide, acid halide, acid azide, or amide; or wherein R2 and R3, or R1 and R2 may be replaced by a 13,14-oxirane or 14,15-oxirane group, respectively.

2. The purified retinoid compound of claim 1, wherein R1, R2 and R3 are hydroxyl groups.

3. A pharmaceutical composition which comprises the compound of claim 1 and a pharmaceutically acceptable carrier.

4. A pharmaceutical composition which comprises the compound of claim 2 and a pharmaceutically acceptable carrier.

5. The pharmaceutical composition of claim 4, wherein the pharmaceutically acceptable carrier is a retinol binding protein.

6. A compound having the structure:

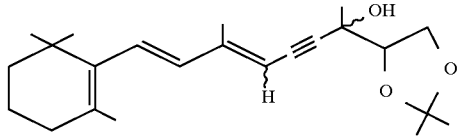

7. A compound having the structure:

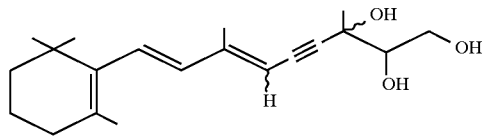

* * * * *